(12) United States Patent
Cooney et al.

(10) Patent No.: US 8,598,378 B2
(45) Date of Patent: Dec. 3, 2013

(54) METHODS AND COMPOSITIONS FOR EXTRACTION AND TRANSESTERIFICATION OF BIOMASS COMPONENTS

(75) Inventors: Michael J. Cooney, Honolulu, HI (US); Gregory Young, Redwood City, CA (US)

(73) Assignee: University of Hawaii, Honolulu, HI (US)

( * ) Notice: Subject to any disclaimer, the term of this patent is extended or adjusted under 35 U.S.C. 154(b) by 160 days.

(21) Appl. No.: 12/404,176

(22) Filed: Mar. 13, 2009

(65) Prior Publication Data

US 2009/0234146 A1 Sep. 17, 2009

Related U.S. Application Data

(60) Provisional application No. 61/036,913, filed on Mar. 14, 2008, provisional application No. 61/044,412, filed on Apr. 11, 2008.

(51) Int. Cl.
*C07C 51/43* (2006.01)

(52) U.S. Cl.
USPC ............................. 554/174; 210/638; 210/639

(58) Field of Classification Search
USPC .................................. 554/174; 210/638, 639
See application file for complete search history.

(56) References Cited

FOREIGN PATENT DOCUMENTS

WO WO 2006095134 9/2006

OTHER PUBLICATIONS

Stephen Dureche et al. "Extraction of liquids from municipal wastewater plant microorganisms for production of biodiesel". J. Amer. Oil. Chem. Soc., 2007, vol. 84, pp. 181-187.*
Deng et ai., 2001, "Ionic liquid as a green catalytic reaction medium for esterifications," Journal of Molecular Catalysis A: Chemical 165, pp. 33-36.*
Zhu, et al. 2003. "Bronstead acidic ionic liquid 1-methylimidazolium tetrafluoroborate: A green catalyst and recyclable medium for esterification." Green Chemistry 5:38-39.*
Antolin, et. al. 2002. "Optimisation of biodiesel production by sunflower oil transesterification." *Bioresource Technology* 83:111-114.
Apt, K. E., and P. W. Behrens 1999. "Commercial developments in microalgal biotechnology." *Journal of Phycology* 35:215-226.
Azam, et al. 2005. "Prospects and potential of fatty acid methyl esters of some non-traditional seed oils for use as biodiesel in India." *Biomass and Bioenergy* 29:293-302.
Carvalho, A. P., and F. Xavier Malcata. 2005. "Preparation of fatty Acid Methyl Esters for Gas-Chromatographic Analysis of Marine Lipids: Insight Studies." *Journal of Agricultural and Food Chemistry* 53:5049-5059.
Chen, F., and M. R. Johns. 1991. "Effect of C/N ratio and aeration on the fatty acid composition of heterotrophic *Chlorella* sorokiniana." *Journal of Applied Phycology* 3:203-209.
Chen, Feng 1996. "High cell density culture of microalgae in heterotrophic growth." *Trends in Biotechnology* 14:421-426.
Chisti, Yusuf 2007. "Biodiesel from microalgae." *Biotechnology Advances* 25:294-306.
Demirbas, Ayhan 2009. "Progress and recent trends in biodiesel fuels." *Energy Conversion and Management* 50:14-34.

(Continued)

*Primary Examiner* — Deborah D Carr
(74) *Attorney, Agent, or Firm* — Davis Wright Tremaine LLP

(57) ABSTRACT

Methods and compositions are disclosed for the direct transesterification and extraction of bio-lipids and bio-oils in the production of biofuel, particularly fatty acid methyl ester products.

22 Claims, 24 Drawing Sheets

(56) References Cited

OTHER PUBLICATIONS

Dote, et al. 1994. "Recovery of liquid fuel from hydrocarbon-rich microalgae by thermochemical liquefaction." *Fuel* 73(12):1855-1857.
Fischer, et al. 2008. "Selection and optimization of microbial hosts for biofuels production." *Metabolic Engineering* 10:295-304.
Folch, et al. 1957. "A simple method for the isolation and purification of total lipids from animal tissues." *Journal of Biological Chemistry* 226:497-509.
Fraga-Dubreuil, et al. 2002. "Catalysed esterifications in room temperature ionic liquids with acidic counteranion as recyclable reaction media." *Catalysis Communications* 3:185-190.
Ginzburg, Ben-Zion 1993. "Liquid fuel (oil) from halophilic algae: a renewable source of non-polluting energy." *Renewable Energy* 3:249-252.
Ignat'Ev, et al. 2005. "New ionic liquids with tris(perfluoroalkyl)trifluorophosphate (FAP) anions." *Journal of Fluorine Chemistry* 126(8):1150-1159.
Kandpal, J. B. And M. Madan. 1995. "*Jatropha curcas*: A renewable source of energy for meeting future energy needs." *Renewable Energy* 6(2):159-160.
Kumar, A. and S. Sharma. 2008. "An evaluation of multipurpose oil seed crop for industrial uses (*Jatropha curcas* L.): A review." *Industrial Crops and Products* 28:1-10.
Lang, et. al. 2001. "Preparation and characterization of bio-diesels from various bio-oils." *Bioresource Technology* 80:53-62.
Lee, et al. 2008. "Metabolic engineering of microorganisms for biofuels production: from bugs to synthetic biology to fuels." *Current Opinion in Biotechnology* 19:556-563.
Lewis, et al. 2000. "Evaluation of extraction methods for recovery of fatty acids from lipid-producing microheterotrophs." *Journal of Microbiological Methods* 43:107-116.
Li, et al. 2007. "High-density cultivation of oleaginous yeast *Rhodosporidium toruloides* Y4 in fed-batch culture." *Enzyme and Microbial Technology* 41:312-317.
Milne, et al. 1990. "Catalytic conversion of Microalgae and vegetable oils to premium gasoline, with shape-selective zeolites." *Biomass* 21:219-232.
Minowa, et al. 1995. "Oil production from algal cells of *Dunaliella tertiolecta* by direct thermochemical liquefaction." *Fuel* 74(12):1735-1738.
Narasimharao, et al. 2007. "Structure-activity relations in Cs-doped heteropolyacid catalysts for biodiesel production." *Journal of Catalysis* 248:226-234.
Neto, et al. 2007. "1-n-Butyl-3-methylimidazolium tertachloroindate (BMI•InCl$_4$) as a media for the synthesis of biodiesel from vegetable oils." *Journal of Catalust* 249:154-161.
Pohl, P. and H. Wagner 1972. "Control of fatty acid and lipid biosynthesis in *Euglena gracilis* by ammonia, light and DCMU." *Z. Naturforsch* 276:53-61.
Poirreck, et al. 1984. "Biomass production, total protein, chlorophylls, lipids and fatty acids of fresh water green and blue-green algae under different nitrogen regimes." *Phytochemistry* 23(2):207-216.
Rosenberg, et al. 2008. "A green light for engineered algae: redirecting metabolism to fuel a biotechnology revolution." *Current Opinions in Biotechnology* 19:430-436.
Seddon, Kenneth R. 1997. "Ionic liquids for clean technology." *Journal of Chemical Technology and Biotechnology* 68:351-356.
Shi, et al. 2000. "Heterotrophic production of biomass and lutein by *Chlorella* protothecoides on various nitrogen sources." *Enzyme and Microbial Technology* 27:312-318.
Shi, et al. 2002. "High-yield production of lutein by the green microalga *Chlorella* protothecoides in heterotrophic fed-batch culture." *Biotechnol. Prog.* 18:723-727.
Suen, et al. 1987. "Total Lipid Production of the Green Alga Nannochloropsis SP. QII Under Different Nitrogen Regimes." *Journal of Phycology* 23:289-296.
Vicente, et. al. 2004. "Integrated biodiesel production: a comparison of different homogeneous catalysts systems." *Bioresource Technology* 92:297-305.
Wen, et al. 2002. "High cell density culture of the diatom Mitzschia laevis for eicosapentaenoic acid production: fed-batch development." *Process Biochemistry* 37:1447-1453.
Wu, et. al. 1994. "New discoveries in study on hydrocarbons from thermal degradation of heterotrophically yellowing algae." *Science in China* (B) 37(3):326-335.
Yoon, et al. 1982. "Effect of carbon and nitrogen sources on lipid production of Rhodotorulu gracilis" *Journal of Fermentation Technology* 60(3):243-246.
Zhang, et. al. 2003. "Biodiesel production from waste cooking oil: 1. Process design and technological assessment." *Bioresource Technology* 89:1-16.
Dufreche, et al. 2007. "Extraction of lipids from municipal wastewater plant micoorganisms for production of biodiesel." *J Amer Oil Chem Soc* 84:181-187.
International Preliminary Report on Patentability for PCT Application No. PCT/US2009/037195, dated Sep. 23, 2010, 6 pages.
Narasimiharao et al., 2007, "Catalysts in Production of Biodiesel: A review." *Journal of Biobased Materials and Bioenergy*. vol. 1, pp. 19-30.
Deng et al., 2001, "Ionic liquid as a green catalytic reaction medium for esterifications," *Journal of Molecular Catalysis A: Chemical* 165, pp. 33-36.

* cited by examiner

| GROUP | STRUCTURE | PHYSICAL PROPERTIES | |
|---|---|---|---|
| SULFOXIDES (DMSO) | $CH_3-S(=O)-CH_3$ | Bp: 189<br>Dm: 3.96<br>Dc: 47.2 | Ws: MISCIBLE |
| CARBOXYLIC ACIDS (ACETIC ACID) | $CH_3-C(=O)-OH$ | Bp: 118C<br>Dm: 1.74<br>Dc: 6.15 | Ws: MISCIBLE |
| AMIDES (ACETAMIDE) | $CH_3-C(=O)-NH_2$ | Bp: 222C<br>Dm: 3.44 (30C)<br>Dc: 38 (25C) | Ws: 200g/ 100 ml |
| ALCOHOLS (METHANOL) | $CH_3-OH$ | Bp: 64.6C<br>Dm: 1.69<br>Dc: 33.1 (20C) | Ws: MISCIBLE |
| KETONES (ACETONE) | $CH_3-C(=O)-CH_3$ | Bp: 56.2C<br>Dm: 2.88 (20C)<br>Dc: 20.7 (20C) | Ws: MISCIBLE |
| ALKYL HALIDES (CHLOROFORM) | $H-CCl_3$ | Bp: 61.7C<br>Dm: 1.01 (15C)<br>Dc: 4.81 | Ws: 0.795g/ 100g |
| ALCOHOLS (ISOPROPANOL) | $CH_3-CH(OH)-CH_3$ | Bp: 78.5C<br>Dm: 1.66<br>Dc: 318.3 | Ws: MISCIBLE |
| ESTERS (METHYL ACETATE) | $CH_3-C(=O)-O-CH_3$ | Bp: 57C<br>Dm: 1.72 (20C)<br>Dc: 6.68 (20C) | Ws: MISCIBLE |
| AMINES (PROPYLAMINE) | $CH_3-CH_2-CH_2-NH_2$ | Bp: 48C<br>Dm: 1.26<br>Dc: 5.31 | Ws: MISCIBLE |
| ALKYL HALIDES (METHYL CHLOROFORM) | $CH_3-CCl_3$ | Bp: 71.4C<br>Dm: 2.05 (15C)<br>Dc: 9.45 (20C) | Ws: IMMISCIBLE |

DECREASING POLARITY →

FIG. 20 and compositions that reduce the high cost of biodiesel production is being undertaken, such as the exploration of methods that involve minimizing raw material costs.
METHODS AND COMPOSITIONS FOR EXTRACTION AND TRANSESTERIFICATION OF BIOMASS COMPONENTS

CROSS-REFERENCE TO RELATED APPLICATIONS

This application claims priority from U.S. Provisional Application Ser. No. 61/036,913, filed on Mar. 14, 2008, and U.S. Provisional Application Ser. No. 61/044,412, filed on Apr. 11, 2008, each of which is incorporated herein by reference in its entirety.

STATEMENT REGARDING FEDERALLY SPONSORED RESEARCH OR DEVELOPMENT

This invention was made in part with Government support under DOE STTR (American Biodiesel, Inc.); Award # DE-FG02-07ER86298. The Government has certain rights in the invention.

FIELD OF THE INVENTION

The invention disclosed herein generally relates to methods and compositions for direct extraction of lipids, biopolymers, fat soluble pigments and/or proteins from biomass. In some embodiments, the methods and compositions relate to the direct transesterification of lipids from biomass. Embodiments of the invention also relate to methods and compositions for the extraction or direct transesterification of bio-lipids and bio-oils in a one-step process at low pressure and moderate temperature.

BACKGROUND OF THE INVENTION

Certain fatty acid methyl esters originating from vegetable oils, animal fats, and oil-seeds are known as biodiesel. Biodiesel fuel has received considerable attention in recent years, as it is a biodegradable, renewable and non-toxic fuel. It contributes no net carbon dioxide or sulfur to the atmosphere and emits less gaseous pollutants than normal diesel (Lang, et. al. 2001. *Bioresour. Technol.* 80:52-62; Antolin, et. al. 2002. *Bioresour. Technol.* 83:111-114; Vicente, et. al. 2004. *Bioresour. Technol.* 92:297-305). Biodiesel, primarily rapeseed methyl ester, has been in commercial use as an alternative fuel since 1988 in many European countries (Lang, et. al. 2001. supra). In spite of the favorable impact that its commercialization could provide, the economic aspect of biodiesel production prevents its development and large-scale use, mainly due to the high cost of vegetable oil (Antolin, et. al. 2002; Lang, et. al. 2001, supra). The cost of biodiesel is significantly higher than that of fossil-fuel-based diesel (Zhang, et. al. 2003. *Bioresour. Technol.* 89:1-16), thus, methods and compositions that reduce the high cost of biodiesel production is being undertaken, such as the exploration of methods that involve minimizing raw material costs.

The research of liquid fuel produced from microalgae began in the mid-1980's. Typically, the microalgal oil was extracted using process steps applied to dried microalgal biomass. The cells were freeze-dried, ruptured, and subjected to extraction and purification using a two or three-step process involving organic solvents and vacuum distillation. The recovered and purified oil was then transesterified in the presence of an alcohol and an appropriate catalyst (Narasimiharao, K., Lee, A., Wilson, K. 2007. "Catalysts in Production of Biodiesel: A review." *Journal of Biobased Materials and Bioenergy.* 1 (1):19-30; Demirbas, A. 2009. "Progress and recent trends in biodiesel fuels." *Energy Conversion and Management.* 50:14-34) to create the fatty acid methyl (or ethyl) esters that were then either evaluated by gas chromatography (GC) analysis or used as biodiesel fuel. Modifications to these methods were soon proposed, however, although these modified approaches improved recovery yields and decreased the time for GC analysis of cellular lipids, they did not diminish the voluminous use of a flammable alcohol nor diminish the need for an organic solvent (e.g., hexane) for final purification if higher chain alcohols are used in the process. For these and other reasons, large scale commercial application of direct transesterification remains limited.

Accordingly, embodiments of the invention disclosed herein relate to methods and compositions for carrying out energetically feasible methods for solvent-based extraction, recovery and/or production of bio-oil or fatty acid ester product from a variety of biomass starting materials.

SUMMARY OF THE INVENTION

Embodiments of the invention relate to a method of treating a biomass source, the methods including: contacting the biomass source with a co-solvent composition, wherein the co-solvent composition comprises at least one ionic liquid and at least one polar covalent molecule (PCM); and mixing the co-solvent composition and the biomass source, wherein said contacting and mixing results in formation of a multiple-phase composition, wherein a first phase comprises a first biomass component that is immiscible with the co-solvent composition.

In some embodiments, the first biomass component is one selected from the group consisting of: a bio-oil, a bio-polymer, and a fat-soluble pigment. In some embodiments, the first biomass component is a bio-oil.

In some embodiments, the at least one PCM is an alcohol and the contacting further includes contacting the biomass source with a catalyst. In some embodiments, the first biomass component is a fatty acid ester product.

In some embodiments, the contacting and mixing results in extraction of a second biomass component that is extracted into a second phase comprising the co-solvent composition. In some embodiments, the second biomass component is selected from the group consisting of: a protein, a carbohydrate, a nucleic acid, DNA and RNA. In some embodiments, the second biomass component is a protein.

In some embodiments, the method includes removing the first phase from the multiple-phase composition.

In some embodiments, the multiple phase composition includes a first phase comprising the biomass component, a second phase comprising the co-solvent composition, and a third phase comprising the treated biomass. In some embodiments, the method further includes facilitating separation of the multiple phase composition into the first phase comprising the biomass component, the second phase comprising the co-solvent composition, and the third phase comprising the treated biomass. In some embodiments, the facilitating separation of the multiple-phase composition includes centrifuging the multiple phase composition. In some embodiments, the facilitating separation of the multiple-phase composition includes passing the multiple-phase composition through at least one filter.

In some embodiments, where the second biomass component is a protein, the method includes separating the extracted protein from the multiple-phase composition.

In some embodiments, the biomass source is at least one selected from the group of: microalgae, yeast, oil seeds and plant matter.

In some embodiments, the at least one polar covalent molecule (PCM) is selected from the group consisting of: alcohols, ketones, organic acids, alkyl halides, sulfoxides, aldehydes, amides, and amines.

In some embodiments, the at least one ionic liquid is comprised of a cation and anion and that is a liquid salt at room temperature. In some embodiments, the general structure of the cation is one selected from the group consisting of:

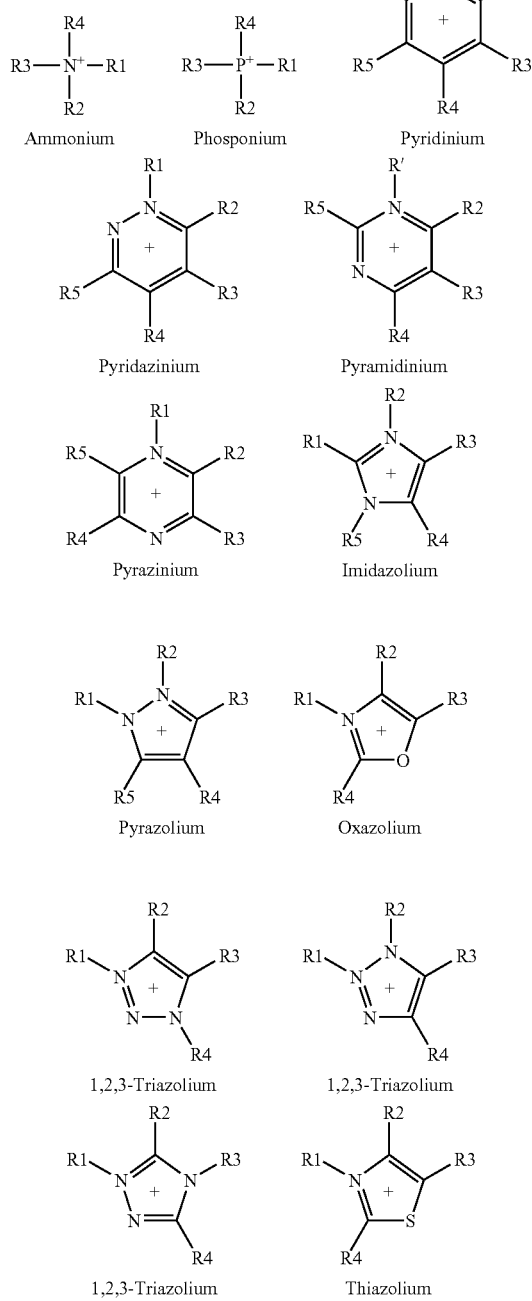

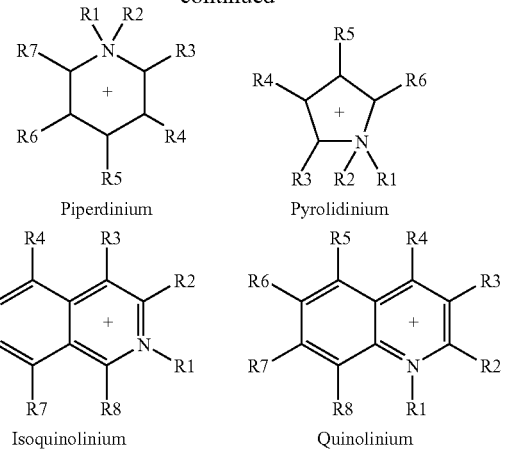

wherein R1 through R6 are independently selected from groups consisting of C0-C6 alkyl, alkenyl, hydroxyalkyl, haloalkyl, alkoxylalkyl, C6-C10 aryl or C8-C16 alkylearyl, or mixtures thereof, wherein C0 denotes hydrogen. In some embodiments, the cation is an imidazolium cation.

In some embodiments, wherein the anion of the at least one ionic liquid is one selected from the group consisting of: a halide, a C1-C6 carboxylate, a mono- or di-C1-C10 alkyl sulfosuccinate, a mono- or di-C1-C10 ester sulfosuccinate, a nitrate, a sulfate, an alkylsulfates, a phosphate, an alkylphosphates, an acetate, a halogenoacetates, a tetrafluoroborate, a tetrachloroborate, a hexafluorophosphate, a trifluoro-tris-(pentafluoroethyl)phosphate, a hexafluoroantimonate, a fluorosulfonate, an alkylsulfonate, a perfluoroalkylsulfonate, a bis(perfluoroalkylsulfonyl)amide, a tris-trifluoromethylsulfonyl methylide with formula $C(CF_3SO_2)_3^-$, a bis-trifluoromethylsulfonyl methylide with formula $HC(CF_3SO_2)_3^-$), an arenesulfonate optionally substituted with halogens or halogenalkyl groups, a tetraphenylborate anion, a tetraphenylborate anion the aromatic rings of which are substituted, a tetra-(trifluoroacetoxy)-borate, a bis-(oxalato)-borate, a dicyanamide, a tricyanomethylide, a tetrachloroaluminate anion, and a chlorozincate anion, or mixtures thereof. In some embodiments, the anion is a methyl sulfate anion.

In some embodiments, the at least one ionic liquid is selected from the group consisting of: 1-ethyl-3-methylimidazolium methyl sulfate, 1-methylimidazolium tetrafluoroborate, 1-alkyl-3-methylimidazolium hydrogensulfonates, 1-butylpyridinium chloride/aluminum chloride, 1-octyl-3-methylimidazolium tetrafluoroborate (OMIM/BF$_4$), [EMIM][BF$_4$], [BMIM][BF$_4$], [HMIM][BF$_4$], [BMIM][HSO$_4^-$], [BP]Cl[BF$_4$], a di-alkylimidaxolium salt, a quaternary ammonium salt, and mixtures thereof. In some embodiments, the at least one ionic liquid is 1-ethyl-3-methyl imidazolium methyl sulfate.

In some embodiments, the ratio of the total amount of ionic liquid to the total amount of polar covalent molecule in the co-solvent composition can be varied from 10:1 (w/w) to 1:1 (w/w).

In some embodiments, the ratio of the biomass to co-solvent composition is at most 250 milligrams biomass per gram of co-solvent composition.

Embodiments of the invention also relate to a method of separating a bio-oil from a biomass source, the method including: contacting a co-solvent composition with the biomass source, wherein the co-solvent composition comprises at least one polar covalent molecule (PCM) and at least one ionic liquid; and mixing the co-solvent composition and the biomass source, wherein said contacting and mixing results in extraction of a bio-oil and formation of a multiple-phase composition, wherein a first phase comprises the separated bio-oil.

In embodiments of the invention, a method of direct transesterification of a biomass source is provided, the method including: contacting the biomass source with a co-solvent composition and a catalyst, wherein the co-solvent composition comprises at least one ionic liquid and at least one polar covalent molecule (PCM); and mixing the co-solvent composition, catalyst and the biomass source, wherein said contacting and mixing results in formation of a fatty acid ester product and a multiple-phase composition, wherein a first phase comprises the fatty acid ester product.

In some embodiments, the method includes removing the first phase comprising the fatty acid ester product from the multiple-phase composition In some embodiments, the multiple-phase composition includes the first comprising the fatty acid ester product, a second phase comprising the co-solvent composition, and a third phase comprising the treated biomass.

In some embodiments, the method includes facilitating separation of the multiple phase composition into the first phase including the fatty acid ester, a second phase including the co-solvent composition, and a third phase including the treated biomass. In some embodiments, the facilitating separation of the multiple phase composition includes centrifuging the multiple phase composition. In some embodiments, the facilitating separation of the multiple phase composition includes passing the multiple phase composition through at least one filter.

In some embodiments, the contacting and mixing results in extraction of a protein from the biomass source into the second phase comprising the co-solvent composition. In some embodiments, the method includes separating the extracted protein from the multiple-phase composition.

In some embodiments, the biomass source is at least one selected from the group of: microalgae, yeast, oil seeds and plant matter.

In some embodiments, the at least one polar covalent molecule (PCM) is an alcohol having at least one methyl group. In some embodiments, the at least one polar covalent molecule (PCM) is a hydrocarbon derivative having an —OH group attached to a carbon atom that is not in an aromatic ring.

In some embodiments, the at least one ionic liquid includes a cation and anion and is a liquid salt at room temperature. In some embodiments, the at least one ionic liquid is selected from the group consisting of: 1-ethyl-3-methylimidazolium methyl sulfate, 1-methylimidazolium tetrafluoroborate, 1-alkyl-3-methylimidazolium hydrogensulfonates, 1-butylpyridinium chloride/aluminum chloride, 1-octyl-3-methylimidazolium tetrafluoroborate (OMIM/BF$_4$), [EMIM][BF$_4$], [BMIM][BF$_4$], [HMIM][BF$_4$], [BMIM][HSO$_4^-$], [BP]Cl[BF$_4$], a di-alkylimidaxolium salt, a quaternary ammonium salt, and mixtures thereof. In some embodiments, the at least one ionic liquid is 1-ethyl-3-methyl imidazolium methyl sulfate.

In some embodiments, the ratio of the total amount of ionic liquid to the total amount of polar covalent molecule in the co-solvent composition can be varied from 10:1 (w/w) to 1:1 (w/w).

In some embodiments, the ratio of the biomass to co-solvent composition is at most 250 milligrams biomass per gram of co-solvent composition.

Embodiments of the invention also relate to methods of extracting lipids as bio-oil or fatty acid ester product, biopolymers, fat soluble pigments and/or protein from a biomass source that include contacting the biomass source with at least one polar covalent molecule (PCM) and at least one ionic liquid (IL) (together referred to herein as a "co-solvent composition") to form an extraction mixture. The lipids can include, but are not limited to, a bio-oil or a fatty acid ester product (such as, for example, a fatty acid methyl ester). The at least one polar covalent molecule and at least one ionic liquid can be provided in varying proportions to each other. In some embodiments, contacting the biomass source with a co-solvent composition produces a three phase product that includes: a bio-oil partitioned into a top phase that is immiscible from the extraction mixture, a protein extract that is dissolved into the co-solvent composition phase, and a solid biomass phase largely absent of lipid and protein.

In some embodiments, the at least one polar covalent molecule comprises an alcohol. In some embodiments, the at least one polar covalent molecule is an alcohol having at least one methyl group. In some embodiments, the at least one polar covalent molecule is selected from the group consisting of: methanol, ethanol, propanol, butanol, pentanol, hexanol, heptanol, octanol, nonanol, decanol, and the like. In other embodiments the at least one polar covalent molecule is from another solvent class such as a ketone, an aldehyde, or any such molecule that contains both hydrophobic and hydrophilic regions separated by a covalent bond, and at least one functional group. The hydrophobic end can be as simple as a methyl group or a larger alkane chain. The hydrophilic end can be comprised of a chemically active functional group such as, for example, a carboxyl, ketone, aldehyde, amine, or a hydroxide.

The at least one ionic liquid is comprised of a mixture of a cation and an anion. In some embodiments, the cation can be, but is not limited to, 1-Ethyl-3-methylimidazolim, 1-Butyl-2,3-dimethylimidazolium, 1-Ethyl-2,3-dimethylimidazolium, 1-Hexyl-3-methylimidazolium, 1-Allyl-3-methylimidazolium chloride, 1-Butyl-3-methylpyridinium, -Allyl-3-methylimidazolium chloride, 1-Butyl-3-methylpyridinium, 1-Butyl-4-methylpyridinium, 1-Ethyl-3-methylpyridinium, 1-Ethyl-3-hydroxymethylpyridinium. The anion can be, but is not limited to hydrogen sulfate, dihydrogen sulfate, methyl sulfate, chloride, bromide, tetrafluoroborate, dicyanamide, trifluoromethanesulfonate, methanesulfonate, bis(trifluoromethylsulfonyl)imid, tosylate), bis(trifluoromethylsulfonyl)imid, chloride, bromide, tetrafluoroborate, hexafluorophosphate, chloride, dihydrogen sulfate, ethylsulfate, nonaflate, bis(trifluoromethylsulfonyl)imide), triethylammonium hydrogen sulfate, trioctyl ammonium hydrogen sulfate, tris(perfluoroalkyl)trifluorophosphate (FAP), and the like.

In some embodiments, the invention relates to the direct making and extraction of a fatty acid ester product, comprising: contacting a biomass source with at least one ionic liquid and at least one alcohol (together referred to herein as the "co-solvent composition"), and a catalyst to form a reaction mixture, wherein the fatty acid ester product is partitioned to a separate immiscible phase as it is produced, a protein extract that is dissolved into the co-solvent composition, and a solid biomass phase that is largely absent of lipid and protein In some embodiments of the invention, the method further comprises separating the reacted biomass from the reaction mixture through techniques such as mechanical filtration or centrifugation or using standard techniques known in the art.

In some embodiments, the co-solvent composition described herein is applied to dry biomass. In some embodiments of the invention, the co-solvent composition described herein can be applied to wet biomass.

In some embodiments of the invention, the catalyst can be, but is not limited to, potassium hydroxide, sodium hydroxide, sodium methoxide, sodium ethoxide, quanidines (1,5,7-trizabicyclo[4.4.0]dec-5-ene), diethylamine, dimethylethanol amine, tetramethyldiaminoethane, tetramethylammonium hydroxide, dihydrogen sulfate, sulfuric acid, acetyl chloride, hydrochloric acid, lipase enzymes, and the like.

In some embodiments of the invention, the biomass comprises, for example, but not limited to, microalgae cells, yeast cells, oil seed crops (including, for example, but not limited to, grape, rapeseed, canola, soybean, safflower, jatropa, radis), agricultural wastes (including, for example, but not limited to, tallow and fats from slaughter houses), whole plants, seaweeds (including, for example, but not limited to, *Laminaria* sp., *Undaria pinnatifida, Hizikia fusiforme* and *Porphyra* sp), halophytes (including, for example, but not limited to *Salicornia bigelovii*), and the like.

BRIEF DESCRIPTION OF THE DRAWINGS

Those of skill in the art will understand that the drawings, described below, are for illustrative purposes only. The drawings are not intended to limit the scope of the present teachings in any way.

FIG. 20 is a table providing a list of polar covalent molecules in order of decreasing polarity.

DETAILED DESCRIPTION OF THE INVENTION

Figure 1:
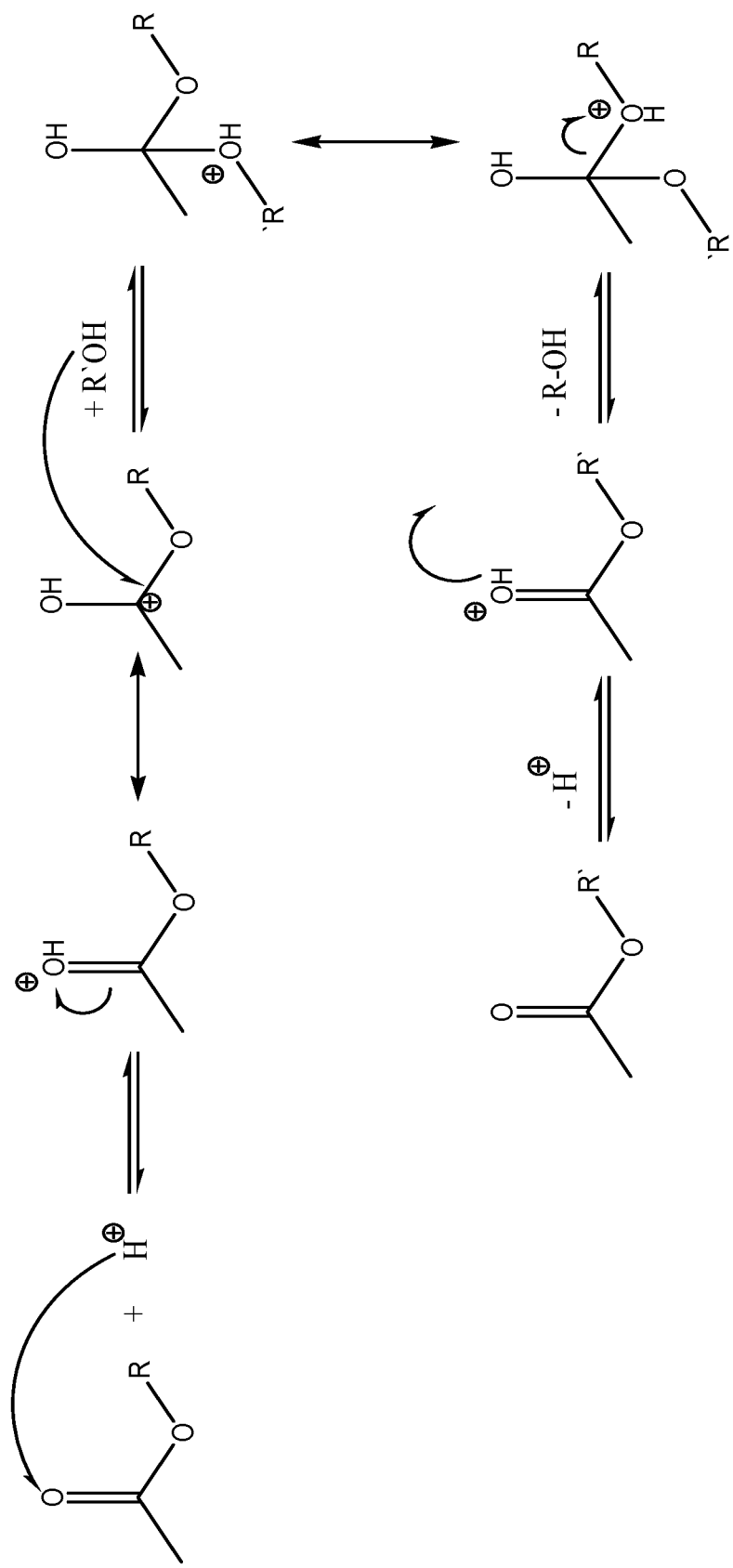
FIG. 1 is a diagram illustrating the mechanism of an acid-catalyzed transesterification reaction.

Embodiments of the invention relate to methods and compositions for carrying out energetically feasible methods for solvent-based extraction, recovery and/or production of a bio-oil or a fatty acid ester product from a variety of biomass starting materials. Embodiments of the invention also relate to methods and compositions for solvent-based extraction of a lipid, a biopolymer, a fat soluble pigment, and/or a protein or any combination thereof from the biomass starting material.

As used herein, the term "co-solvent composition" refers to a composition containing at least one polar covalent molecule (PCM) and at least one ionic liquid. Thus, in some embodiments, the co-solvent composition can contain more than one PCM. For example, the co-solvent composition can contain two, three, four, five or more PCMs. In some embodiments, the co-solvent composition can contain more than one ionic liquid. For example, the co-solvent composition can contain two, three, four, five or more ionic liquids. In some embodiments, the components of the co-solvent composition can be combined together before being provided as a co-solvent composition in the methods disclosed herein. In some embodiments, the components of the co-solvent composition can be individually provided, thereby assuming the properties of the co-solvent composition after both components are added to a mixture formed in the methods disclosed herein.

As used herein, the term "co-solvent system" is a system that comprises a co-solvent composition containing at least one polar covalent molecule (PCM) and at least one ionic liquid. The co-solvent system can be contacted with a biomass source to separate bio-oils, bio-polymers, fatty acid ester products and/or proteins from the biomass source. For example, a biomass source can be contacted with the co-solvent system for the separation of a bio-oil or bio-polymer from the biomass, wherein said contacting results in extraction of the bio-oil or bio-polymer and formation of a multiple-phase composition in which the extracted bio-oil or bio-polymer is found in a distinct phase. In some embodiments, a biomass source can be contacted with the co-solvent system for extraction of a protein from a biomass source, wherein said contacting results in extraction of the protein into a phase that also contains the co-solvent composition. In some embodiments, the system can used for direct transesterification of a biomass source to produce a fatty acid ester product. In some embodiments, the co-solvent system is synonymous with the co-solvent composition.

As used herein, the term "extraction mixture" refers to a mixture containing a co-solvent composition substantially as described herein and a biomass source. The co-solvent composition and biomass source can be added to form the extraction mixture in any sequence or in any combination. In some embodiments, the extraction mixture is formed by adding the co-solvent composition to the biomass. In some embodiments, the extraction mixture is formed by adding the biomass source to the co-solvent composition. In some embodiments, the extraction mixture is formed by adding the co-solvent composition and the biomass source simultaneously. In some embodiments, the components of the co-solvent composition are provided individually to the extraction mixture, thereby assuming the properties of the co-solvent composition within the extraction mixture.

As used herein, the term "reaction mixture" refers to a mixture containing a co-solvent composition substantially as described herein, a biomass source and at least one catalyst. The co-solvent composition, biomass source and catalyst can be added to form the reaction mixture in any sequence or in any combination. In some embodiments, the reaction mixture is formed by adding the co-solvent composition prior to adding the biomass source and/or the catalyst. In some embodiments, the reaction mixture is formed by adding the biomass source prior to adding the co-solvent composition and/or the catalyst. In some embodiments, the reaction mixture is formed by adding the at least one catalyst to the reaction mixture prior to adding the co-solvent composition and/or the biomass source. In some embodiments, the reaction mixture is formed by combining the co-solvent composition and the biomass source prior to addition of the at least one catalyst. In some embodiments, the reaction mixture is formed by combining the co-solvent composition and the catalyst prior to addition of the biomass source. In some embodiments, the reaction mixture is formed by combining the biomass source and the catalyst prior to addition of the co-solvent composition. In some embodiments, the reaction mixture is formed by adding the co-solvent composition, the biomass source and the catalyst simultaneously to the reaction mixture. In some embodiments, the components of the co-solvent composition are provided individually, thereby assuming the properties of the co-solvent composition within the reaction mixture.

As used herein, the term "multiple-phase composition" refers to a composition that is formed upon contact of the components of the extraction mixture or the reaction mixture, thereby forming at least two separate phases.

As used herein, the term "substantially pure" refers to a composition or phase that is at least about 75% pure for a single component. For example, a substantially pure composition or phase can be one that is at least about 75%, 75%, 77%, 78%, 79%, 80%, 81%, 82%, 83%, 84%, 85%, 85%, 87%, 88%, 89% or 90% pure for a single component. Preferably, a substantially pure composition or phase is one that is at least about 90%, 91%, 92%, 93%, 94%, 95%, 96%, 97%, 98% or 99% pure for a single component. In some embodiments, a substantially pure composition is one that is 100% pure for a single component.

As used herein, the term "treated biomass" refers to a biomass source that has been contacted with a co-solvent composition or co-solvent system. In some embodiments, the treated biomass is one that has undergone extraction by being contacted with the co-solvent composition or co-solvent system, as herein described. In some embodiments, the treated biomass is one that has undergone direct transesterification as herein described. In some embodiments, the treated biomass is one that has been processed by undergoing extraction or direct transesterification as herein described. In some embodiments, the treated biomass is synonymous with "spent" or "digested" biomass, as understood by one of ordinary skill in the art.

As used herein, the term "mixing" refers to the facilitation of contact between a biomass source and at least one of a co-solvent composition, a co-solvent system, or a catalyst as described herein. In some embodiments, "mixing" refers to the *any means sufficient to facilitate or enhance contact between a biomass source and at least one of a co-solvent composition, a co-solvent system, or a catalyst in an extraction or direct transesterification process as described herein. In some preferred embodiments, the mixing is conducted by mechanically mixing or agitation using techniques known in the art.

In embodiments of the invention, a method to extract any biomass component that is immiscible with a co-solvent composition is provided, the method including: contacting a co-solvent composition with a biomass source, wherein the co-solvent composition comprises at least one polar covalent molecule (PCM) and at least one ionic liquid; and mixing the co-solvent composition and the biomass source, wherein the contacting and mixing of the co-solvent composition and the biomass source results in extraction of the biomass component and formation of a multiple-phase composition, wherein a first phase contains the extracted bio-mass component. In some embodiments, the contacting and mixing results in partitioning of the extracted biomass component into a substantially pure first phase In embodiments of the invention, a method to separate a bio-oil from a biomass source is provided, the method including contacting a co-solvent composition with the biomass source, wherein the co-solvent composition comprises at least one polar covalent molecule (PCM) and at least one ionic liquid; mixing the co-solvent composition and the biomass source; and mixing or otherwise facilitating contact between the co-solvent composition and the biomass source, wherein said contacting results in extraction of a bio-oil and formation of a multiple-phase composition, wherein a first phase comprises the separated bio-oil. In some embodiments, the first phase is a substantially pure phase containing the separated bio-oil. The multiple phase composition can include a second phase comprising the co-solvent composition and the treated biomass.

In some embodiments, the method further includes removing the first phase containing the separated bio-oil from the multiple-phase composition. In some embodiments, the first phase containing the separated bio-oil is optionally subjected to additional processes to further separate or purify the bio-oil from any non-bio-oil components in the first phase. The additional separation processes can include, but are not limited to, centrifugation, filtration (such as, for example, being passed through at least one filter), extraction, and the like.

In some embodiments, the method includes centrifuging the multiple phase composition, thereby further separating the multiple phase composition into the first phase containing the bio-oil, a second phase containing the co-solvent composition, and a third phase containing the treated biomass.

In some embodiments, contacting the co-solvent composition and the biomass source results in extraction of a protein from the biomass source into the phase comprising the co-solvent composition. Preferably, the method includes mixing the co-solvent composition and biomass source to facilitate contact. In some embodiments, the method includes separating the extracted protein from non-protein components in the second phase containing the co-solvent composition.

In some embodiments, contacting the co-solvent composition and the biomass source results in extraction of a fat-soluble pigment from the biomass source into the first phase comprising the bio-oil. Preferably, the method includes mixing the co-solvent composition and biomass source to facilitate contact.

In some embodiments, the method optionally includes contacting the first phase containing the separated bio-oil with a non-polar organic solvent, thereby extracting the bio-oil product into the non-polar organic solvent; and separating the bio-oil product from the non-polar organic solvent.

In some embodiments, the bio-oil is a bio-lipid that is suitable for biodiesel production. In some embodiments, the bio-oil is a bio-lipid that has pharmaceutical or nutraceutical value.

In embodiments of the invention, a method to extract a protein from a biomass source is provided, the method including contacting a co-solvent composition with the biomass source to form an extraction mixture, wherein the co-solvent composition comprises at least one polar covalent molecule (PCM) and at least one ionic liquid; mixing the co-solvent composition and the biomass source to facilitate contact, wherein said contacting and mixing results in extraction of a protein and formation of a multiple-phase composition, wherein a first phase comprises the extracted protein. In some embodiments, the first phase also contains the co-solvent composition.

In some embodiments, the method includes separating the extracted protein from the multiple-phase composition. In some embodiments, the method includes separating the phase containing the extracted protein from the multiple-phase composition. In some embodiments, the method further includes purifying the extracted protein from non-protein components. The further separation of extracted protein from either the multiple phase composition or from non-protein components can be conducted by, for example, precipitation of the protein, affinity chromatography, or any other standard protocols for separation of proteins.

In some embodiments, the method optionally includes contacting the phase containing the extracted protein with an organic solvent, thereby extracting the protein into the organic solvent. In some embodiments, the organic solvent is a non-polar organic solvent. In some embodiments, the organic solvent is a polar organic solvent.

In some embodiments, the contacting and mixing of the co-solvent composition and the biomass source results in extraction of a bio-oil that is included in a second phase of the multiple-phase composition. In some embodiments, the second phase containing the bio-oil is separated from the multiple-phase composition. In some embodiments, the extracted bio-oil is separated from non-bio-oil components in the second phase. Methods to separate the second phase containing the bio-oil or to separate the extracted bio-oil from non-bio-oil components in the second phase are described herein.

In some embodiments, the contacting and mixing of the co-solvent composition and the biomass source results in extraction of a fat-soluble pigment from the biomass source into the second phase comprising the bio-oil.

In embodiments of the invention, a method to extract a bio-polymer from a biomass source is provided, the method including contacting a co-solvent composition with the biomass source to form an extraction mixture, wherein the co-solvent composition comprises at least one polar covalent molecule (PCM) and at least one ionic liquid; mixing the extraction mixture to facilitate contact between the co-solvent composition and the biomass source, wherein the contacting and mixing results in extraction of a bio-polymer and formation of a multiple-phase composition, wherein a first phase contains the bio-polymer.

In some embodiments, the method includes separating the first phase containing the bio-polymer from the multiple-phase composition.

In some embodiments, the method optionally includes contacting the first phase containing the extracted bio-polymer with an organic solvent, thereby extracting the bio-polymer into the organic solvent. In some embodiments, the organic solvent is a non-polar organic solvent. In some embodiments, the organic solvent is a polar organic solvent.

In some embodiments, the contacting and mixing of the co-solvent composition and the biomass source results in extraction of a bio-oil that is included in a second phase of the multiple-phase composition. In some embodiments, the second phase containing the bio-oil is separated from the multiple-phase composition. In some embodiments, the extracted bio-oil is separated from non-bio-oil components in the second phase. Methods to separate the second phase containing the bio-oil or to separate the extracted bio-oil from non-bio-oil components in the second phase are described herein.

In some embodiments, the contacting and mixing of the co-solvent composition and the biomass source results in extraction of a protein from the biomass source into a third phase comprising the co-solvent composition. In some embodiments, the method includes separating the extracted protein from non-protein components in the third phase containing the co-solvent composition. In some embodiments, the method includes separating the extracted protein from the multiple-phase composition. The separation of extracted protein from either the multiple phase composition or from non-protein components in the first phase can be conducted by, for example, precipitation of the protein, affinity chromatography, or any other standard protocols for separation of proteins.

In some embodiments, the contacting and mixing of the co-solvent composition and the biomass source results in extraction of a fat-soluble pigment from the biomass source into the second phase comprising the bio-oil.

In embodiments of the invention, a method of producing a fatty acid ester product from a biomass source is provided, the method including: contacting a biomass source with a co-solvent composition and a catalyst, wherein the co-solvent composition comprises at least one ionic liquid and at least one polar covalent molecule (PCM); mixing the co-solvent composition, catalyst and the biomass source, wherein said contacting and mixing results in formation of a fatty acid ester product and a multiple-phase composition, wherein a first phase includes the fatty acid ester product.

Embodiments of the invention also relate to a method of direct transesterification of a biomass source, comprising: contacting a biomass source with a co-solvent composition and a catalyst to form a reaction mixture, wherein the co-solvent composition comprises at least one ionic liquid and at least one polar covalent molecule (PCM); mixing the co-solvent composition, catalyst and the biomass source, wherein said contacting and mixing results in formation of a fatty acid ester product and a multiple-phase composition, wherein a first phase includes the fatty acid ester product.

Embodiments of the invention also relate to a method of producing a bio-fuel, comprising: contacting a biomass source with a co-solvent composition and a catalyst to form a reaction mixture, wherein the co-solvent composition comprises at least one ionic liquid and at least one polar covalent molecule (PCM); mixing the co-solvent composition, catalyst and the biomass source, wherein said contacting and mixing results in formation of a fatty acid ester product and a multiple-phase composition, wherein a first phase includes the fatty acid ester product.

In some embodiments, the method includes removing the first phase containing the fatty acid ester product from the multiple-phase composition. In some embodiments, the first phase containing the fatty acid ester product is subjected to additional separation processes to separate the fatty acid ester product from other non-fatty acid ester components in the first phase. The additional separation processes can include, but are not limited to, centrifugation, filtration (such as, for example, being passed through at least one filter), extraction, and the like.

In some embodiments, the method includes centrifuging the multiple phase composition, thereby further separating the multiple phase composition into the first phase containing the fatty acid ester product, a second phase containing the co-solvent composition, and a third phase containing the treated biomass.

In some embodiments, the contacting and mixing of the co-solvent composition and the biomass source results in extraction of a protein from the biomass source into a second phase comprising the co-solvent composition. In some embodiments, the method includes separating the extracted protein from non-protein components in the second phase containing the co-solvent composition. In some embodiments, the method includes separating the extracted protein from the multiple-phase composition. The separation of extracted protein from either the multiple phase composition or from non-protein components in the second phase can be conducted by, for example, precipitation of the protein, affinity chromatography, or any other standard protocols for separation of proteins.

In some embodiments, the contacting and mixing of the co-solvent composition and the biomass source results in extraction of a fat-soluble pigment from the biomass source into the first phase comprising the fatty acid ester product.

In some embodiments, the method optionally includes contacting the first phase containing the fatty acid ester product with a non-polar organic solvent, thereby extracting the fatty acid ester product into the non-polar organic solvent; and separating the fatty acid ester product from the non-polar organic solvent.

Polar Covalent Molecules (PCMs)

In embodiments of the invention, the concentration or choice of the polar covalent molecule(s) (PCM) can be varied in the co-solvent composition or co-solvent system. The mass ratio of total PCM to total ionic liquid (IL) in the co-solvent composition or co-solvent system can be about 1:1000, 1:500, 1:100, 1:50, 1:10, 1:5, or 1:1. In some embodiments, the ratio of total PCM to total IL in the co-solvent composition or co-solvent system can range from about 1:1 (w/w) to about 1:50 (1/1), including any ratio within the range. For example, the ratio of total PCM to total IL can be about 1:1 (w/w), 1:3 (w/w), 1:5 (w/w), 1:8 (w/w), 1:10 (w/w), 1:15 (w/w), 1:20 (w/w), 1:25 (w/w), 1:30 (w/w), 1:35 (w/w), 1:40 (w/w), 1:45 (w/w) or 1:50 (w/w).

In some embodiments, the at least one PCM can be any molecule selected from the group consisting of: a sulfoxide, a carboxylic acid, an amide, an alcohol, a ketone, an alkyl halide, an ester, and an amine. Typical PCMs that can be used in embodiments of the invention include, but are not limited to, dimethyl sulfoxide (DMSO), acetic acid, acetamide, methanol, ethanol, isopropanol, acetone, chloroform, isopropanol, methyl acetate, propylamine and methyl chloroform. In some preferred embodiments, the at least one PCM is an alcohol having at least one methyl group. For example, the at least one PCM can be methanol, ethanol, propanol, butanol, pentanol, hexanol, heptanol, octanol, nonanol, decanol and the like, or mixtures thereof. In some embodiments, the at least one PCM is a hydrocarbon derivative that contains an —OH group attached to a carbon atom that is not an aromatic ring.

Ionic Liquids

An ionic liquid (IL) is a mixture of cations and anions (e.g., a salt), in which a cation or anion is much larger than its corresponding oppositely-charged ion in the mixture (Seddon, K. R., 1997. "Ionic liquids for clean technology." *Journal of Chemical Technology and Biotechnology.* 68:351-356, which is incorporated herein by reference in its entirety). The size discrepancy between the cation and anion inhibits the formation of ion lattices and therefore permits these ionic mixtures to remain in liquid form at low temperatures. Although ionic liquids are generally formed from a homogeneous substance comprising one species of cation and one species of anion, IL solutions can be composed of more than one species of cation and/or anion.

Ionic liquids possess attractive processing characteristics such as the ability to adjust their viscosity as a function of operating temperature or a cation R group, the ability to adjust their polarity as a function of the choice of cation and/or an R group, and the ability to adjust their relative hydrophobicity (i.e. miscibility with water) by choice of the anion. The use of a polar and hydrophilic ionic liquid can, for example, facilitate the solubilization of the polar covalent molecule and, in the case of direct transesterification, facilitate the solubilization of the acid or base catalyst and the separation of a fatty acid ester product from the co-solvent composition. For example, ionic liquids have a significant capacity to solvate catalysts and substrates whilst partitioning the end products into a separate phase (Neto, B. A. D., et al. 2007. WO 2006095134, which is incorporated herein by reference in its entirety). By facilitating the separation of the product from the reaction phase, ionic liquids can minimize the loss of the catalyst that typically remains associated with the product. Additional steps that involve neutralization and washing of the fatty acid ester product to recover the catalyst are also eliminated.

Traditional co-solvent compositions containing organic solvents have typically been used in extraction of bio-oils or direct transesterification reactions. However, because separation of the desired products from organic compositions can require multiple steps that are energetically costly and environmentally unfavorable, alternatives to organic solvent components in co-solvent compositions were investigated by the inventors. It has been unexpectedly discovered that, using the co-solvent system described herein, in which ionic liquids are substituted for organic solvents, desirable products resulting from extraction processes or direct transesterification reactions carried out on biomass can be partitioned out of phase with the co-solvent composition. The desirable products include, but are not limited to, bio-oils, fatty acid ester products and/or fat-soluble pigments. It has been unexpectedly found that contacting the co-solvent composition described herein with a biomass source results in a multi-phase composition, whereby the desired products are partitioned, or self-separated, into a distinct phase. This phenomenon of self-separation substantially facilitates removal of the desired products from the multiple-phase composition and eliminates the need for additional, and sometimes costly, steps to separate the desired products from the bio-mass. Because solvents that are immiscible with the desired products typically require further processing steps to separate the products from the solvent, the partitioning, or auto-separation, of the desired products into a distinct phase when using the co-solvent composition as taught herein to conduct extraction or direct transesterification on biomass is a surprising result and represents a significant advancement in the field.

Without wishing to be bound by theory, it is believed that the action of an IL-based co-solvent composition forces the bio-lipid or fatty acid methyl ester out of phase with the co-solvent composition, avoiding limitations related to solvent carrying capacity. The ionic liquid is polar and immiscible with nonpolar molecules such as bio-oils, bio-lipids and fatty acid methyl esters. However, unlike water (which is also polar and immiscible with the target lipid), ionic liquids are not homogeneously polar. This is due to their molecule structure, which include nonpolar as well as polar chemical groups. Consequently, an IL-based co-solvent composition includes regions that are nonpolar and able to both dissolve and solubilize nonpolar molecules such as bio-oils, bio-lipids and fatty acid methyl esters while also possessing extremely strong "self association" ionic bonding forces that dominate the interaction among ionic liquid molecules. The overall effect is that the nonpolar molecules are "moved" through the IL-based co-solvent composition to a surface interface where they partition into their own self-associating and separate immiscible phase. Thus, substitution of an IL-based co-solvent composition for an organic based co-solvent used in traditional organic-based co-solvent compositions can facilitate the separation of a bio-oil product, a bio-lipid or a fatty acid methyl ester from a PCM/IL co-solvent composition.

Additional advantages of ionic liquids include their very low vapor pressures, their wide range of low melting temperatures, and their ability to dissolve a large number of organic and inorganic substances to a greater extent than that of traditional organic solvents (Seddon, K. R., 1997. "Ionic liquids for clean technology." *Journal Chemical Technology and Biotechnology* 68:351-356, which is incorporated herein by reference in its entirety). The low vapor pressure of ionic liquids makes them an environmental friendly alternative to highly volatile organic solvents. An added benefit is that, due to the strong self association between the cation and anion molecules of the ionic liquid, the presence of the ionic liquid can help reduce the vapor pressure of the PCM molecules in the co-solvent composition. For example, the charge-charge interactions between an ionic liquid and methanol, which is a polar molecule that is soluble in ionic liquids, help to reduce the fugacity of the methanol molecules and thus reduce the vapor pressure of methanol.

Furthermore, ionic liquids can be recycled and reused by techniques such as microfiltration, extraction with other solvents, supercritical $CO_2$ extraction, and the like.

Figure 13:
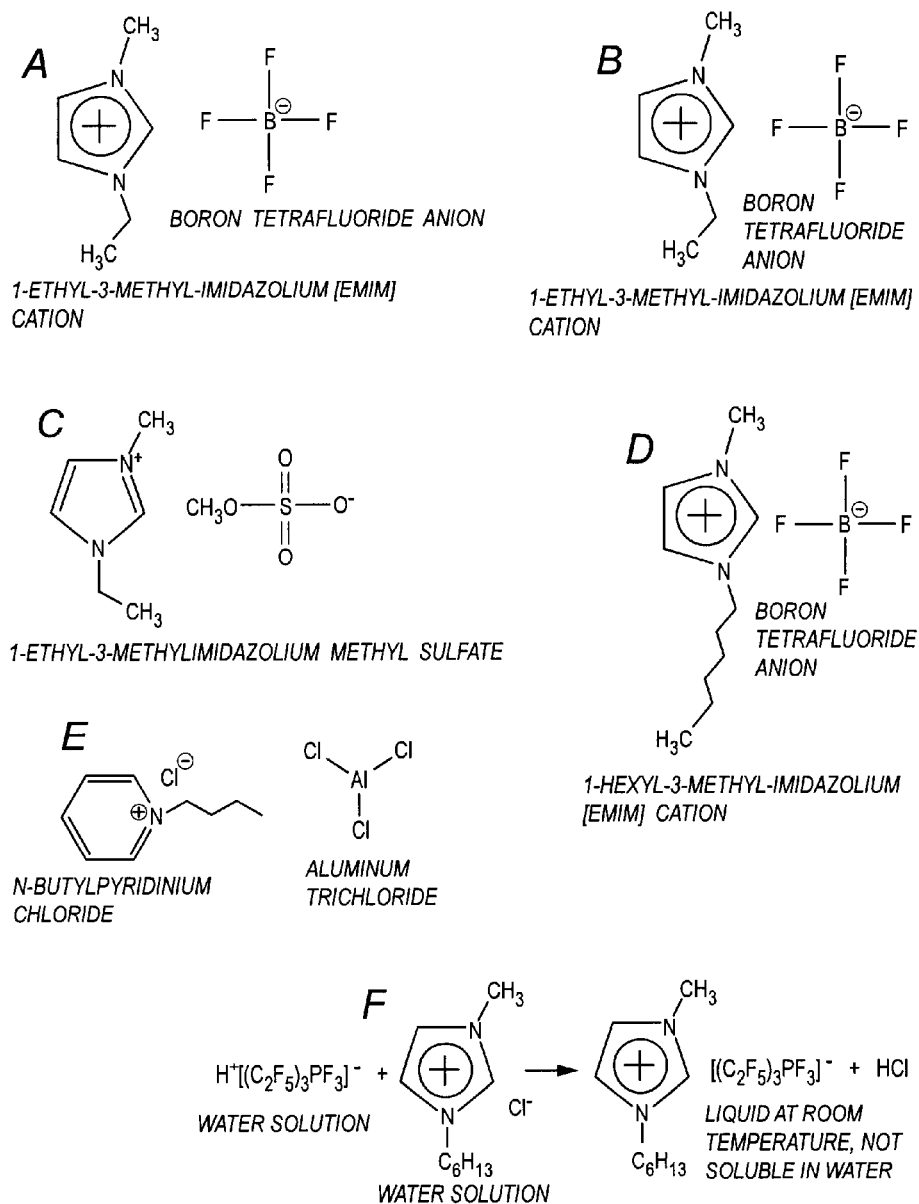
FIG. 13 is a set of chemical structures representing embodiments of ionic liquids used in the reactions described herein.

Exemplary ionic liquid candidates are illustrated in FIG. 13. The polarity of the ionic liquid solutions can be varied by choice of the cation and by chemical manipulation of any of the chemical moities attached to the cations. For example, FIGS. 13A and 13B show two imidazolium cations having a methyl group but different hydrocarbon R2 groups. In addition, the relative hydrophobicity/hydrophilicity of the ionic liquid can be modified by the choice of anion. FIGS. 13A through 13 E illustrate various anions which are relatively polar. FIG. 13F shows a hydrophobic anion (Tris(perfluoroalkyl)trifluorophosphate, also known as "FAP"). Ionic liquids containing FAP anions are immiscible with water (Ignat'ev, N. V., et al. 2005. "New ionic liquids with tris(perfluoroalkyl) trifluorophosphate (FAP) anions." *Journal of Fluorine Chemistry* 126 (8):1150-1159, which is incorporated herein by reference in its entirety). Thus, the ability to vary a cation or an anion in an ionic liquid, including chemical modification of any "R" groups attached to these ions, allow the opportunity to optimize the choice of the ionic liquid for the extraction or transesterification methods disclosed herein. These features, in addition to selecting an appropriate polar covalent molecule with which to produce the IL-based co-solvent, can be adjusted for the desired levels of miscibility (with reactants), immiscibility (with bio-oil or fatty acid ester product), and viscosity (of solution), thus making ionic liquids suitable as "designer" solvents.

In some embodiments, an ionic liquid refers to a molten salt. In other embodiments, an ionic liquid refers to a salt mixture whose melting point is below ambient. These are known as room temperature ionic liquids. Room temperature ionic liquids are a class of ionic liquids with melting points that can range from below temperatures from 50 to 180° C. They are liquid in their pure state at room temperature, possess minimal vapor pressure, and can remain liquid over large temperature ranges, such as, for example, from below ambient temperature (approximately 20° C. to 25° C.) to over 300 to 400° C. Such compositions are mixture of components which are often liquid at temperatures below the individual melting points of the components.

In some embodiments, the ionic liquid solvent is selected from the group formed by liquid salts having the general formula: $Q^+A^-$, in which $Q^+$ represents any cation and $A^-$ represents any anion which can form a liquid salt at low temperatures. Room temperature ionic liquids (ILs) are organic salts, whose cations, substituents, and anions can be varied to change the chemical and physical properties of the IL.

In embodiments disclosed herein, the anion $A^-$ can be one selected from the group consisting of: a halide, a C1-C6 carboxylate, a mono- or di-C1-C10 alkyl sulfosuccinate, a mono- or di-C1-C10 ester sulfosuccinate, a nitrate, a sulfate, an alkylsulfates, a phosphate, an alkylphosphates, an acetate, a halogenoacetates, a tetrafluoroborate, a tetrachloroborate, a hexafluorophosphate, a trifluoro-tris-(pentafluoroethyl) phosphate, a hexafluoroantimonate, a fluorosulfonate, an alkylsulfonates (such as, for example, methylsulfonate), a perfluoroalkylsulfonate (such as, for example, trifluoromethylsulfonate), a bis(perfluoroalkylsulfonyl)amide (such as, for example, bis-trifluoromethylsulfonyl amide with formula $N(CF_3SO_2)_3^-$, tris-trifluoromethylsulfonyl methylide with formula $C(CF_3SO_2)_3^-$, or bis-trifluoromethylsulfonyl methylide with formula $HC(CF_3SO_2)_3^-$), an arenesulfonate optionally substituted with halogens or halogenalkyl groups, a tetraphenylborate anion, a tetraphenylborate anion the aromatic rings of which are substituted, a tetra-(trifluoroacetoxy)-borate, a bis-(oxalato)-borate, a dicyanamide, a tricyanomethylide, a tetrachloroaluminate anion, and a chlorozincate anion, or mixtures thereof.

In some embodiments, the anion of an IL can act as a Lewis acid such as, for example, $BF_4^-$, $AlCl_3$, or $H_2SO_4^-$.

The cationic component $Q^+$ can have any of the general structures as follows, wherein R1 through R8 are independently selected from the group consisting of: C0-C6 alkyl, alkenyl, hydroxyalkyl, haloalkyl, alkoxyalkyl, C6-C10 aryl, C8-C16 alkylearyl, and any combination thereof. "C0," as described herein, denotes hydrogen:

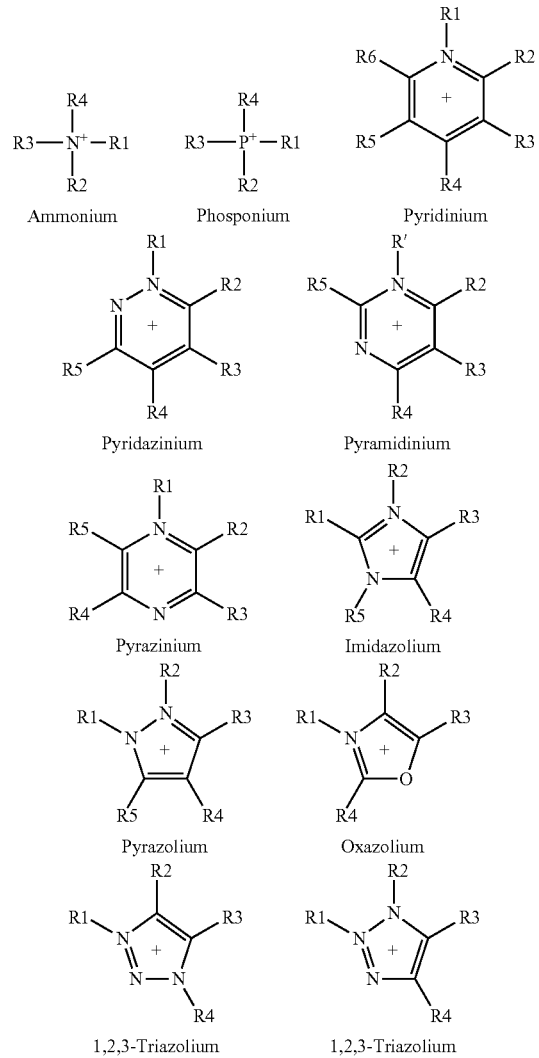

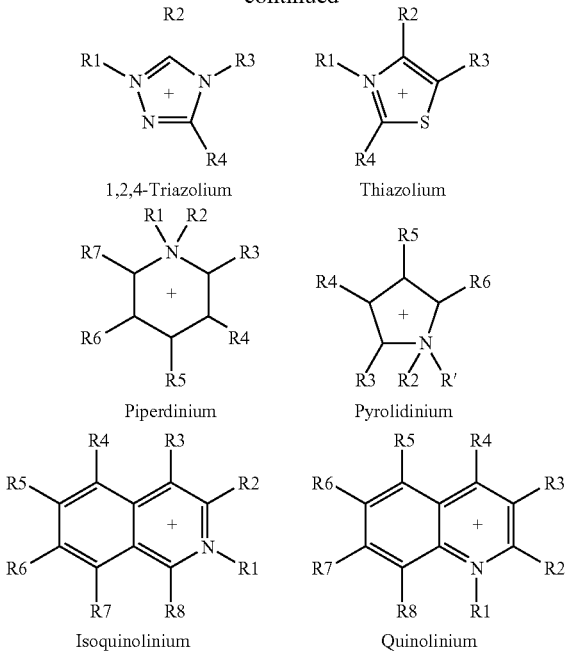

For example, as described, an exemplary cation $Q^+$ can be a quaternary ammonium and/or phosphonium cation having one of general formulae $NR^1R^2R^3R^{4+}$ and $PR^1R^2R^3R^{4+}$ or one of general formulae $R^1R^2N\!=\!\!=\!\!CR^3R^{4+}$ and $R^1R^2P\!=\!\!=\!\!CR^3R^{4+}$ in which $R^1$, $R^2$, $R^3$ and $R^4$, which can be identical or different, and defined as follows. In some embodiments, $R^1$, $R^2$, $R^3$ and $R^4$ can represent hydrogen (except for $NH_4^+$ cation for $NR^1R^2R^3R^{4+}$), a single substituent representing hydrogen, or hydrocarbyl radicals containing 1 to 30 carbon atoms, for example, alkyl groups, saturated or unsaturated, cycloalkyls or aromatics, aryls or aralkyls, which may be substituted, containing 1 to 30 carbon atoms.

In some embodiments, as described herein, the quaternary ammonium and/or phosphonium cations that form an exemplary cation $Q^+$ can also be derived from nitrogen-containing and/or phosphorus-containing heterocycles comprising 1, 2 or 3 nitrogen and/or phosphorus atoms, with general formulae:

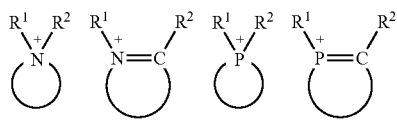

in which the cycles are constituted by 4 to 10 atoms, preferably 5 to 6 atoms, $R^1$ and $R^2$, which can be identical or different, being as defined above.

In some embodiments, the quaternary ammonium or phosphonium cation that form an exemplary cation $Q^+$ can also have one of the following formulae: $R^1R^{2+}N\!=\!\!=\!\!CR^3\!-\!R^{7+}\!-\!R^3C\!=\!\!=\!\!N^+R^1R^{2+}$ and $R^1R^{2+}N\!=\!\!=\!\!CR^3\!-\!R^{7+}\!-\!R^3C\!=\!\!=\!\!N^+R^1R^{2+}$ in which $R^1$, $R^2$, and $R^3$, which can be identical or different, are defined as above, and $R^7$ represents an alkylene or phenylene radical. In some embodiments, $R^1$, $R^2$, $R^3$ and $R^4$ can be, but are not limited to, methyl, ethyl, propyl, isopropyl, primary butyl, secondary butyl, tertiary butyl, amyl, phenyl, benzyl radicals, and the like. $R^7$ can be, for example, a methylene, ethylene, propylene or phenylene group.

In some embodiments, the quaternary ammonium and/or phosphonium cation that form an exemplary cation $Q^+$ is at least one selected from the group formed by N-butylpyridinium, N-ethylpyridinium, pyridinium, 3-ethyl-1-methylimidazolium, 3-butyl-1-methylimidazolium, 3-hexyl-1-methylimidazolium, 3-butyl-1,2-dimethylimidazolium, the 1-(2-hydroxyethyl)-3-methylimidazolium cation, the 1-(2-carboxyethyl)-3-methylimidazolium cation, diethylpyrazolium, N-butyl-N-methylpyrrolidinium, N-butyl-N-methylmorpholinium, trimethylphenylammonium, tetrabutylphosphonium and tributyl-tetradecylphosphonium.

In some embodiments, the exemplary cation $Q^+$ of an IL can be, for example, but not limited to, a substituted imidazolium, quarternary ammonium, tetra alkylphosphonium, pyrrolidinium or pyridinium derivatives. The substituents on the cations (the "R" groups) are typically alkyl chains but can also contain a variety of other functional groups (including, but not limited to, fluoro-alkyl groups, alkenyl groups, methoxy groups, and the like). The anions and cations useful in an IL can be combined in different combinations to yield solvents possessing varied physical and chemical properties (FIG. 13). For example, N-alkylations of the imidazol (or pyridine) system with larger side chains can provide an ionic liquid with more hydrophobic properties. Useful anions and cations can also be chemically modified to alter their physical and chemical properties when included in an ionic liquid. As ionic liquids can be customized by combining different ions of opposite charges, as well as by altering the chemistry of such ions, such solvents are frequently called "designer solvents." Exemplary ionic liquids are illustrated in, but not limited to, those depicted in FIG. 13.

Examples of salts that can be used in embodiments of the invention include, but are not limited to presented in Table 1. These salts may be used alone or as a mixture.

TABLE 1

| | |
|---|---|
| 1-ethyl-3-methylimidazolium methyl sulfate | 1-methylimidazolium tetrafluoroborate |
| 1-alkyl-3-methylimidazolium hydrogensulfonates | 1-butylpyridinium chloride/aluminum chloride |
| 1-octyl-3-methylimidazolium tetrafluoroborate (OMIM/BF$_4$) | 1-ethyl-3-methylimidazolium tetrafluoroborate [EMIM][BF$_4$] |
| 1-butyl-3-methylimidazolium tetrafluoroborate [BMIM][BF$_4$] | 3-methylimidazolium tetrafluoroborate [HMIM][BF$_4$] |
| 1-butyl-3-methylimidazolium hydrogen sulfate [BMIM][HSO$_4^-$] | 3-butyl-1-methylimidazolium bis(trifluoromethylsulfonyl)amide |
| 3-butyl-1,2-dimethylimidazolium bis(trifluoromethylsulfonyl)amide | N-butyl-N-methylpyrrolidinium bis(trifluoromethylsulfonyl)amide |
| 3-butyl-1-methylimidazolium tetrafluoroborate | 3-butyl-1,2-dimethylimidazolium tetrafluoroborate |
| 3-ethyl-1-methylimidazolium tetrafluoroborate | 3-butyl-1-methylimidazolium hexafluoroantimonate |
| 3-butyl-1-methylimidazolium trifluoroacetate | 3-ethyl-1-methylimidazolium triflate |
| 1-(2-hydroxyethyl)-3-methylimidazolium bis(trifluoromethylsulfonyl)amide | 1-(2-carboxyethyl)-3-methylimidazolium bis(trifluoromethylsulfonyl)amide |
| N-butyl-N-methylmorpholinium bis(trifluoromethylsulphonyl)amide | |

In some embodiments, the ionic liquid comprises at least a salt selected from the group of: 1-ethyl-3-methylimidazolium methyl sulfate, 1-methylimidazolium tetrafluoroborate, 1-alkyl-3-methylimidazolium hydrogensulfonates, 1-butylpyridinium chloride/aluminum chloride, 1-octyl-3-methylimidazolium tetrafluoroborate (OMIM/BF4), [EMIM][BF4], [BMIM][BF4], [HMIM][BF4], [BMIM][HSO4-], [BP]Cl[BF4], a di-alkylimidaxolium salt, a quaternary ammonium salt, and the like.

Direct Transesterification

A transesterification reaction involves exchange of an ester group in a compound with another ester group. It is a reaction that can be used to produce a fatty acid ester product (such as, for example, biodiesel) from animal and plant fats and oils (Carvalho, A. P., and F. Xavier Malcata. 2005. "Preparation of fatty Acid Methyl Esters for Gas-Chromatographic Analysis of Marine Lipids: Insight Studies." *Journal of Agricultural and Food Chemistry* 53:5049-5059, which is incorporated herein by reference in its entirety). A transesterification reaction to produce a fatty acid ester product can involve an ester, a catalyst and a derivation alcohol. For example, in reactions where methanol is involved, the catalyzed transesterification of triglycerides with methanol forms glycerol and a fatty acid ester.

Transesterification is also suitable for the derivatization of lipids for analytical characterization. Due to the high boiling points and the thermal instability of natural lipids, transesterification has the advantage of converting the sensitive lipids (free fatty acids and triglycerides) into a fatty acid ester product that can then be separated and characterized by, for example, gas chromatography or nuclear magnetic resonance spectroscopy.

In embodiments of the invention, a transesterification reaction is carried out directly on a biomass source in order to produce a fatty acid ester product. The fatty acid ester product can be, for example, but is not limited to, a fatty acid methyl ester (FAME), a fatty acid ethyl ester, a fatty acid propyl ester, a fatty acid butyl ester, and the like. The fatty acid ester product can be employed directly as biodiesel or undergo further processing to form biodiesel. This reaction, termed "direct transesterification," refers to the in-situ transesterification of triglycerides and free fatty acids directly within a biomass source without their prior extraction and purification. Common applications of direct transesterification have been in the determination of fatty acids and lipids in animal and human tissue, as well as in the determination of fatty acids and lipids in plant or algal feedstock, e.g., seeds, leaves, algal biomass (Lewis, T., Nichols, P. D., and T. A. McMeekin. 2000. "Evaluation of extraction methods for recovery of fatty acids from lipid-producing microheterotrophs." *Journal of Microbial Methods* 43:107-116, which is incorporated herein by reference in its entirety). Compared to a standard transesterification reaction in which biomass lipids are first extracted and purified prior to undergoing transesterification, direct transesterification can provide a more complete conversion of lipids to fatty acid esters without loss of feedstock to side reactions or inefficiencies created during the extraction steps. In addition, it is considered a more environmentally friendly and cost saving alternative to standard transesterification reactions due to the fact that it bypasses the initial solvent extraction step.

Direct transesterification can employ methanol as an alcohol substrate and acetyl chloride as an acid catalyst in methanol-acetyl-chloride volume ratios of 100:5, although other volume ratios can be used. The methanol is typically employed in great excess (relative to the stoichiometric molar ratio of 3:1 for every mole of triglyceride within a cell of biomass source, or 1:1 for every mole of fatty acid in the cell) in order to both drive the reaction in favor of fatty acid methyl ester production as well as to submerge the cell biomass in methanol. As typically applied, such direct transesterification reactions produce fatty acid ester products which require extraction into a nonpolar solvent such as, for example, hexane or a hexane/water mixture (1:1 v/v %). The fatty acid ester product is subsequently separated from the nonpolar solvent by evaporation of the solvent under vacuum.

As described herein, it has been discovered that in the presence of a suitable catalyst, a biomass source can be contacted with a co-solvent composition comprising at least one polar covalent molecule (PCM) and at least one ionic liquid to form a multiple-phase reaction mixture in which a fatty acid ester product, wherein the fatty acid ester product is found in a separate phase from that containing the co-solvent composition and/or the treated biomass. In preferred embodiments of the invention, the PCM is an alcohol. In some preferred embodiments, the PCM is a methyl alcohol. In some preferred embodiments, the PCM is an ethyl alcohol.

In some embodiments, it is preferable to execute the transesterification reaction in a solvent system that is (1) noncorrosive, (2) devoid of emissions (i.e. low vapor pressure), (3) miscible with the alcohol reactant (e.g. methanol) and catalyst or catalysts (e.g. HCl, NaOH), (4) immiscible with the fatty acid ester product, (5) miscible with the any protein that is extracted from the biomass source, and (6) miscible with any glycerol product which can be made immiscible with a glycerol derivative (to permit separation of the glycerol product after the fatty acid ester product has been separated out). Because ionic liquids are solvents with regions of both nonpolar and polar chemistry properties, they are able to solvate the catalyst and alcohol reactant used in the transesterification reaction while remaining immiscible with any nonpolar fatty acid ester product produced by the reaction. The miscibility of the catalyst in the polar IL co-solvent composition minimizes the loss of catalyst because it does not bind to the fatty acid ester product, which typically occurs in traditional organic co-solvent composition systems in which the catalyst and fatty acid ester product are both soluble in the co-solvent composition. Ionic liquids also possess minimal vapor pressure and therefore are more representative of "green" solvents than hexane or methanol. In addition, ionic liquids possess great scope for directed design in terms of their polarity and relative hydrophobicity (i.e. use of an FAP (Tris(perfluoroalkyl)trifluorophosphate) anion can make a polar IL immiscible with water).

Accordingly, in embodiments of the invention, a method to produce a fatty acid ester product from a biomass source is provided, the method including contacting the biomass source with a co-solvent composition containing at least one ionic liquid and at least one PCM, and a suitable catalyst; and mixing the biomass source, co-solvent and catalyst to form a multiple-phase composition having at least one fatty acid ester product, which partitions to a separate immiscible phase. In some embodiments, the method includes separating the at least one fatty acid ester product from the multiple-phase composition.

In some embodiments, the biomass source is pre-treated prior to undergoing direct transesterification. The pre-treatment steps can include, but are not limited to, separation of the biomass from growth media, additional drying of the biomass and physical or mechanical pulverization to increase the surface area of the biomass. Any method known to one of skill in the art can be used to carry out the pre-treatment steps. For example, the biomass source can be separated from growth media by centrifugation, rinsed with deionized water to further remove traces of growth media, dried under vacuum and physically ground prior to undergoing direct transesterification.

The biomass source can be contacted with an IL-based co-solvent composition and a suitable catalyst to form a reaction mixture. The manner in which the biomass, the co-solvent composition and the catalyst are combined to form the reaction mixture can be conducted without regard to the sequence of events by which the biomass source, the co-solvent composition and the catalyst are provided or without regard to how the biomass source, the co-solvent composition and the catalyst are combined together. In some embodiments, the biomass is combined with the co-solvent composition and stirred together while the catalyst is subsequently added. In some embodiments, the biomass is combined with the co-solvent composition, and the combination is cooled while the catalyst is subsequently added. In some embodiments, the catalyst and the co-solvent composition are combined prior to submersion of the biomass within the combined catalyst and co-solvent composition.

Once the reaction mixture is formed, it can be heated while being stirred at temperatures at or below the boiling point of the component in the co-solvent composition with the lowest boiling point. In some embodiments, the reaction mixture can be heated to and incubated at a temperature that is from about 1% to about 100% of the boiling point of the component in the co-solvent composition with the lowest boiling point at pressure (also referred to as "the boiling point of the co-solvent composition"). For example, the reaction mixture can be heated to and incubated at about 5%, 10%, 15%, 20%, 25%, 30%, 35%, 40%, 45%, 50%, 55%, 60%, 65%, 70%, 75%, 80%, 85%, 90%, 95% or 100% of the boiling point of the component in the co-solvent composition with the lowest boiling point. In some embodiments, the reaction mixture is heated to and incubated at between about 45° C. to 80° C. In some embodiments, the reaction mixture is incubated at between about 50° C. to 75° C. In some embodiments, the reaction mixture is incubated at between about 55° C. and 70° C.

In some embodiments, the contact between the biomass source, the co-solvent composition and the catalyst in the reaction mixture can be enhanced through the application of sonication, gentle heating, agitation, pressure, and/or radiation energy (e.g., microwave, infrared) to increase the extraction rate and rate of reaction.

In some embodiments, the reaction can be carried out at temperature and/or pressure values ranging from sub-critical to super-critical values to increase reaction and extraction rates and efficiency.

The duration of the reaction can be between from about 1 hour to about 48 hours or more. In some embodiments, the duration of reaction can be between about 3 hours to about 18 hours. In some embodiments, the duration of reaction can be between about 5 hours to about 12 hours. In preferred embodiments, the duration of reaction is the shortest amount of time to achieve substantially complete reaction, such as about 5, 6, 7, 8, 9, 10, 18, 24, 48 or more hours. A substantially complete reaction is one in which no further increase in amount or concentration of product is obtained. For example, at 95% of the boiling point of the co-solvent composition, the reaction time can be approximately 3 to 5 hours. At 75% of the boiling point of the co-solvent composition, the reaction time can be approximately 9 to 15 hours. At 50% the of the boiling point of the co-solvent composition, the reaction time can be approximately 15 to 25 hours. At room temperatures, the reaction time can be about 48 hours.

After substantial completion of the transesterification reaction, the reaction mixture can be subjected to additional processes to facilitate further separation of the reaction products from each other. For example, the reaction mixture can be centrifuged, and a first layer comprising the fatty acid ester product can then be removed by decanting or pipetting the layer into a separate container. In some embodiments, the fatty acid ester product can be separated by extraction into an organic extraction solvent such as hexane. In the event that organic solvent extraction is employed, the product is separated from the organic solvent by evaporating the solvent from the product under vacuum.

In some embodiments, a protein from the biomass source is also extracted into the layer, or phase, comprising the co-solvent composition. The extracted protein can then be separated from the co-solvent composition phase by standard processing protocols. For example, in some embodiments, the alcohol component of the co-solvent composition can be evaporated from the reaction mixture to facilitate the precipitation of the extracted protein in the IL salt. the precipitated protein can then be removed by filtration (such as, for example, being passed through at least one filter), centrifugation, or the like. Alternatively, in some embodiments, the protein can be fractionated and recovered by the use of column chromatography or the like.

In some embodiments, a fat-soluble pigment is also extracted from the biomass source into the phase comprising the co-solvent composition.

In some embodiments, the reacted biomass can be separated from the remnants of the reaction mixture through physical separation techniques such as centrifugation or mechanical filtration.

In some embodiments, the co-solvent composition is recovered and recycled for use in another reaction or extraction process. Co-solvent composition recovery can be conducted by, for example, centrifugation of the remnant of the reaction mixture to pellet the treated biomass and decanting of the co-solvent composition. In some embodiments, the co-solvent can be recovered by mechanical filtration in which a series of mesh filters with incrementally decreasing pore size are employed.

In some embodiments, the method includes conducting a second reaction with the remnant of the multiple-phase composition to form "ether" derivatives of glycerol. Any glycerol that is produced during the transesterification reaction is found in the phase containing the co-solvent composition. After removal of the phase containing the fatty acid ester product, the remnant of the multiple-phase composition containing the glycerol product can be reacted in the presence of an alkene (such as, for example, isobutylene) to form alkyl ethers of glycerol. Alkyl ethers such as, for example, di-tert-butylglycerols (DTBG) and tri-tert-butylglycerol (TTBG) are valuable as fuel additives.

Direct Transesterification Reaction Conditions

Transesterification is a reversible reaction, thus, excess amounts of substrate alcohol can shift the reaction equilibrium to the right and dramatically speed up the rate of reaction and improve the final yield. In preferred embodiments of the invention, the co-solvent composition used in direct transesterification reactions comprises an ionic liquid and a PCM that is an alcohol.

In some embodiments, the concentration of alcohol in the reaction mixture is a value that is in stoichiometric excess relative to the biomass lipid content that can be transesterified. Thus, in some embodiments, the molar ratio of alcohol to transesterifiable lipid can be at least about 3:1, 5:1, 10:1, 20:1, 25:1, 50:1, 100:1, 200:1, 500:1, 1000:1, 2000:1, 5000:1, 10,000:1, 25,000:1, or 50,000:1. In preferred embodiments, the molar ratio of alcohol to transesterifiable lipid is at least about 1000:1, 2000:1, 5000:1, 10,000:1, 25,000:1, or 50,000:1.

In embodiments of the invention, a direct transesterification reaction is carried out using methanol as a PCM and acetyl-chloride as a catalyst. In some embodiments, the methanol:acetyl-chloride volume ratio can be, for example, but is not limited to, about 200:1, 100:1, 50:1, 25:1, 20:1, 10:1, 5:1, or less. In preferred embodiments, the methanol:acetyl-chloride ratio ranges from about 25:1 to about 10:1.

In embodiments of the invention, a direct transesterification reaction is carried out using methanol as a PCM and hydrochloric acid (HCl) as a catalyst. In some embodiments, the methanol:HCl ratio can be, for example, but is not limited to, about 0.5% (w/w) to about 10% (w/w) In preferred embodiments, the methanol:HCl ratio ranges from about 1 (% w/w) to about 5 (% w/w). As disclosed in the Examples, the acid catalyst is reported as HCl although acetyl chloride was added to the reaction mixture. This is because the acetyl chloride reacts with the methanol to release HCl which is, in fact, the active catalyst that drives the transesterification reaction. In these Examples, acetyl chloride was added but calculations were performed to estimate the conversion of acetyl chloride to HCl (as a w/w %), which is reported.

In some embodiments, a direct transesterification reaction is carried out in reaction mixtures in which the PCM is methanol and the catalyst is sulfuric acid. In some embodiments, the methanol:sulfuric acid volume ratio can be, for example, but is not limited to, 200:1, 100:1, 50:1, 25:1, 20:1, 10:1, or less.

In some embodiments, a direct transesterification reaction is carried out in reaction mixture in which the PCM is methanol and the catalyst is an alkaline catalyst. The alkaline catalyst can be, but is not limited to, sodium hydroxide, potassium hydroxide and the like) in volume amounts ranging from about 0.5% (v/v) to about 10% (v/v). In some embodiments, the alkaline catalyst is provided at volume amounts ranging from about 1% (v/v) to about 3% (v/v).

In some embodiments, a direct transesterification reaction is carried out using a co-solvent composition comprising about 46% (w/w) methanol and about 54% (w/w) ionic liquid.

Figure 2:
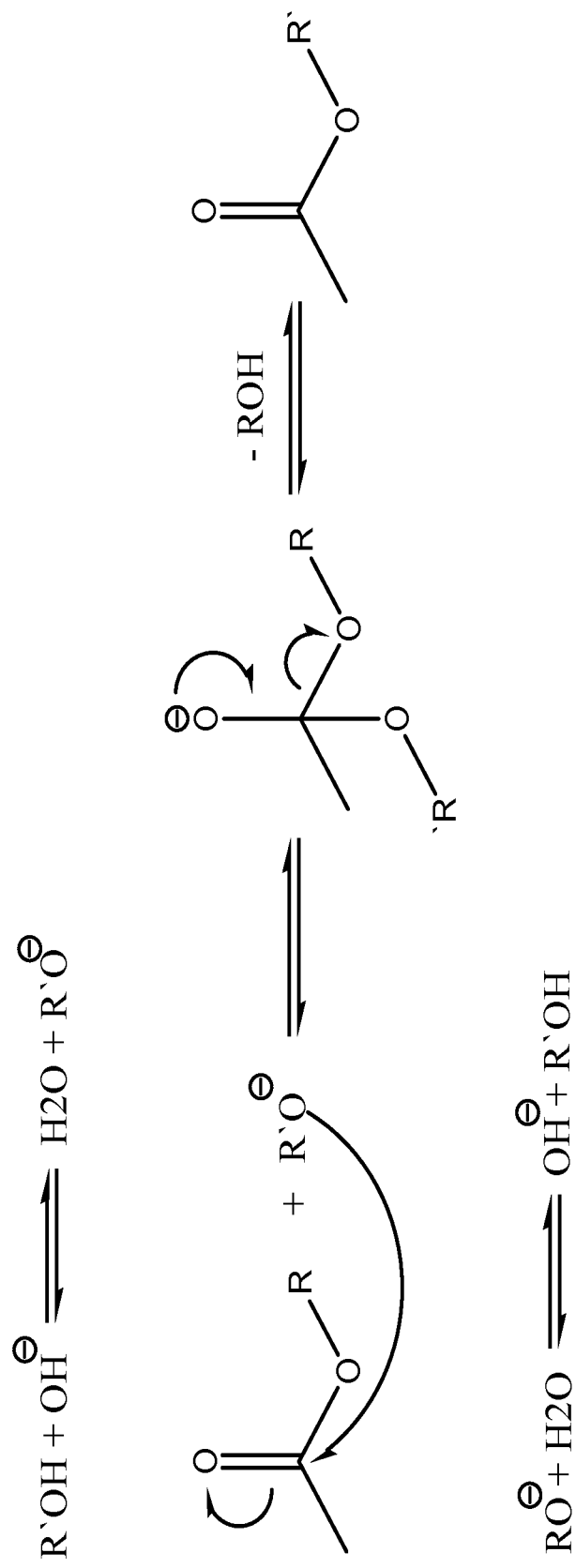
FIG. 2 is a diagram illustrating the mechanism of a base-catalyzed transesterification reaction.

In some embodiments, a direct transesterification reaction can be carried out in a reaction mixture in which the ratio of biomass to co-solvent composition is about 1000 milligrams biomass per gram of co-solvent composition or less. For example, the ratio of biomass to co-solvent composition can be about 1000, 750, 500, 250, 200, 100, 75, 50, 25 or 10 milligrams biomass per gram of co-solvent composition. Preferably, the ratio of biomass to co-solvent composition is at most about 250 milligrams biomass per gram of co-solvent composition Catalysts In embodiments of the invention, the methods and compositions include the presence of a catalyst, which permits the direct transesterification of lipids within a biomass source into a fatty acid ester product that can partition into the separate immiscible phase. In some embodiments, the catalyst is an acidic catalyst. In some embodiments, the catalyst is a basic catalyst. Exemplary catalyzed reactions are described, for example, in Narasimharao et al. (Narasimharao, et al. 2007. "Catalyst in production of biodiesel: A review." *Journal of Biobased Materials and Bioenergy.* 1:19-30, which is incorporated herein by reference in its entirety). Exemplary reaction mechanisms are shown in FIGS. 1 and 2. Acid-catalyzed reactions can involve longer reaction times and require increased temperatures relative to base-catalyzed reactions; however, acid-catalyzed reactions offer an advantage in that fatty acids (if present in the starting material) can also be converted to methyl esters in the same reaction step. If base catalysts are used, residual free fatty acids are transesterified first, with an acid catalyst, before the remaining triglycerides are transesterified (Narasimharao, et al. 2007. supra).

Transesterification reactions typically employ, but are not limited to, MeOH/acid catalysts, MeOH/base catalysts, and the like. However, any combination of alcohol and catalyst can be used. The alcohol can be, for example, methanol, ethanol, propanol, butanol, and the like. The base catalyst can be, for example, KOH, NaOH, NaOCH$_3$, Na$_2$CH$_2$CH$_3$, guanidines (such as, for example, TBD); metal complexes of the type M(3-hydroxy-2-methyl-4-pyrone)2(H2))2 where M=Sn, Zn, Pb, or Hg; liquid amine-based catalysts such as DEA, DMAE, TEMED, or TMAH, and the like. The acid catalyst can be a Bronsted acid that is a sulfonic or sulfuric type acid, H$_2$SO$_4$, HCl, acetyl chloride, BF$_3$, and the like.

In a non-limiting example, acetyl chloride in combination with methanol can be used as a catalyst in a transesterification reaction. The catalytic effect is a two-step reaction in which the acetyl chloride first reacts with methanol to form methyl acetate and gaseous hydrogen chloride which dissolves in the excess methanol. The hydrogen chloride then protonates the carbonyl oxygen of the substrate compound, facilitating the exchange of the ester groups in the substrate.

Heterogeneous acidic and basic catalysts are also useful, such as, for example, solid basic materials including MgO, Al—Mg, hydrotalcites, Cs-exchanged sepiolite, mesoporous MCM-41, heterogenized guanidines on organic polymers, sulfonic ion-exchange resin, WZA, STO, SZA, and Amberlyst-15 with sulfuric acid as catalyst.

Extraction of Bio-Lipids, Bio-Oils, and Fat-Soluble Pigments

The use of ionic liquids, alone or in combination with acid catalysts, has been proposed in transesterification reactions. When used alone, it is hypothesized that the anion of the IL can act as a weak Bronsted acid (WO 2006095134; Zhu, H.-P., et al. 2003. "Bronstead acidic ionic liquid 1-methylimidazolium tetrafluoroborate: A green catalyst and recyclable medium for esterification." *Green Chemistry* 5:38-39, each of the foregoing which is incorporated herein by reference in its entirety). In these approaches, the fatty acid or fatty ester feedstock is extracted and/or purified prior to being added to the ionic liquid for the transesterification reaction. However, as described herein, when applied directly to a biomass source, the anion of the ionic liquid performs poorly as a catalyst. Instead, the use of IL-based co-solvents possessing anions that are weak Bronsted acids is more effective in the extraction of bio-oils (including, but not limited to, bio-lipids) and proteins from the biomass source without the concomitant production of a fatty acid ester product. Accordingly, embodiments of the invention provide methods to extract a bio-oil from a biomass source, the methods including: contacting the biomass source with a co-solvent composition containing at least one ionic liquid and at least one PCM in the absence of an added catalyst; and mixing the biomass source and co-solvent composition, thereby extracting the bio-oil and forming a multiple-phase composition from which the extracted bio-oil partitions into a first separate and immiscible phase. In some embodiments, the method includes separating the extracted bio-oil from the multiple-phase composition. In some embodiments, the bio-oil is a bio-lipid.

A biomass source is typically pre-treated prior to undergoing extraction with the IL-based co-solvent. The pre-treatment steps can include, but are not limited to, separation of the biomass from growth media, additional drying of the biomass and physical or mechanical pulverization to increase the surface area of the biomass. Any method known to one of skill in the art can be used to carry out the pre-treatment steps. For example, the biomass source can be separated from growth media by centrifugation, rinsed with deionized water to further remove traces of growth media, dried under vacuum and physically ground prior to undergoing extraction in the IL-based co-solvent.

The biomass source can be contacted with an IL-based co-solvent composition to form an extraction mixture. The manner in which the biomass and the co-solvent composition are combined to form the extraction mixture can be conducted without regard to the sequence of events by which the biomass source and the co-solvent composition provided or without regard to how the biomass source and the co-solvent composition are combined together. In some embodiments, the biomass is added to the co-solvent composition. In some embodiments, the co-solvent composition is added to the biomass. In some embodiments, the components of the co-solvent composition are added individually to the biomass.

Once the extraction mixture is formed, it can be heated while being stirred at temperatures at or below the boiling point of the component in the co-solvent composition with the lowest boiling point. In some embodiments, the extraction mixture can be heated to and incubated at a temperature that is from about 1% to about 100% of the boiling point of the component in the co-solvent composition with the lowest boiling point at pressure. For example, the extraction mixture can be heated to and incubated at about 5%, 10%, 15%, 20%, 25%, 30%, 35%, 40%, 45%, 50%, 55%, 60%, 65%, 70%, 75%, 80%, 85%, 90%, 95% or 100% of the boiling point of the component in the co-solvent composition with the lowest boiling point. In some embodiments, the extraction mixture is heated to and incubated at between about 45° C. to 80° C. In some embodiments, the extraction mixture is incubated at between about 50° C. to 75° C. In some embodiments, the extraction mixture is incubated at between about 55° C. and 70° C.

In some embodiments, the contact between the biomass source and the co-solvent composition in the extraction mixture can be enhanced through the application of sonication, gentle heating, agitation, pressure, and/or radiation energy (e.g., microwave, infrared) to increase in the rate extraction and rate of reaction.

In some embodiments, the extraction can be conducted at temperature and/or pressure values ranging from sub-critical to super-critical values to increase extraction rates and efficiency.

The duration of the extraction can be between about 1 hour to about 48 hours or more. In some embodiments, the duration of the extraction can be between about 2 hours to about 24 hours. In some embodiments, the duration of the extraction can be between about 3 hours to about 18 hours. In some embodiments, the duration of reaction can be between about 5 hours to about 15 hours. In some embodiments, the duration of reaction can be between about 8 hours to about 12 hours. In preferred embodiments, the duration of extraction is the shortest amount of time to achieve substantially complete extraction, such as about 5, 6, 7, 8, 9, 10, 18, 24, 48 or more hours. A substantially complete extraction is one in which no further increase in amount or concentration of extracted product is obtained.

After extraction is substantially complete, the multiple-phase composition that results can be subjected to additional processes to facilitate further separation of the extracted bio-oils from the multiple-phase composition. For example, the multiple-phase composition can be centrifuged and a first layer comprising the bio-oil can be removed by decanting or pipetting the layer into a separate container. In some embodiments, the bio-oil can be separated to by extraction into an organic solvent such as hexane. In the event that organic solvent extraction is employed, the extracted bio-oil is separated from the organic solvent by evaporating the solvent from the bio-oil under vacuum.

In some embodiments, a protein from the biomass source is also extracted into a second layer, or phase, comprising the co-solvent composition. The extracted protein can then be separated from the co-solvent composition phase by standard processing protocols. For example, in some embodiments, the alcohol component of the co-solvent composition can be evaporated from the multiple-phase composition to facilitate the precipitation of the extracted protein in the IL salt. The precipitated protein can then be removed by filtration, centrifugation, or the like. Alternatively, in some embodiments, the protein can be fractionated and recovered by the use of column chromatography or the like.

In some embodiments, a fat-soluble pigment is also extracted from the biomass source into the first phase comprising the bio-oil.

In some embodiments, the co-solvent composition is recovered and recycled for use in another reaction or extraction process. Co-solvent composition recovery can be conducted by, for example, centrifugation of the remnant of the extraction mixture to pellet the treated biomass and decanting of the co-solvent composition. In some embodiments, the co-solvent can be recovered by mechanical filtration in which a series of mesh filters with incrementally decreasing pore size are employed.

In some embodiments, the separated bio-oil can be further processed into high-value products. Exemplary uses for the extracted bio-oil include, but are not limited to, application as neutraceuticals, blends in cosmetic or burn creams, lamp oil, wood finish, or as feedstocks for more complex fuels (such as, for example, jet fuel).

In some embodiments the separated bio-oil is reacted in a reaction mixture to produce biodiesel in the form of a fatty acid esters as herein described.

Classes of Lipids Suitable for Transesterification or Other High-Value Products

Lipids are generally defined as any fat-soluble (lipophilic), naturally-occurring molecule, such as, for example, fats, oils, waxes, cholesterol, sterols, fat-soluble vitamins (such as vitamins A, D, E and K), monoglycerides, diglycerides, phospholipids, and the like. The biological functions of lipids include energy storage and acting as structural components of cell membranes. Although the term "lipid" is sometimes used as a synonym for fats, fats are generally known as a subgroup of lipids called triglycerides and are distinguished from fatty acids, which are also a subgroup of lipids. A fatty acid is a carboxylic acid often found with a long unbranched aliphatic tail (chain) that can be either saturated or unsaturated. Triglycerides are triesters of fatty acids with glycerol. Triglycerides in liquid form are commonly known as oils while triglycerides in solid or semi-solid form are generally known as fats.

Fatty acids and triglycerides derived from biomass (such as, for example, microalgae, yeast, bacteria, oil-seeds, plant matter, animal fats) are generally known as bio-oils. Of the lipids that exist (including, but not limited to, fats, oils, waxes, cholesterol, sterols, fat-soluble vitamins (such as vitamins A, D, E and K), monoglycerides, diglycerides, phospholipids, and the like), certain free fatty acids and triglycerides are the principle starting material for biofuels (such as, for example, biodiesel or jet fuel). Bio-oils extracted from microalgae, yeast, and oil-seeds can also be used for non fuel applications such as, for example, wood finish, bases for cosmetic and burn creams, essential oils, lamp oil, and neutraceuticals. Depending upon the structural composition of the fatty acids (such as, for example, carbon chain length, degree of saturation, number and place of double bonds) as well as whether the fatty acids are available in free form or in the form of a triglyceride, bio-oils can have additional uses in, for example, facial or burn creams, cosmetic creams, wound creams, food supplements, waxes, or as a fuel. If suitable as a fuel, the bio-oil itself can be combusted in diesel engines, converted to higher values fuels (such as, for example, jet fuel) through a variety of catalytic processes, or converted to methyl or ethyl fatty acid esters via acid or base catalyzed transesterification reactions.

Extraction of Proteins

Embodiments of the invention provide methods to extract a protein from a biomass source, the methods including: contacting the biomass source with a co-solvent composition containing at least one ionic liquid and at least one PCM; and mixing the biomass source and co-solvent composition, thereby extracting the protein and forming a multiple-phase composition, wherein one phase of the multiple-phase composition comprises the protein. In some embodiments, the method includes separating the protein from the multiple-phase composition.

A biomass source is typically pre-treated prior to undergoing extraction with the IL-based co-solvent. The pre-treatment steps can include, but are not limited to, separation of the biomass from growth media, additional drying of the biomass and physical or mechanical pulverization to increase the surface area of the biomass. Any method known to one of skill in the art can be used to carry out the pre-treatment steps. For example, the biomass source can be separated from growth media by centrifugation, rinsed with deionized water to further remove traces of growth media, dried under vacuum and physically ground prior to undergoing extraction in the IL-based co-solvent.

The biomass source can be contacted with an IL-based co-solvent composition to form the extraction mixture. The manner in which the biomass and the co-solvent composition are combined to form the extraction mixture can be conducted without regard to the sequence of events by which the biomass source and the co-solvent composition provided or without regard to how the biomass source and the co-solvent composition are combined together. In some embodiments, the biomass is added to the co-solvent composition. In some embodiments, the co-solvent composition is added to the biomass. In some embodiments, the components of the co-solvent composition are added individually to the biomass.

Once the extraction mixture is formed, it can be heated while being stirred at temperatures at or below the boiling point of the component in the co-solvent composition with the lowest boiling point. In some embodiments, the extraction mixture can be heated to and incubated at a temperature that is from about 1% to about 100% of the boiling point of the component in the co-solvent composition with the lowest boiling point at pressure. For example, the reaction mixture can be heated to and incubated at about 5%, 10%, 15%, 20%, 25%, 30%, 35%, 40%, 45%, 50%, 55%, 60%, 65%, 70%, 75%, 80%, 85%, 90%, 95% or 100% of the boiling point of the component in the co-solvent composition with the lowest boiling point. In some embodiments, the extraction mixture is heated to and incubated at between about 45° C. to 80° C. In some embodiments, the extraction mixture is incubated at between about 50° C. to 75° C. In some embodiments, the extraction mixture is incubated at between about 55° C. and 70° C.

In some embodiments, the contact between the biomass source and the co-solvent composition in the extraction mixture can be enhanced through the application of sonication, gentle heating, agitation, pressure, and/or radiation energy (e.g., microwave, infrared) to increase in the rate extraction and rate of reaction.

In some embodiments, the extraction can be conducted at temperature and/or pressure values ranging from sub-critical to super-critical values to increase extraction rates and efficiency.

The duration of the extraction can be between about 1 hour to about 48 hours or more. In some embodiments, the duration of the extraction can be between about 2 hours to about 24 hours. In some embodiments, the duration of the extraction can be between about 3 hours to about 18 hours. In some embodiments, the duration of reaction can be between about 5 hours to about 15 hours. In some embodiments, the duration of reaction can be between about 8 hours to about 12 hours. In preferred embodiments, the duration of extraction is the shortest amount of time to achieve substantially complete extraction, such as about 5, 6, 7, 8, 9, 10, 18, 24, 48 or more hours. A substantially complete extraction is one in which no further increase in amount or concentration of extracted product is obtained.

After extraction is substantially complete, the multiple-phase composition that results can be optionally subjected to additional processes to facilitate further separation of the protein from the extraction mixture. For example, the multiple-phase composition can be centrifuged and a first layer, or phase, comprising non-polar molecules such as lipids, bio-oil, and/or fat-soluble components can be removed by decanting or pipetting the layer into a separate container. The protein is typically found in a second phase comprising the co-solvent composition. The second phase comprising the protein and co-solvent composition can subsequently be decanted. The protein can then be separated from the co-solvent composition by standard processing protocols. For example, in some embodiments, the alcohol component of the co-solvent composition can be evaporated from the reaction mixture to facilitate the precipitation of the extracted protein in the IL salt. The precipitated protein can then be removed by filtration, centrifugation, or the like. Alternatively, in some embodiments, the protein can be fractionated and recovered by the use of column chromotography or the like.

In some embodiments, a non-polar molecule, such as a bio-oil, a bio-lipid or a fat-soluble component is also extracted from the biomass source into the first phase comprising non-polar molecules. Separation and isolation of the extracted bio-oil can be accomplished substantially as herein described. In some embodiments the extracted bio-oil is reacted in a reaction mixture to produce biodiesel in the form of a fatty acid ester product as herein described.

In some embodiments, the co-solvent composition is recovered and recycled for use in another reaction or extraction process. Co-solvent composition recovery can be conducted by, for example, centrifugation of the remnant of the extraction mixture to pellet the treated biomass and decanting of the co-solvent composition. In some embodiments, the co-solvent can be recovered by mechanical filtration in which a series of mesh filters with incrementally decreasing pore size are employed.

Extraction of Bio-Polymers

Embodiments of the invention also provide methods to extract a bio-polymer from a biomass source, the methods including: contacting the biomass source with a co-solvent composition containing at least one ionic liquid and at least one PCM; and mixing the biomass source and co-solvent composition, thereby extracting the bio-polymer and forming a multiple-phase composition, wherein one phase of the multiple phase composition comprises the bio-polymer. In some embodiments, the method includes separating the bio-polymer from the multiple-phase composition.

A biomass source is typically pre-treated prior to undergoing extraction with the IL-based co-solvent. The pre-treatment steps can include, but are not limited to, separation of the biomass from growth media, additional drying of the biomass and physical or mechanical pulverization to increase the surface area of the biomass. Any method known to one of skill in the art can be used to carry out the pre-treatment steps. For example, the biomass source can be dried under vacuum and physically ground prior to undergoing extraction in the IL-based co-solvent composition.

The biomass source can be contacted with an IL-based co-solvent composition to form the extraction mixture. The manner in which the biomass and the co-solvent composition are combined to form the extraction mixture can be conducted without regard to the sequence of events by which the biomass source and the co-solvent composition are provided or without regard to how the biomass source and the co-solvent composition are combined together. In some embodiments, the biomass is added to the co-solvent composition. In some embodiments, the co-solvent composition is added to the biomass. In some embodiments, the components of the co-solvent composition are added individually to the biomass.

Once the extraction mixture is formed, it can be heated while being stirred at temperatures at or below the boiling point of the component in the co-solvent composition with the lowest boiling point. In some embodiments, the extraction mixture can be heated to and incubated at a temperature that is from about 1% to about 100% of the boiling point of the component in the co-solvent composition with the lowest boiling point at pressure. For example, the reaction mixture can be heated to and incubated at about 5%, 10%, 15%, 20%, 25%, 30%, 35%, 40%, 45%, 50%, 55%, 60%, 65%, 70%, 75%, 80%, 85%, 90%, 95% or 100% of the boiling point of the component in the co-solvent composition with the lowest boiling point. In some embodiments, the extraction mixture is heated to and incubated at between about 45° C. to 80° C. In some embodiments, the extraction mixture is incubated at between about 50° C. to 75° C. In some embodiments, the extraction mixture is incubated at between about 55° C. and 70° C.

In some embodiments, the contact between the biomass source and the co-solvent composition in the extraction mixture can be enhanced through the application of sonication, gentle heating, agitation, pressure, and/or radiation energy (e.g., microwave, infrared) to increase in the rate extraction and rate of reaction.

In some embodiments, the extraction can be conducted at temperature and/or pressure values ranging from sub-critical to super-critical values to increase extraction rates and efficiency.

The duration of the extraction can be between about 1 hour to about 48 hours or more. In some embodiments, the duration of the extraction can be between about 2 hours to about 24 hours. In some embodiments, the duration of the extraction can be between about 3 hours to about 18 hours. In some embodiments, the duration of reaction can be between about 5 hours to about 15 hours. In some embodiments, the duration of reaction can be between about 8 hours to about 12 hours. In preferred embodiments, the duration of extraction is the shortest amount of time to achieve substantially complete extraction, such as about 5, 6, 7, 8, 9, 10, 18, 24, 48 or more hours. A substantially complete extraction is one in which no further increase in amount or concentration of extracted product is obtained.

After extraction is substantially complete, the multiple-phase composition that results can be optionally subjected to additional processes to facilitate further separation of the bio-polymer product from the multiple-phase composition. For example, the multiple-phase composition can be centrifuged and a first layer comprising the bio-polymer can be removed by decanting or pipetting the layer into a separate container. In some embodiments, the bio-polymer can be separated to by extraction of the bio-polymer into an organic solvent such as hexane. In the event that organic solvent extraction is employed, the extracted bio-polymer can be separated from the organic solvent by evaporating the solvent from the bio-polymer under vacuum.

In some embodiments, a non-polar molecule, such as a bio-oil, a bio-lipid or a fat-soluble component is also extracted from the biomass source into a separate phase.

In some embodiments, the co-solvent composition is recovered and recycled for use in another reaction or extraction process. Co-solvent composition recovery can be conducted by, for example, centrifugation of the remnant of the extraction mixture to pellet the treated biomass and decanting of the co-solvent composition. In some embodiments, the co-solvent can be recovered by mechanical filtration in which a series of mesh filters with incrementally decreasing pore size are employed.

In some embodiments, a bio-oil from the biomass source is also extracted into a second layer, or phase in the multiple-phase extraction mixture. Separation and isolation of the extracted bio-oil can be accomplished substantially as herein described. In some embodiments the extracted bio-oil is reacted in a reaction mixture to produce biodiesel in the form of a fatty acid esters as herein described.

Extraction Conditions

In some embodiments, the extractions as herein described can be carried out in a extraction mixture in which the ratio of biomass to co-solvent composition is about 1000 milligrams biomass per gram of co-solvent composition or less. For example, the ratio of biomass to co-solvent composition can be about 1000, 750, 500, 250, 200, 100, 75, 50, 25 or 10 milligrams biomass per gram of co-solvent composition. Preferably, the ratio of biomass to co-solvent composition is at most about 250 milligrams biomass per gram of co-solvent composition Biomass Starting Material The biomass starting material can be any material from which bio-oil can be extracted. Exemplary biomass starting materials include, but are not limited to, microalgae cells, yeast cells, oil seed crops (including, but not limited to, grape, rape, canola, soybean, safflower, jatropa, radis), agricultural wastes (including, but not limited to, tallow and fats from slaughter houses), whole plants, seaweeds (including, but not limited to, *Laminaria* sp., *Undaria pinnatifida, Hizikia fusiforme* and *Porphyra* sp), halophytes (including, but not limited to, *Salicornia bigelovii*), and the like.

Microalgae are suitable candidates for fuel production because of their higher photosynthetic efficiency, higher biomass production and faster growth compared to other energy crops, and favorable fatty acid profile (Milne, et al. 1990. *Biomass* 21:219-232; Ginzburg. 1993. *Renew. Energy* 3:249-252; Dote, et al. 1994. *Fuel* 73:1855-1857; Minowa, et al. 1995. *Fuel* 74:1735-1738; Y. Chisti, 2007. "Biodiesel from microalgae." *Biotechnology Advances* 25:294-306, each of which is incorporated herein by reference in its entirety). Heterotrophic growth of some microalgae has also been used for high-density production of lipid containing biomass (Shi, et al. 2000. *Enzyme Microb. Technol.* 27:312-318; Shi, et al. 2002. *Biotechnol. Prog.* 18:723-727; Wen, et al. 2002. *Process Biochem.* 37:1447-1453, each of which is incorporated herein by reference in its entirety).

In some embodiments, the microalgae starting material is a heterotrophic strain of *Chlorella* microalgae. *Chlorella protothecoides* (*C. protothecoides*) is a microalgae that can be grown photoautotrophically or heterotrophically on various carbon (e.g. glucose, glycine) and nitrogen (nitrate, ammonia, urea) feedstocks. Heterotrophic growth of *C. protothecoides* can result in high production of biomass and accumulation of high lipid content in cells (F. Chen. 1996. "High cell density culture of microalgae in heterotrophic growth." *Trends in Biotechnology* 14:421-426; Apt, K. E., and P. W. Behrens, 1999. "Commercial developments in microalgal biotechnology." *Journal of Phycology* 35:215-226, each of which is incorporated by reference in its entirety).

In some embodiments, the microalgae starting material can be red algae (such as, for example, *Porphyridium cruentu* and *Galdieria sulphuraria*). In some embodiments, the microalgae starting material can be green algae (such as, for example, *Botryococcus braunii, Euglena gracilis, Chlorella vulgaris* or *Scenedesmus obliquus*). In some embodiments, the microalgae starting material can be blue green algae (such as, for example, *Anacystis nidulans, Microcystis aeruginosa, Oscillatoria rubescens* or *Spirulina platensis*). In some embodiments, the microalgae starting material can include diatoms (such as, for example, *Nitzchia laevis*).

In some embodiments, the microalgae are grown under conditions that increase the lipid content. In the study of fatty acids by photosynthetic microalgal culture, it has been demonstrated that yields are sensitive to a number of environmental factors, including temperature, nitrogen concentration, light intensity, etc. Such environmental factors can be optimized according to techniques known to those of skill in the art (Pohl P., Wagner, H. 1972. "Control of fatty acid and lipid biosynthesis in *Euglena gracilis* by ammonia, light and DCMU." *Z. Naturforsch* 276:53-61; Suen, Y. Hubbard, J. S., Holzer, G., and Tornabene, T. G. 1987. "Total Lipid Production of the Green Alga *Nannochloropsis* SP. QII Under Different Nitrogen Regimes." *Journal of Phycology* 23:289-296; Poirreck, M., Baasch, K. H., and P. Pohl. 1984. "Biomass production, total protein, chlorophylls, lipids and fatty acids of fresh water green and blue-green algae under different nitrogen regimes." *Phytochemistry* 23:207-216, each of which is incorporated herein by reference in its entirety). Production of fatty acids by heterotrophic growth of microalgae can also be influenced by choice of carbon to nitrogen ratio in the feed medium (Chen, F., and M. R. Johns. 1991. "Effect of C/N ratio and aeration on the fatty acid composition of heterotrophic *Chlorella sorokiniana*." *Journal of Applied Phycology* 3:203-209, which is incorporated herein by reference in its entirety). In some embodiments, the technique of metabolic control through heterotrophic growth can be applied to microalga such as *C. protothecoides* that are able to produce bio-oil with significant crude lipid content (Wu, et. al. 1994. *Sci China (B)* 37:326-335, which is incorporated herein by reference in its entirety). In some embodiments, the microalgal oil can be extracted according to the methods herein disclosed. In some embodiments, the microalga can be subjected to direct transesterification reactions to produce a fatty acid ester product according to the methods herein disclosed.

In some embodiments, the biomass source can be a genetically engineered microalgae (Rosenberg, J. N., et al. 2008. "A green light for engineered algae: redirecting metabolism to fuel a biotechnology revolution." *Current Opinions in Biotechnology* 19:430-436, which is incorporated herein by reference in its entirety) or microbial hosts (Fischer, C. R., et al. 2008. "Selection and optimization of microbial hosts for biofuels production." *Metabolic Engineering* 10:295-304; Lee, S. K., et al. 2008. *Current Opinion in Biotechnology* 19:556-583, each of which is incorporated herein by reference in its entirety).

In some embodiments, the biomass source can be a yeast (e.g., *Rhodosporidium toruloides, Rhodotorula glutinis, Rhodotorula gracilis, Rhodotorula graminis, Trichosporon cutaneum, Candida curvata, Hasenula saturnus, Lipomyces lipofer, Lipomyces starkeyi, Yarrowia lipolytica,* and the like). Yeast have been evaluated for their ability to sequester large amounts of bio-oil as a function of media (e.g., nitrogen source, carbon source, C/N ratio) and process (e.g., oxygen) parameters (Yoon, S. H., et al. 1982. "Effect of carbon and nitrogen sources on lipid production of *Rhodotorulu gracilis*" Journal of Fermentation Technology, 60 (3):243-246; Li, Y., et al. 2007. "High-density cultivation of oleaginous yeast *Rhodosporidium toruloides* Y4 in fed-batch culture." Enzyme and Microbial Technology 41:312-317, each of which is incorporated herein by reference in its entirety).

In some embodiments, the biomass source can be an oil seed that can be, for example, but is not limited to: soybean oil seed, peanut oil seed, canola oil seed, sunflower oil, palm oil, grapeseed oil, cottonseed oil, rapeseed oil, and the like (Kumar, A. and S. Sharma. 2008. "An evaluation of multipurpose oil seed crop for industrial uses (*Jatropha curcas* L.): A review." *Industrial Crops and Products* 28 (1):1-10; Azam, M. M., et al. 2005. "Prospects and potential of fatty acid methyl esters of some non-traditional seed oils for use as biodiesel in India." *Biomass and Bioenergy* 29:293-302, each of which is incorporated herein by reference in its entirety).

In some embodiments, the biomass source, or biomass starting materials, are microorganisms grown on glucose. In some embodiments, the biomass starting materials are microorganisms grown on liquid phase carbon waste sources, such as, for example, fruit juice concentrates. In some embodiments, the biomass are microorganisms grown on gas phase $CO_2$ waste sources, such as, power source exhaust streams. In some embodiments, the starting materials are biomass grown on atmospheric $CO_2$; such embodiments can include, but are not limited to, oil-seeds harvested from local trees or shrubs, including, but not limited to, *Callophylum inophylum, Millettia pinnata, Jatropha curas* (Kandpal, J. B. and M. Madan. 1995. "*Jatropha curcas*: A renewable source of energy for meeting future energy needs." *Renewable Energy* 6:159-160, which is incorporated herein by reference in its entirety).

In some embodiments, the biomass source can be photosynthetically grown microalgae. In some embodiments, the biomass source can be obtained from dark fermentation of microalgae or yeast on sugars. In some embodiments, the biomass source can be oil-seed crops, such as, for example, those grown on marginal lands.

In some embodiments, the biomass source can be plant matter, such as, for example, roots, bark, leaves, flowers, branches, twigs, stems and the like. For example, the starting plant matter can be plant leaves or switchgrass that contain biopolymers such as polyhydroxybuterates, lignins, cellulose, and the like.

In some embodiments, the biomass source can be a vegetable oil. Suitable vegetable oils include, but are not limited to, soybean oil, sunflower oil, palm oil and rapeseed oil.

Without limitation, in some embodiments, the biomass source can be at least one of: a yeast, an algae, an oilseed, a soybean, corn, an olive, a sugarbeet, a sugar cane, a switchgrass, a bagasse, and the like.

In some embodiments, the biomass starting material is sequestered in the extraction or reaction mixture. For example, the biomass can be contained in one or more separate receptacles that allow contact with the co-solvent composition and/or catalyst. Typical receptacles for the biomass can include, but are not limited to, filtration sacs with a pore size larger than the molecular size of the co-solvent components and/or the catalyst, tea bags, fine-mesh pouches, and the like.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate embodiments of the present invention. It should be appreciated by those of skill in the art that the techniques disclosed in the examples that follow represent approaches discovered by the inventors to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Recovery of Bio-Oils from Microalgae and from Yeast in Multiple Steps Using Established Techniques A standard extraction approach was employed to estimate the total percentage of extractable bio-oils held within microalgal and yeast biomass. Briefly, samples were dried, pulverized, weighed and subsequently exposed to chloroform-methanol solvent. After the extraction was completed, water was added to the solution to bring about a separation of the biomass-containing methanol phase from the lipid-containing chloroform phase. In order to measure the percentage of extracted bio-oils that can be transesterified (i.e. free fatty acids or triglycerides), the extracted material was subsequently transesterified into fatty acid methyl esters (FAMES) for analysis by gas chromatography (GC) or NMR (Lewis, et al. 2000. "Evaluation of extraction methods for recovery of fatty acids from lipid-producing microheterotrophs." *Journal of Microbial Methods* 43:107-116, which is incorporated herein by reference in its entirety).

Figure 3:
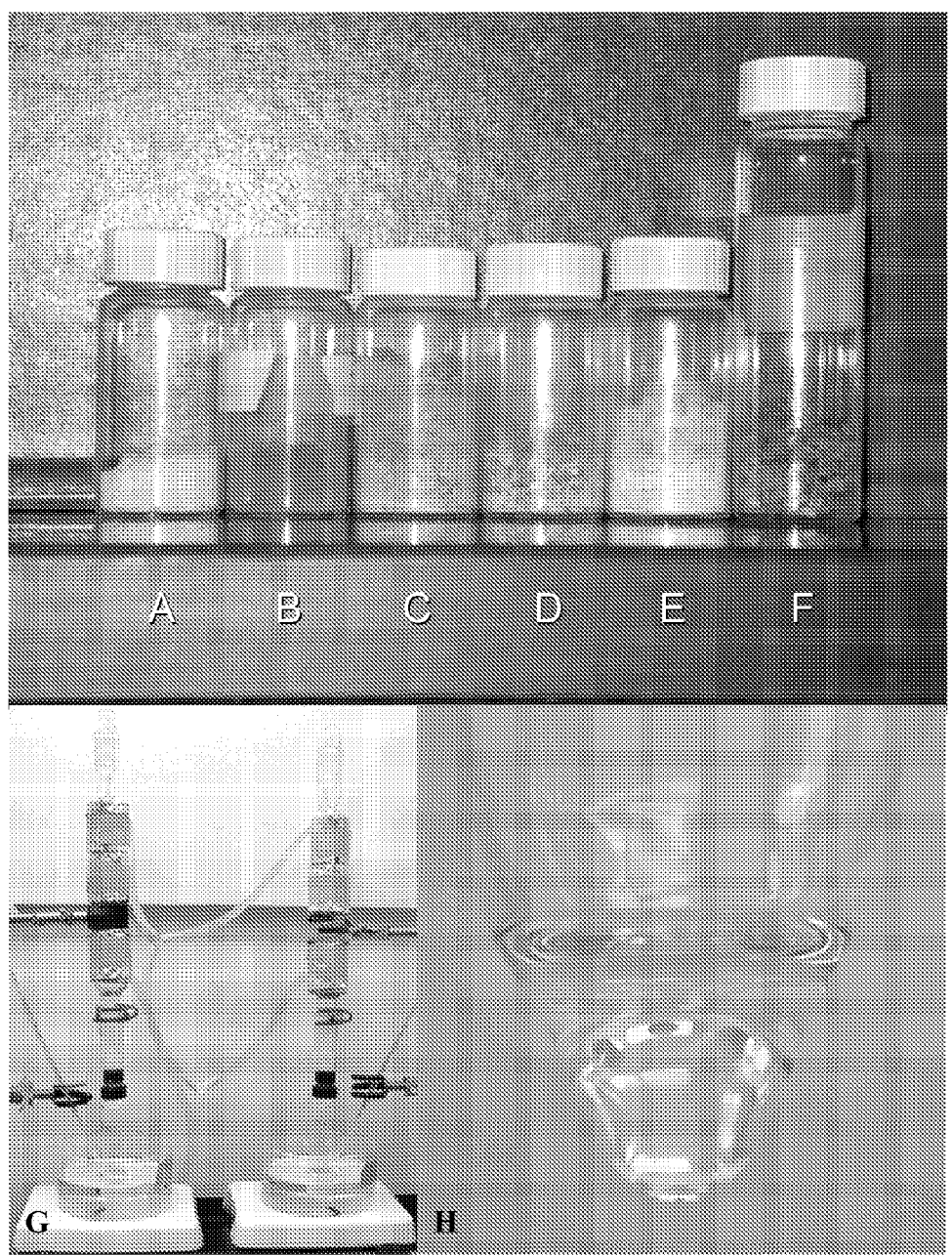
FIG. 3 is a photograph illustrating various forms of biomass source. Samples (A)-(B) illustrate biomass in the form of *C. prototheocoides* microalgae grown in the dark on sugar (A) and in the light on $CO_2$ (B). The remaining samples illustrate biomass in the form of red yeast *R. toruloides* (C), canola oil-seed (D), jatropha oil-seed (E), and kamani oil-seed (F). Image (G) is a photograph showing a typical mixture of biomass and co-solvent composition under reflux. Image (H) is a photograph showing the recovered bio-oil.

Drying. Centrifuged biomass was dried at 80° C. under reduced pressure (−15"Hg (or 385 mm Hg)) to minimize the decomposition of triglycerides that can occur at higher drying temperatures. The biomass was dried until no further loss in weight was observed (duration of drying was approximately 2 hours but was generally dependent upon mass). Alternatively, the microalgal or yeast biomass was freeze dried. After drying the biomass was ground to a fine powder using a mortar and pestle (FIG. 3, top photo). In FIG. 3, (a) represents dried cells of the microalgae *C. prototheocoides* grown on glucose in the dark, (b) represents dried cells of the microalgae *C. prototheocoides* grown $CO_2$ under 12:12 light cycling, (c) represents dried cells of the red yeast *R. toruloides* grown on complex media, (d) represents dried canola bio-oils seeds, (e) represents dried jatropha oil-seeds, and (f) represents dried Kamani oil-seed.

Extraction. The chloroform methanol technique is an established technique to extract fatty acids and triglycerides (i.e. bio-oils) from unicellular biomass (Folch, et al. 1957. "A simple method for the isolation and purification of total lipids from animal tissues." *Journal of Biological Chemistry* 226: 497-509, which is incorporated herein by reference in its entirety). For the extractions, 25 (±10) mg of ground biomass sample was suspended in 2 mL of a 2:1 (v/v) ratio of chloroform:MeOH and allowed to mix under reflux (FIG. 3G) until extraction was complete. The extracted cells and extraction solution were vortexed for about 10 seconds, and the resulting suspension was centrifuged at 4000-6500 rpm for 20 minutes. To facilitate maximum extraction, the supernatant was collected, and the cells were extracted with solvent twice more. The three supernatant extracts were pooled and transferred to a separatory funnel, and a 5% (w/w) aqueous NaCl solution (approximately 4 ml aqueous solution per 50 ml solvent) was added to induce rapid phase separation. After five minutes, the more dense chloroform layer was collected and transferred to a pre-weighed screw-top test tube. The remaining salt water-methanol layer was extracted once more with an additional 2 mL of chloroform, and the chloroform extract was added to the test tube. The pooled fractions were then evaporated off at reduced pressure (400 mbar) and 45° C. using a rotavap (Buchi R210, Switzerland). FIG. 3H shows bio-oil that was recovered from dried cells of *C. prototheocoides*. The amount of bio-oil recovered was directly proportional to the amount of cells extracted and the lipid content (on a wt %) of those cells.

biomass to 19 ml of solvent, which is roughly equivalent to that used in the standard method. The mixture was vortexed for 15 seconds at 800 rpm between each solvent addition. The first variation of the standard method involved a single extraction of the biomass with the Bligh and Dyer extraction solvents (FIG. 4), where the biomass was only exposed to the Bligh and Dyer extraction solution once before being separated by filtration. The second variation of the standard method involved multiple extractions of the biomass (FIG. 5), where the supernatant was separated from the biomass by centrifugation and the biomass was then re-subjected to multiple extraction cycles. Table 2 below summarizes the results from the two approaches.

The difference in the total amount of recovered product is due to the carrying capacity limitation of the Bligh and Dyer extraction solvent. The polar covalent molecule (PCM)-organic solvent system (methanol mixed with either chloroform or hexane) does not have a large carrying capacity for the bio-oil (i.e., at least less than 50 mg of bio-oil per 19 ml of solvent). While the organic-based co-solvent composition was successful in removing the oil from the cells it could not dissolve and hold large amounts of oil. This was evident from the results of the centrifugation process in which the majority of the oil remained behind in a liquid layer below the biomass while the extracted Bligh and Dyer supernatant retained only a small percentage of the overall oil. This indicates that the oil is removed from the biomass, but the solvent system quickly saturates with oil, leaving the excess oil to settle to the bottom of the centrifuge tube under the force of centrifugation. Thus, methods involving multiple extraction and centrifugation steps are required for obtaining maximum yields of oil from the biomass because each extraction involves fresh co-solvent solution that can extract additional oil from the biomass source.

In contrast, embodiments of the present invention involve replacement of the organic liquid of the co-solvent composition with an ionic liquid. Without wishing to be bound by theory, it is hypothesized that the ionic liquid acts to create a medium that enables the passage of extracted lipids through the co-solvent to the surface layer where if forms its own immiscible layer.

TABLE 2

Summary of Extraction Yields

|  | Cake and Filter | Bligh and Dyer Extracts | | Total |
| --- | --- | --- | --- | --- |
| Single Extraction, Multiple Washes | 14 mg | 30 mg (final) | | 44 mg (22% w/w) |
| Multiple Extraction w/ Centrifugation | 5 mg | 80 mg ($1^{st}$&$2^{nd}$extract) | 11 mg ($3^{rd}$ extract) | 96 mg (46% w/w) |

Figure 4:
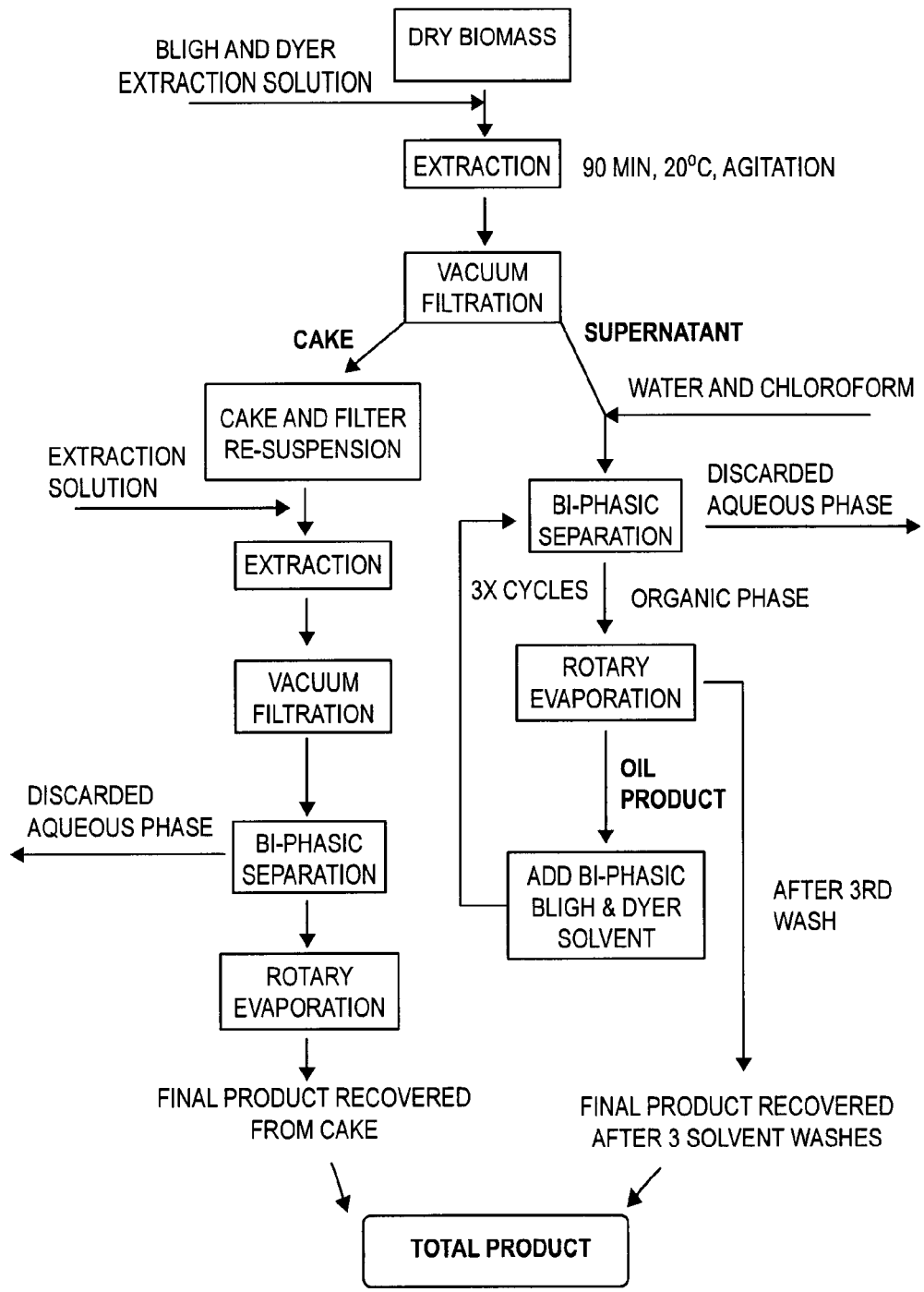
FIG. 4 is a flow diagram illustrating one embodiment for executing a modified version of the Bligh and Dyer extraction procedure described herein.
Figure 5:
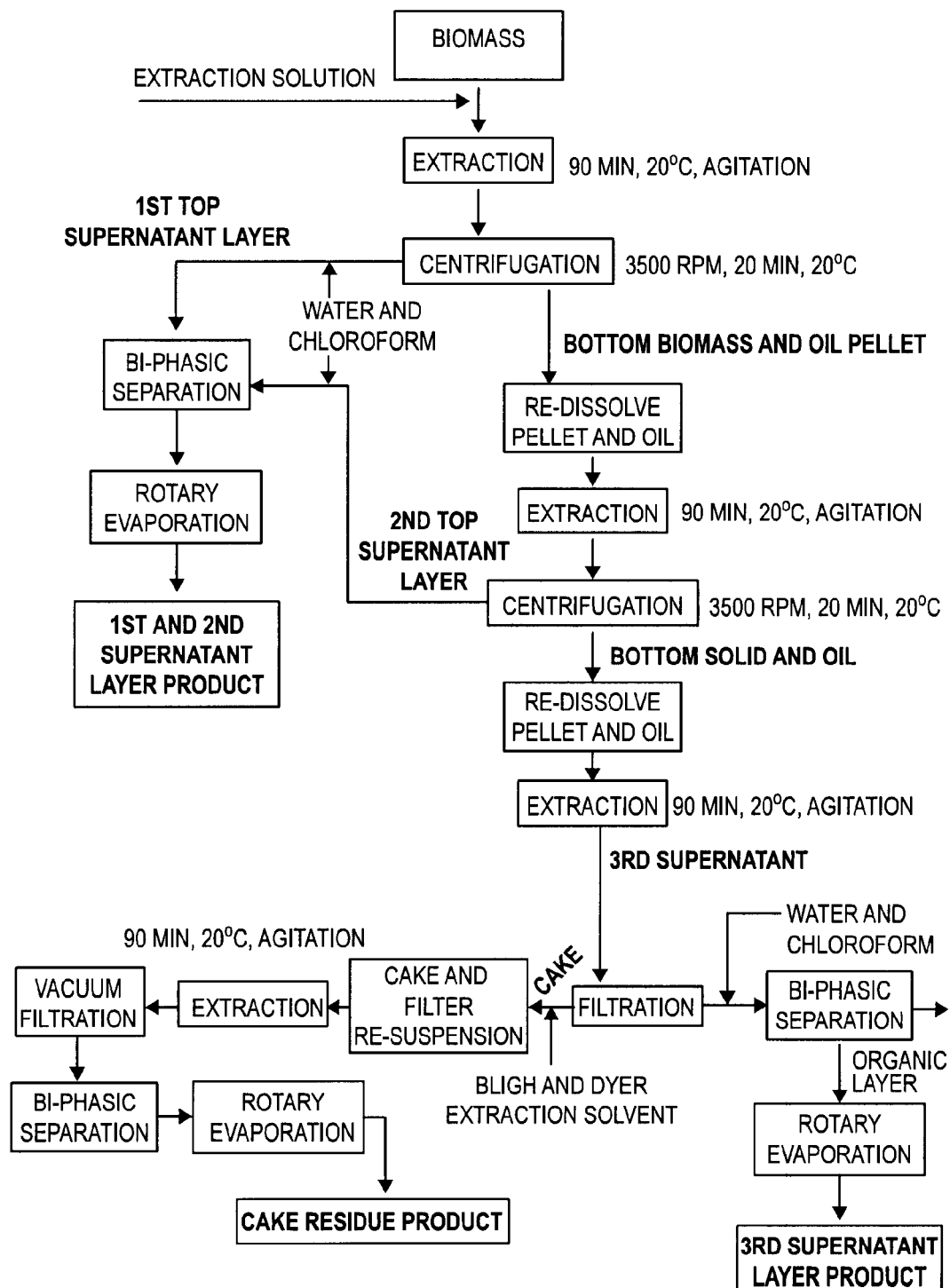
FIG. 5 is a flow diagram illustrating one embodiment for executing a modified version of the Bligh and Dyer procedure described herein.

To better examine the theory underlying the standard approach of Folch et al. (also known as the method of Bligh and Dyer), the method was examined using two separate approaches (FIGS. 4 & 5). In both approaches the initial extraction solvent volumes and biomass were prepared in an identical manner. Approximately 200 mg of freeze dried microalgae, ground in a mortar and pestle for cell disruption, was placed in an extraction test tube. The Bligh and Dyer extraction solvents were then added sequentially to the test tube in the following order: chloroform (5 ml), methanol (10 ml), water (containing 2% (w/w) potassium chloride) (4 ml). The solvent to sample ratio was 200 mg (of >40% (w/w) lipid)

Yields. Batch culture experiments of *C. prototheocoides* grown on glucose and peptone as the nitrogen source indicated that recovery yields of bio-oil ranged from between 34.5% and 64.6% (w/w) of biomass (Table 2, extractable contents determined by gravimetrical measurement). Based on the results of repeated experiments, which involved numerous extractions, a yield of approximately 40% (w/w) for *C. prototheocoides* was calculated as an average value for the bio-oil content produced by cultures grown on glucose as a carbon source, in the dark, under high C/N ratio. These values can vary from batch culture to batch culture as strict process conditions such as pH control, media alterations, and time of culture are typically not realized in batch culture. To further increase the yield of bio-oil, the carbon and/or nitrogen source for the biomass culture can be varied. For example, glycine can be substituted for protein as the nitrogen source, and excess glucose can be added at the end of the exponential growth period to allow the cultures to convert excess carbon (provided as glucose) to lipids in the form of triglycerides (data not shown).

The yeast R. toruloides grown on a complex glucose-peptone-yeast extract-malt extract media produced yields that varied between 4.5% to 7.8% (w/w) (FN3, FN19, Table 3). Although the highest measured recovery yields for yeast were below recovery yields reported in literature, this is due in part to the fact that the growth media for the yeast samples was not optimized for high C/N ratios. In addition, subsequent data showed that yields increased when direct transesterification was applied.

TABLE 3

Extraction of bio-oil from algal and yeast biomass using chloroform-methanol technique of Folch, Lees, and Sloane Stanley (Folch, J. Lees, M., and G. H. Sloane Stanely (1957), supra.)

| Experiment # | Feedstock | Biomass, dry | Recovered extract | Mass % of extractable contents |
|---|---|---|---|---|
| FN 3 | C. protothecoides; NO$_3$ as N source | 0.042 g | 0.019 g | 45.2% |
| FN 3 | C. protothecoides; Peptone media | 0.053 g | 0.024 g | 45.3% |
| FN 3 | R. toruloides Complex media | 0.110 g | 0.005 g | 4.5% |
| FN 10 | C. protothecoides, Peptone as N source | 0.055 g | 0.019 g | 34.5% |
| FN 10 | C. protothecoides, Peptone as N source | 0.048 g | 0.031 g | 64.6% |
| FN 19 | C. protothecoides, Peptone as N source | 0.100 g | 0.039 g | 39.0% |
| FN19 | R. toruloides Complex media | 0.103 g | 0.008 g | 7.8% |
| FN19 | R. toruloides Complex media | 0.103 g | 0.008 g | 7.8% |
| FN28 | C. protothecoides, Fed-Batch culture Peptone as N source | 0.113 g | 0.06 g | 53.1% |
| FN28 | C. protothecoides, Shake flask culture w/glycine as N source | 0.108 g | 0.026 g | 24.1% |
| FN28 | C. protothecoides, Shake flask culture w/o glycine as N source | 0.101 g | 0.022 g | 21.8% |

(The notation FN # is an internal sample reference)

Example 2

Production of Fatty Acid Esters (i.e. Biodiesel) from Nannochloropsis Microalgae by Direct Transesterification in Excess Methanol Solvent Initial experiments were performed on commercially purchased microalgae (i.e. Nannochloropsis). This strain was shown to possess approximately 10% to 15% (w/w) of nonpolar extractable components (a portion of which are lipids, some of which are transesterifiable and some which are not, and a portion which are pigments). Direct transesterification of lipids within Nannochloropsis was studied under a range of conditions. In a first series of experiments, direct transesterification on dried Nanochloropsis cells was conducted in the presence of excess methanol and acid catalyst, followed by subsequent extraction of reaction with hexane solvent.

Figure 6:
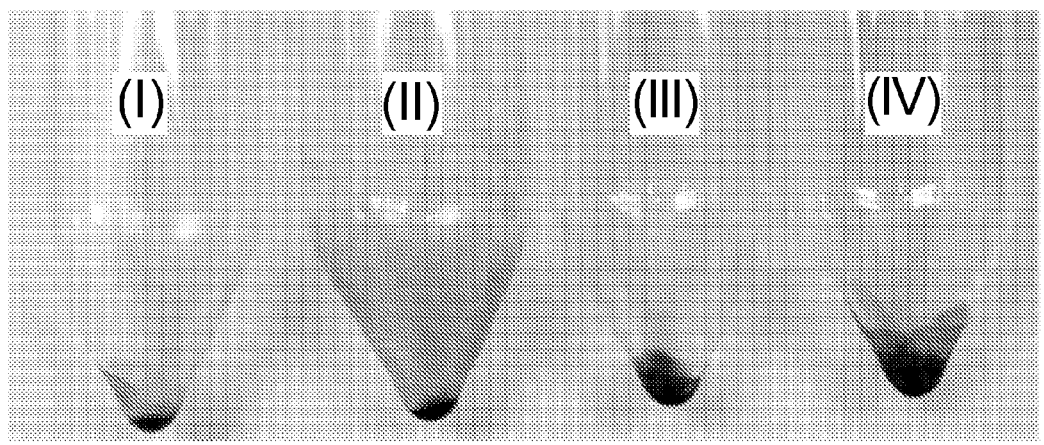
FIG. 6 is a photograph that illustrates recovered products from direct transesterification reactions carried out on microalgae biomass. The microalgae biomass was grown on autotrophic media under 12:12 light cycling.

Nannochloropsis biomass was dried and prepared as described in Example 1. For each experiment, a known amount of biomass (for example, 100 (±10) mg) was transferred into screw top test tubes and submerged in 1.0 mL freshly prepared methanol-acetyl chloride reagent (100:5 (v/v)—providing a final concentration of HCl equal to 3% (w/w) in methanol) for every 25 mg of biomass sample. The tubes were closed and heated to just below the boiling temperature of methanol (about 65° C.) in an oil bath under gentle mixing with a magnetic stirrer for between 1 to 12 hours of reaction time. After cooling to room temperature, 2 ml hexane was added, and the bi-phasic mixture was vortexed for 30 seconds. The upper hexane layer was pooled and neutralized with 1.0 mL of 10% (w/w) aqueous sodium bicarbonate solution. The hexane extraction step was then repeated 3 times to provide maximum recovery of the fatty acid methyl ester (FAME) product from the methanol phase. The hexane extracts were then collected, dried with 3 Å molecular sieves, and filtered directly into pre weighed test tubes using glass fiber syringe filters. The hexane solvent was evaporated off at 60° C. under reduced pressure (330 mbar) using a rotavap (Büchi, R-210) (also known as vacuum distillation). The remaining residue was then weighed to calculate the recovered fatty acid methyl ester (FAME) content. Typical samples of FAME residues recovered from photosynthetically grown microalgae are illustrated in FIG. 6. The color was quite dark and viscous owing to the simultaneous extract of additional (and non transesterifiable) dark green pigments associated with photosynthetic growth of microalgae (such as, for example, chlorophyll).

Analysis and measurement of the FAME product produced by direct transesterification, as well as detection and measurement of any incompletely transesterified triglycerides (i.e. mono or di-glycerides) was carried out by NMR spectral analysis. To accomplish this, the weighed residue (approximately 10 mg) was re-dissolved in 1 ml of chloroform, and a 0.2-mL aliquot of this solution was then transferred to a small HPLC vial and dried under a gentle stream of nitrogen. An amount of 1.00 ml of deuterized chloroform (CDCl$_3$) containing a p-xylene internal standard was then added to the vial. The vials were shaken to facilitate dissolution, transferred to a 5-mm NMR tube, and subsequently analyzed by liquid phase H$^1$NMR measurement.

The results showed that direct transesterification in the presence of high methanol excess resulted in between 4 and 8 wt % FAME content in Nannochloropsis biomass (Table 4, Experiments FN5, FN21-1, FN21-2, FN21-3, FN23-1, FN 23-2). This is consistent with the assumption that not all the nonpolar extractable material was lipid that could be transesterified (i.e. free fatty acids and triglycerides). Extension of the reaction time from 5 to 12 hours showed little to no increase in FAME recovery (Table 4, Experiments FN 21 and 23), indicating that, dependent upon the reaction conditions (choice of catalyst and catalyst concentration, reaction temperature, etc.) reaction times can vary and be optimized. Although varying the catalyst from hydrogen chloride to sulfuric acid showed little to no significant improvement in the overall FAME yield (Table 4, Experiments FN 23-1 and FN 23-2), this result may not be consistent across biomass sources.

TABLE 4

Direct transesterification of *Nannochloropsis* algae
(The notation FN # is an internal sample reference

| | Experiment | | | | | |
|---|---|---|---|---|---|---|
| | FN 5 (Vial 1) | FN21-1 | FN21-2 | FN 21-3 | FN 23-1 | FN 23-2 |
| Biomass (mg) | 113 | 100 | 106 | 107 | 100 | 108 |
| MeOH | 4 mL | 4 mL | 4 mL | 4 mL | 4 mL | 4 mL |
| Molar ratio: MeOH-lipids | High excess | High excess | High excess | High excess | High excess | High excess |
| Acid catalyst concentration in solvent | 3% (w/w) HCl | 3% (w/w) $H_2SO_4$ | 3% (w/w) $H_2SO_4$ + 5 mL hexane | 3% (w/w) HCl | 3% (w/w) HCl | 3% (w/w) $H_2SO_4$ |
| Reaction time | 1 h | 5 h | 5 h | 5 h | 12 h | 12 h |
| FAMES concentration in Biomass (w/w) in %[1] | 8.4 | 5.0 | 3.9 | 5.8 | 6.8 | 6.6 |

Figure 7:
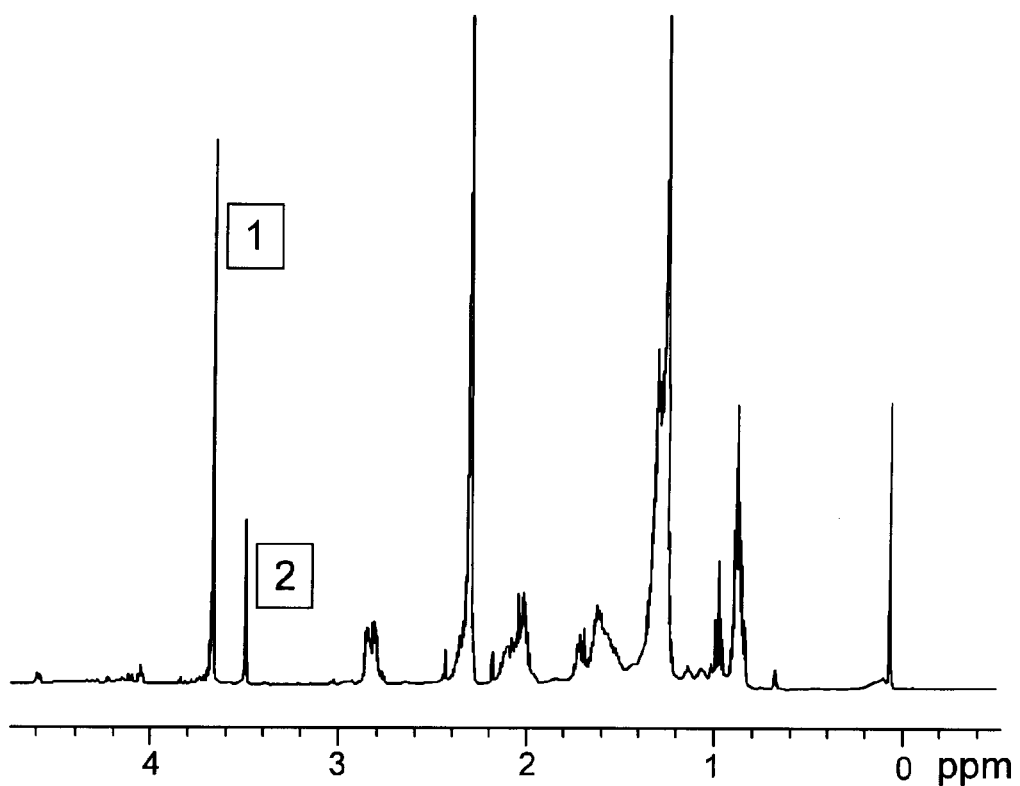
FIG. 7 is an NMR spectra for the product obtained from direct transesterification of *Nanochloropsis* biomass in high methanol excess as described herein.

[1]reported FAMEs concentration are lower than the actual values by a factor of 1.77, due to error in calculation A typical NMR analysis of the resulting FAME product for these experiments after the hexane solvent was evaporated off is shown in FIG. 7. Peak 1 shows the methyl-hydrogen of the FAME product. Peak 2 shows the methyl-hydrogen peak of the remaining methanol.

The lack of mono or di-glycerides peaks to the left of peak 1 indicates a nearly 100 percent conversion of the transesterifiable bio-oil extracted from *Nanochloropsis* cells. These results indicate that direct transesterification can be applied to microalgal cells to achieve a 100 percent conversion of extractable free fatty acids and trigycerides to fatty acid methyl esters.

Example 3

Production of Fatty Acid Esters (i.e. Biodiesel) from *Chlorella protothecoides* Microalgae (Grown on Glucose in the Dark) by Direct Transesterification in Excess Methanol Solvent Direct transesterification of *C. protothecoides* biomass was carried out in excess methanol solvent as described in Example 2. The direct transesterification of *Chlorella* biomass using excess methanol as solvent and a reaction time of 5 hours yielded a fatty acid methyl ester (FAME) concentration on the order of 36% (w/w) that converted the majority of bio-oil (i.e. fatty acids and triglycerides) to FAME product (Table 5, Experiment FN 20-2). Increasing the reaction time to 12 hours did not increase the yield (Table 5, Experiment FN 23-3), confirming this observation. In addition, the weight percent of FAME product (Table 5, Experiments FN 20-2 and FN 23-3) matched the total amount of bio-oil extracted from *C. protothecoides* (Table 3, Experiments FN 10 and FN 19), further supporting the observation that the method of direct transesterification in excess methanol allowed conversion of almost all recoverable bio-oil into FAME product. NMR spectra also showed an absence of mono and di-glyceride peaks, similar to the results obtained for *Nannochloropsis* as discussed in Example 2 (data not shown).

This result can be expected for biomass samples that do not possess significant amounts of lipids that are not transesterified (such as, for example, *C. protothecoides* microalgae grown in the dark and on media (glucose as carbon source and glycine as nitrogen source) that greatly reduces the amount of pigment, including non-transesterifiable pigment, that is produced). In such circumstances, the mass of extractable components can match the mass of FAME product recovered, as the majority of the extractable components are free fatty acids or triglycerides.

Figure 8:
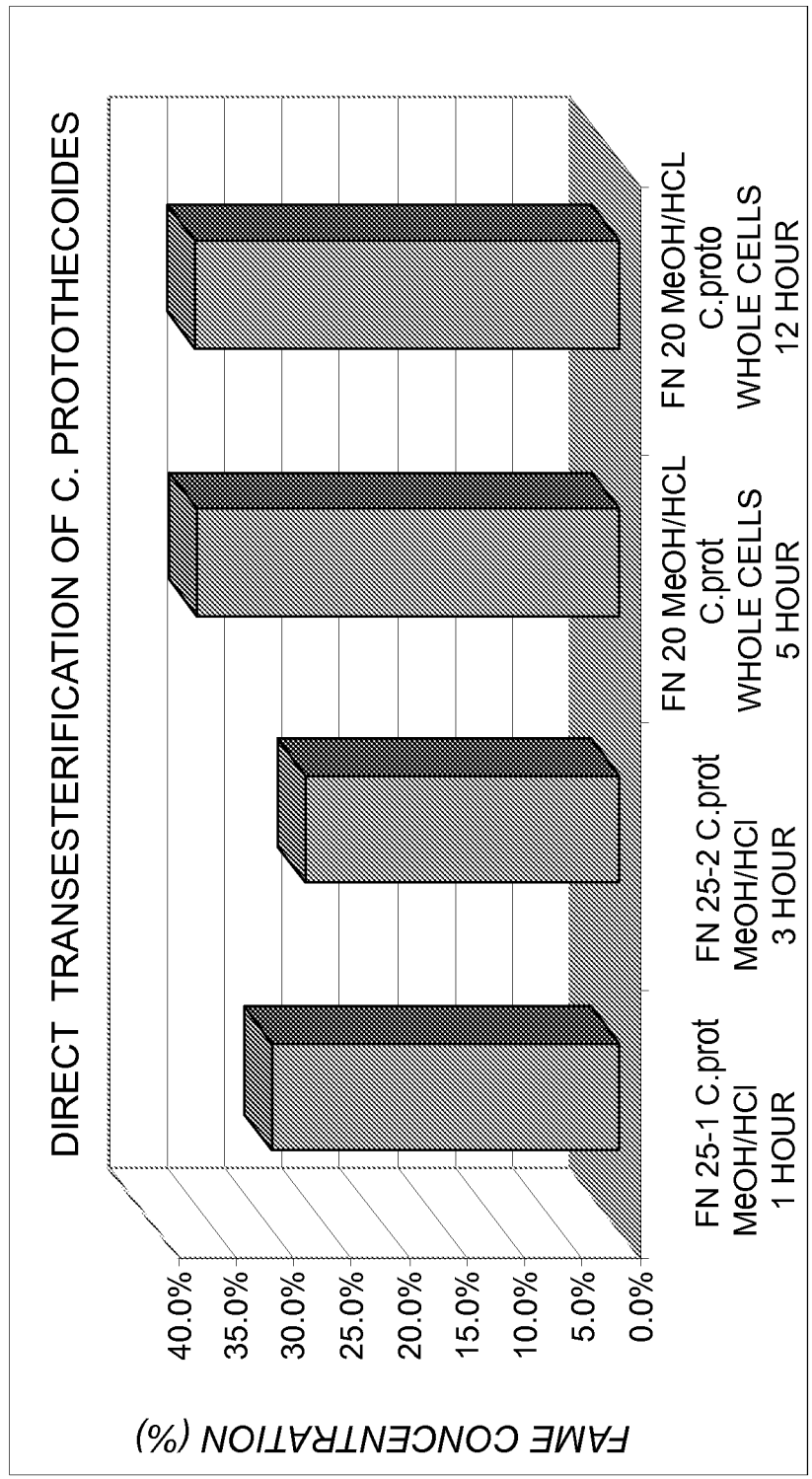
FIG. 8 is a bar chart of fatty acid ester product concentration versus reaction time for the direct transesterification of *C. protothecoides* biomass in high methanol excess as described herein. The fatty acid ester product concentration was calculated from NMR spectra using p-xylene as internal standard.

FIG. 8 illustrates one exemplary comparison of achieved FAME product concentration as a function of reaction time (all other variables being constant, including the source of biomass). As discussed above, the results indicate that an increase of reaction time from 5 to 12 hours provides little improvement in the final ester (FAME product) content.

Figure 9:
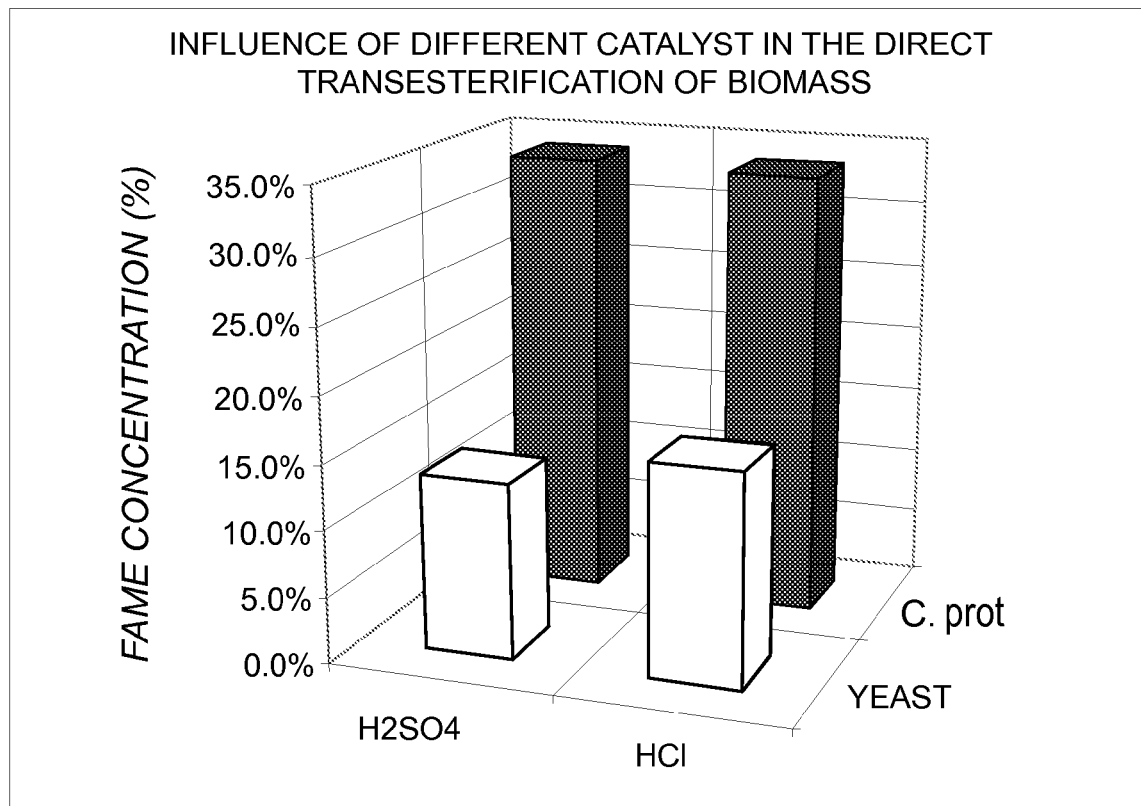
FIG. 9 is a bar chart illustrating comparisons of fatty acid ester product concentration (z-axis) versus biomass type (x-axis) versus catalyst used (y-axis) as described herein.

FIG. 9 shows one exemplary comparison of achieved FAME product as a function of catalyst type for two types of heterotrophically grown biomass: *C. prototheocoides* (microalgae) and *R. toruloides* (yeast) The results indicate that, for direct transesterification of *C. protothecoides* and *R. toruloides* biomass, use of HCl (hydrogen chloride) catalyst vs. use of $H_2SO_4$ (sulfuric acid) catalyst resulted in little significant difference in production and recovery of the FAME product.

TABLE 5

Direct transesterification of *Chlorella protothecoides* biomass in excess methanol solvent

| Experiment # | FN 20-2 | FN 23-3 |
|---|---|---|
| Biomass | C. prototh. | C. prototh. |
| Biomass (mg) | 103 | 100 |
| MeOH | 4.0 mL | 4.0 mL |
| Molar ratio: MeOH-lipids | High excess | High excess |
| HCl %(w/w). in solvent | 3% | 3% |
| Reaction time | 5 h | 12 h |
| FAMES concentration in biomass (% w/w)[1] | 36.6 | 36.7 |

(The notation FN # is an internal sample reference)
[1]reported FAMEs concentration are lower than the actual values by a factor of 1.77, due to error in calculation Example 4

Production of Fatty Acid Esters (i.e. Biodiesel) from Yeast by Direct Transesterification in Excess Methanol Solvent Direct transesterification of the red yeast *R. toruloides* biomass was carried out in excess methanol solvent as described in Examples 2 and 3. The maximum fatty acid methyl ester (FAME) product concentration was obtained when conducting the reaction for at least 5 hours, with an increase in the reaction time from 5 to 12 hours yielding little significant improved yield of FAME product (Table 6, Experiments FN 15, 20-1, and 23-4). It was observed that the amount of FAME recovered from *R. toruloides* (15% to 16% (w/w), Table 6, Experiments FN 20-1 and 23-4) was below that obtained from treatment of *C. prototheocoides* biomass by the same process. This is attributed to the growth of *R. toruloides* on complex media that did not possess C/N ratios that allowed for significant lipid accumulation. However, it was observed that the direct transesterification reaction using excess methanol solvent generally produced better yields of FAME product relative to the standard method of extracting lipids followed by transesterification of the recovered lipids, as described in Example 1 (NMR analysis not shown).

While the direct transesterification approach successfully improved FAME production and yields over the standard extraction and transesterification methods, it is limited as an industrial scale method. Both methanol and hexane solvents are used in excess and must therefore be recovered for re-use. In addition, the recovery steps generally require a vacuum distillation process that is energy intensive. Furthermore, these processes are generally subjected to strict environmental and safety regulations. Accordingly, development of alternative methods and/or steps to produce FAME product was undertaken and the results are reported herein.

TABLE 6

Direct transesterification of *R. toruloides* biomass

| Experiment # | FN 15 | FN 20-1 | FN 23-4 |
|---|---|---|---|
| Biomass | *R. toruloides* | *R. toruloides* | *R. toruloides* |
| Biomass (mg) | 105 | 115 | 100 |
| MeOH | 4.0 mL | 4.0 mL | 4.0 mL |
| Molar ratio: MeOH-lipids | High excess | High excess | High excess |
| HCl % (w/w). in solvent | 3% | 3% | 3% |
| Reaction time: | 1 h | 5 h | 12 h |
| FAME product concentration in Biomass (% w/w)[1] | 13.1% | 16.1% | 15.2% |

(The notation FN # is an internal sample reference)
[1]reported FAMEs concentration are lower than the actual values by a factor of 1.77, due to error in calculation

Example 5

**Production of Fatty Acid Esters (i.e Biodiesel) from *Nannochloropsis* Microalgae by Direct Transesterification in Excess Hexane Solvent**

In an alternative strategy that was pursued to circumvent the need for excess methanol during direct transesterification, the use of excess hexane as the reaction solvent and addition of methanol in strict molar stoichiometric ratios (relative to fatty acids and triglyceride involved in the reaction) was investigated. Accordingly, direct transesterification experiments were conducted in hexane solvent using stoichiometric (or slightly above stoichiometric) amounts of methanol and low or stoichiometric amounts of acid catalyst.

*Nannochloropsis* biomass was dried and prepared as described in Example 1. For each experiment, an amount of 100 (±10) mg biomass was treated with a solvent-reagent mixture containing hexane (3.6 ml), varying molar amounts of methanol and an acid catalyst in the form of acetyl chloride or $H_2SO_4$. For the use of acetyl chloride, the addition of 0.15 ml acetyl chloride (except for FN6, in which a different amount was added) was calculated to react with methanol to yield a hydrogen chloride catalyst concentration of 3.0% (w/w) in the solvent. The vials were closed and heated in an oil bath at 65° C. for from 1 to 3 hours (Table 7). In addition, one experiment was carried out in which an aliquot of methanol/catalyst mixture (0.1 mL methanol, 0.15 mL acetyl chloride) was added after every hour of reaction time (total=3 additions). Thereafter, the biomass was separated by centrifugation (2000 rpm, 15 minutes), and the supernatant solvent layer was decanted and filtered directly into pre-weighed test tubes using glass fiber syringe filters. From this supernatant layer, the hexane solvent was evaporated off at 60° C. under reduced pressure (330 mbar) using a rotavap (Büchi, R-210). The remaining residue was then weighed to calculate the recovered contents. Relative concentration of fatty acid methyl ester (FAME) product was determined by NMR analysis. For NMR analysis, the weighed residue (about 10 mg) was re-dissolved in 1 ml of chloroform from which a 0.2-ml aliquot was transferred to a small HPLC vial and dried under a gentle stream of nitrogen. An amount of 1.00 ml of deuterized chloroform ($CDCl_3$) containing a p-xylene internal standard was then added to the vial. The vials were shaken to facilitate dissolution, transferred to a 5-mm NMR tube, and subsequently analyzed by liquid phase $H^1$NMR measurement.

In a first experiment, a low, non-stoichiometric concentration of acid catalyst (0.03% w/w) was used in the presence of higher than stoichiometric amounts of methanol to separate out the relative effects of the alcohol and acid catalyst (Table 7, FN 6). The reaction was carried out in 1 hour of reaction time. An oil-like substance was recovered from the direct transesterification reaction although NMR analysis did not reveal the presence of any significant characteristic signature of FAMEs in the product. Nevertheless, the result showed the capacity of the alcohol (here, methanol) to facilitate the extraction of bio-oils from biomass in the presence of a solvent (i.e. hexane) with which the FAMEs product are miscible. This result is significant as previous studies (data not shown) indicated that pure hexane is a poor solvent for use in extraction of bio-oil from dried microalgae (regardless of cell rupture pretreatment). Accordingly, it was demonstrated that bio-oils can be recovered in hexane provided that an extracting agent (e.g., methanol) is present.

Additional direct transesterification reactions were performed with the same *Nannochloropsis* biomass in excess hexane solvent but with low (i.e. stoichiometric) amounts of methanol, increased (i.e. above stoichiometric) amounts of acid catalyst (3% w/w) and increased reaction time from 1 to 3 hours. These reactions generally produced low (i.e. <than 1% (w/w)) yields of FAME product (Table 7, Experiments FN 7, 8, 11, 17 and 18). Increasing the reaction time from 1 to 2 hours improved the FAME product yield from 0.7% to 1.3% (w/w) (Table 7, Experiments FN 7 and FN 8), although a further increase in reaction time to 3 hours yielded no further increase in recovered FAME product (Table 7, Experiment FN 11).

In experiments where aliquots of methanol and acid catalyst were added in 1 hour intervals, starting at t=1 hour, a two-fold increase in recovered FAME product was achieved (from 1.5% to 3.3% (w/w), Table 7, Experiments FN 11 and FN 17). These results indicate that the low FAME product could have been caused by loss of either methanol substrate or acid catalyst (or both) due to poor miscibility with hexane. The NMR spectra revealed a peak attributed to the presence of methanol in the reaction mixture after 3 hours of reaction time, indicating that low FAME product yields were likely due to loss of acid catalyst as opposed to loss of methanol substrate by side reactions (data not shown). Thus, the hexane solvent mixture appears unable to dissolve the hydrogen chloride that is formed when the acetyl chloride reacts with methanol. Although repeated additions of catalyst improved the FAME product yield, the methanol was never completely consumed during the reaction.

TABLE 7

Direct transesterification of *Nannochloropsis* algae
(The notation FN # is an internal sample reference)

| | Experiment | | | | | |
|---|---|---|---|---|---|---|
| | FN 6 (vial 2) | FN 7 (vial 5) | FN 8 (vial 3) | FN 11 (vial 1) | FN17 | FN18 |
| Biomass (mg) | 112 | 101 | 102 | 108 | 114 | 104 |
| MeOH | 0.04 ml | 0.005 ml | 0.005 ml | 0.005 ml | 3 × 0.005 ml | 0.005 ml |
| Molar ratio MeOH-lipids | 50:1 | 6:1 | 6:1 | 6:1 | 18:1 | 6:1 |
| HCl % (w/w) in solvent | 0.03% | 3% | 3% | 3% | 3%[1] | — |
| $H_2SO_4$ | — | — | — | — | — | 3% |
| Reaction time | 1 h | 1 h | 2 h | 3 h | 3 h | 2 h |
| FAMES concentration in Biomass (% w/w)[2] | | 0.7 | 1.3 | 1.5 | 3.3 | 0.3 |

[1] every 1 h new cat. added
[2] reported FAMEs concentration are lower than the actual values by a factor of 1.77

Figure 10:
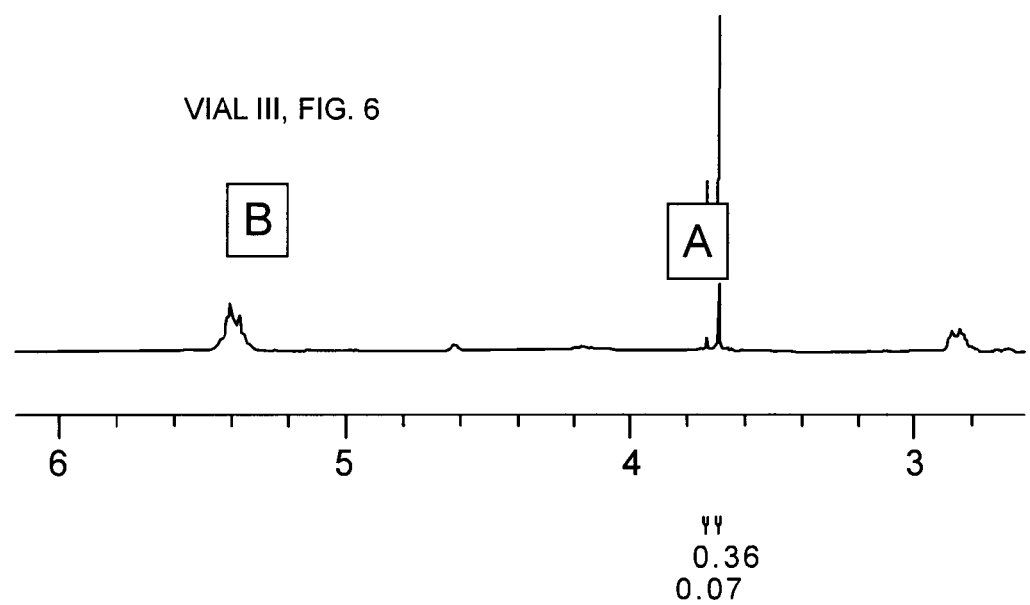
FIG. 10 is a an NMR spectrum of a product produced from a direct transesterification reaction in hexane in the presence of stoichiometric amounts of methanol and acid catalyst (3% w/w) and 1 hour of reaction time as described herein.

A sample of FAME products recovered after 1 hour of reaction time in a reaction involving stoichiometric amounts of both methanol and of acid catalyst (3% w/w) is illustrated in FIG. 6 (III). NMR analysis using p-xylene as an internal standard indicated a conversion efficiency of approximately 5% (w/w), with the remainder of the visible product assumed to be un-reacted bio-oil. FIG. 10 (box a) shows the peak corresponding to FAME product in the reaction mixture. FIG. 10 (box b) shows the peak associated with double bonds indicating the presence of fatty acids that are not fully saturated.

Figure 11:
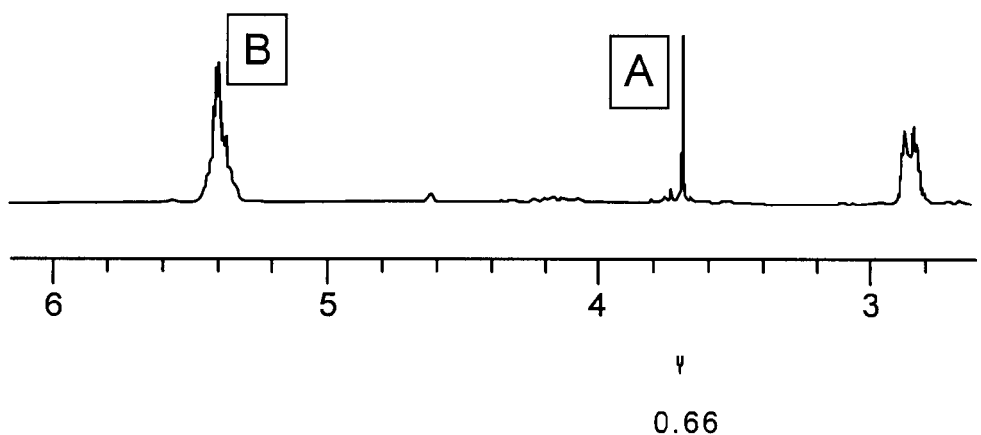
FIG. 11 is an NMR spectrum of the product produced in a direct transesterification reaction in hexane in the presence of stoichiometric amounts of methanol and acid catalyst (3% w/w) and 2 hours of reaction time as described herein. The product corresponds to that found in Vial (III) of FIG. 6.

A sample of FAME product recovered after 2 hours of reaction time is illustrated in FIG. 6 (IV); NMR analysis indicated a conversion efficiency of approximately 10% (w/w). FIG. 11 (box a) shows the peak corresponding to the FAME product in the reaction mixture, which is greater than the peak observed for a reaction time of 1 hour (FIG. 10, box a). Although the results indicate that additional reaction time led to improved yield, the yields were so low as to expect that partially transesterified glycerides (i.e. mono- or di-glycerides) were likewise extracted.

Although the vials (I)-(IV) in FIG. 6 appear to contain material in subsequently increasing amounts, the mass of all vials was approximately equal. The difference in appearance of the products within the vials resulted from differences in final density of the reaction products. The product in vial (I) had the physical characteristics of a solid wax, while the products in vials (III) and (IV) had more of a liquid solution-like consistency. Some insight can be gained by reviewing the NMR profiles in FIGS. 10 and 11 with respect to the peaks found within boxes (b) of each figure. The difference in peak heights indicates a difference in the relative degree of saturation (i.e. more or fewer double bonds), which can dramatically affect viscosity.

The results of this series of experiments indicate that a direct transesterification reaction can be accomplished using hexane solvent and near stoichiometric amounts of alcohol substrate and catalyst, thereby eliminating the need to use excess alcohol, a flammable and corrosive substance that requires further downstream processing for recovery. However, the lack of miscibility of both the alcohol and acid catalyst in hexane limits the efficiency of the reaction.

Example 6

Production of Fatty Acid Esters (i.e Biodiesel) from *C. Protothecoides* and *R. Toruloides* by Direct Transesterification in Excess Hexane Solvent Direct transesterification reactions were performed on both *C. protothecoides* (microalgae) and *R. toruloides* (yeast) biomass in excess hexane solvent, stoichiometric amounts of methanol, higher than stoichiometric amounts of acid catalyst (3% w/w) and reaction times that varied from 1 to 3 hours, as described in Example 5. Table 8 presents the results for these experiments. These reactions also produced low (i.e. <than 1.5% (w/w)) yields of fatty acid methyl ester (FAME) product. Increasing the reaction time from 1 to 3 hours improved the FAME product yield from 0.6% to 0.8% (w/w) for *C. protothecoides* microalgae (Table 8, Experiments FN 11b and FN 11c) and from 0.9% to 1.4% (w/w) for *R. toruloides* yeast (Table 8, Experiments FN 12, vials 1 and 5).

Figure 12:
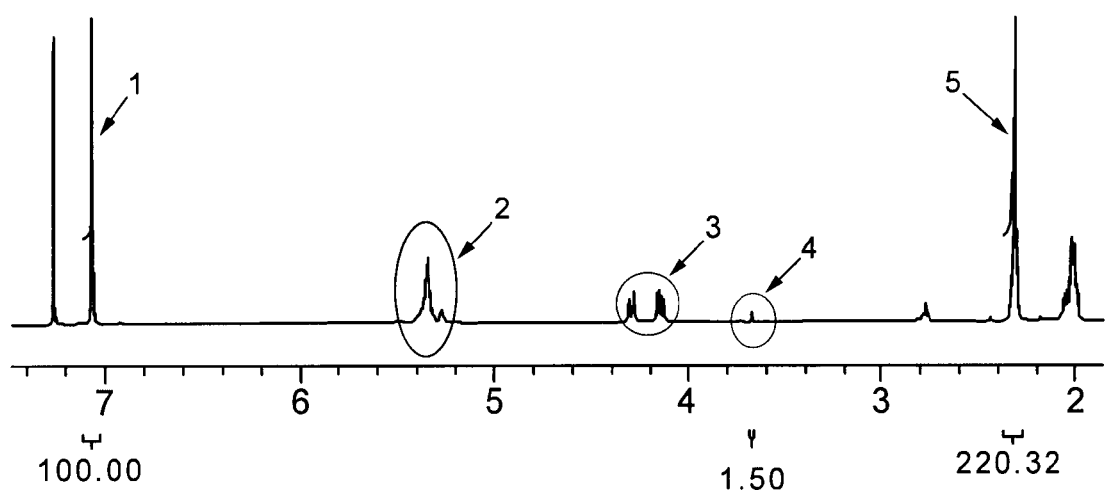
FIG. 12 is an NMR spectrum obtained from the extract of *Chlorella* biomass (Experiment# FN 11b, vial 2) which underwent direct transesterification in excess hexane solvent and stoichiometric amounts of methanol. (1) p-xylene aromatic-hydrogen, standard; (2) fatty acid double bond; (3) triglyceride; (4) fatty acid ester methyl-hydrogen; (5) p-xylene methyl-hydrogen, standard.

In these reactions, only a percentage of the triglycerides were partially transesterified, resulting in di- and mono-glycerides. NMR analysis was performed on a direct transesterification reaction applied to *C. protothecoides* biomass incubated in the transesterification mixture for 1 hour of reaction time (Table 8, Experiment FN 11b). The NMR spectra revealed a peak attributed to presence of a glycerin derivative (FIG. 12, peak #3) that is indicative of unreacted triglycerides (i.e. partially reacted triglycerides that are present as mono- and diglycerides), thereby indicating that the conversion of triglycerides to FAME product was incomplete. It was noted by visual observation that the apparent viscosity of recovered FAME products from longer reaction times was less than that of FAME products recovered after 1 hour reaction time. Thus, difference in viscosity is another trait that distinguishes pure FAME product solutions from those solutions containing unreacted triglycerides and partially reacted di- and mono-glycerides.

TABLE 8

Direct transesterification of Chlorella protothecoides biomass in excess methanol solvent

| | Experiment # | | | |
|---|---|---|---|---|
| | F 11b (vial 2) | FN 11c (vial 3) | FN 12 (vial 1) | FN 12 (vial 5) |
| Biomass | C. prototh. | C. prototh. | R. toruloides | R. toruloides |
| Biomass (mg) | 100 | 104 | 105 | 116 |
| MeOH | 0.005 mL | 0.005 mL | 0.005 mL | 0.005 mL |
| Hexane | 3.64 ml | 3.64 ml | 3.64 ml | 3.64 ml |
| Molar ratio: MeOH-lipids | 6:1 | 6:1 | 6:1 | 6:1 |
| HCl % (w/w) in solvent | 3% | 3% | 3% | 3% |
| Reaction time | 1 h | 3 h | 3 h | 3 h |
| FAMES concentration in Biomass (% w/w)[1] | 0.6 | 0.8 | 0.9% | 1.4% |

(The notation FN # is an internal sample reference)
[1] Reported FAMEs concentration are lower than the actual values by a factor of 1.77, due to error in calculation The results indicate that the direct transesterification reaction can be conducted using solvents other than methanol. The results also indicate that use of new solvents for the direct transesterification reaction can be more efficient.

Example 7

Measuring Production of Biodiesel from Biomass by Direct Transesterification in Ionic Liquid Solvent Using Ionic Liquid Counter Anion as Acid Catalyst Previous studies have reported transesterification reactions carried out on purified oil in the presence of methanol substrate in ionic liquids, incorporating the acidic anion of the ionic liquid for use as the Bronsted acid in the transesterification reaction (Fraga-Dubreuil, J., Bourahla, K., Rahmouni, M., Bazureau, J. P., and J. Hamelin. 2002. "Catalysed esterifications in room temperature ionic liquids with acidic counteranion as recyclable reaction media." *Catalysis Communications* 3:185-190, which is incorporated herein by reference in its entirety). However, direct transesterification has not been attempted on dried biomass. Therefore, direct transesterification was conducted on dried *C. prototheocoides* in ionic liquid 1-Ethyl-3-methylimidazolium hydrogen sulfate [EMIM][$HSO_4^-$] in both the presence and absence of added acid catalyst, in which the ionic liquid anion was applied as the Bronsted acid (Table 9).

In a representative experiment (Table 9, Experiment #FN 27-2), acid catalyst was not added to the reaction medium to determine whether the anion of the ionic liquid (IL) can act as a Bronsted acid and catalyze the transesterification reaction. Although over 52% (w/w) of extractable components was achieved, negligible levels (0.6% w/w) of FAME products were detected by NMR analysis of the extractable components. These results indicate that the IL can act as an excellent extraction medium in the absence of acid catalyst and in the presence of an "extraction" co-component (here, methanol added in at a 1:1 mass ratio to the IL). The low levels of FAME product produced in these reactions indicate that ionic liquids, in which the IL counter anion acts as a weak Bronsted acid, are more suitable as a solvent medium for extraction of bio-oils than for esterificaton reactions (including transesterification reactions) carried out on dried biomass. Thus, in the absence of added catalyst, ionic liquids can be used to extract bio-oils when using ILs that have weak Bronsted acids as a counter anion.

Additional experiments were conducted on dried yeast (*R. toruloides*) biomass and on dried microalgae (*C. prototheocoides*) biomass in which a relatively small amount of acid catalyst was added to the IL. In both experiments, the addition of acid catalyst increased the yield of FAME product produced in the reaction mixture. For example, in the case of *C. prototheocoides* (Table 9, #FN 27-3), an addition of 0.5% (w/w, relative to IL) acid catalyst yielded an increase in NMR-measured FAME product to 3.4% (w/w). A similar improvement (2.2% w/w) was found for application to *R. toruloides*. Thus, these experiments indicate that in the absence of added catalyst, the sole use of the IL counter anion is insufficient to catalyze the direct transesterification of bio-oils in dried biomass to FAME products.

TABLE 9

Results from the direct transesterification of dried microalgal and yeast biomass testing the use of the counter anion of the ionic liquid as the Bronsted acid (EMIM/$H_2SO_4$)
(The notation FN # is an internal sample reference)

| # | Feedstock | Mass | Amount of IL | Catalyst $H_2SO_4$ | Rxn time | Residue (mass) | Residue content[1] | FAMES content[2] |
|---|---|---|---|---|---|---|---|---|
| FN 27-1 | R. toruloides | 501 mg | 2.0 mL | 0.1 mL (~0.5% w/w) | 5 h | 159 mg | 31.7% | 2.2% (w/w) |
| FN 27-2 | C. prototheocoides | 500 mg | 2.0 mL | — | 8 h | 262 mg | 52.4% | 0.6% (w/w) |
| FN 27-3 | C. prototheocoides | 200 mg | 2.0 g | 0.1 mL (~0.5% w/w) | 5 h | 110 mg | 55% | 3.4% (w/w) |

[1] Relative to biomass
[2] reported FAMEs concentration are lower than the actual values by a factor of 1.77, due to error in calculation

Example 8

Figure 14:
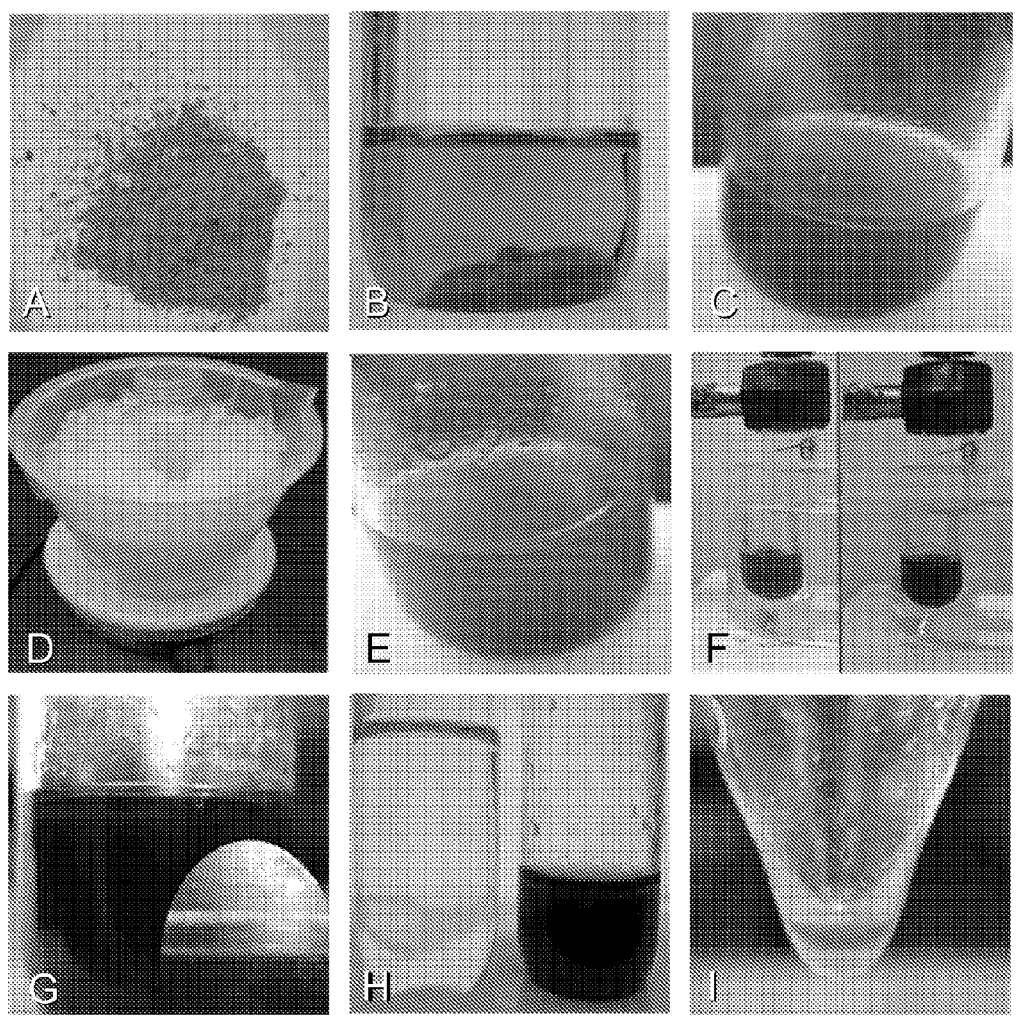
FIG. 14 is a set of photographs that illustrate an embodiment of the direct transesterification method conducted on of yeast biomass in the presence of the IL-PCM co-solvent composition described herein.

Production of Biodiesel from Biomass by Direct Transesterification in Ionic Liquid Co-Solvents Direct transesterification was carried out in the ionic liquid EMIM-H$_2$SO$_4$ in the presence of an acidic catalyst (acetyl chloride) to convert yeast biomass lipids to fatty acid ester products. An amount of 3.0 g of ionic liquid EMIM-H$_2$SO$_4$ (1-Ethyl-3-methyl-imidazolium hydrogen sulfate, FIG. 13B) was mixed with 3.5 g of methanol. Dried, pulverized yeast biomass (200 mg, FIG. 14A) was then added to the solution, and the mixture was stirred (FIG. 14C). Acid catalyst (0.8 mL, final concentration of 6:1 volumetric ratio of methanol:H$_2$SO$_4$) was added under ice-cold conditions (FIG. 14D) to avoid loss of HCl. The mixture was sealed and incubated at temperatures just below the boiling point of methanol for 5 hours (FIG. 14E). During the course of the reaction, the solution darkened in color (FIG. 14F). Upon completion of the reaction, the fatty acid methyl ester (FAME) product separated from the hydrophilic ionic solvent in a top layer (FIG. 14G) which was optionally collected by pipette extraction. If analytical grade product was required (e.g. for NMR and/or GC analysis), the FAME product was extracted into hexane (FIG. 14H) and subjected to a series of purification steps which included filtration and concentration under vacuum in a rotovap (FIG. 14I). The digested biomass was further separated from the reaction mixture by relatively low-speed centrifugation. In some cases, the mild centrifugation step improved the quality of the bio-oil layer formed by the direct transesterification reaction (FIG. 14G).

In additional experiments, the concentration of acid catalyst (H$_2$SO$_4$ or HCl) was varied from between 10% to 30% (w/w, relative to the mass of the entire solvent mixture consisting of methanol and ionic liquid). As shown in Table 10, the addition of acid catalyst increased the yield of FAME product and produced between 12.1% and 14.1% (w/w) FAME product. Relatively equivalent results were achieved regardless of the acid catalyst used (H$_2$SO$_4$ vs. HCl) in the reaction, indicating that relative variation in reaction yield can be attributed to reaction parameters other than the specificity of the catalyst. It is interesting to note that in the yeast biomass feedstock reaction in which HCl was added (Table 10, FN 37), the obtained FAME product concentration was similar to that produced by direct transesterification reactions under conditions of excess methanol and acid catalyst (Table 6).

TABLE 10

Results from direct transesterification of dried biomass using ionic liquids in the presence of added acid catalyst
(The notation FN # is an internal sample reference)

| # | Feedstock | Mass feedstock | Methanol | EMIM-H$_2$SO$_4$ | Catalyst | Rxn time | Residue (mass) | FAMES content[1,2] |
|---|---|---|---|---|---|---|---|---|
| FN 31 | Canola Oil seeds | 518 mg | 6.0 g | 6.0 g | H$_2$SO$_4$ 1.0 ml (final = 15% w/w) | 12 h | 0.264 g | 7.2% |
| FN 32 | C. prototheocoides. | 200 mg | 3.0 g | 3.0 g | H$_2$SO$_4$ 0.5 ml (final = 15% w/w) | 12 h | 0.147 g | 12.6% |
| FN 33 | C. prototheocoides. | 203 mg | 3.0 g | 3.0 g | H$_2$SO$_4$ 1.0 ml (final = 30% w/w) | 12 h | 0.115 g | 22.6% |
| FN 36 | R. toruloides | 203 mg | 3.0 g | 3.0 g | H$_2$SO$_4$ 1.0 ml (final = 30% w/w) | 12 h | 0.053 g | 13.4% |
| FN 37 | R. toruloides | 236 mg | 2.0 g | 2.0 g | HCl (final = 10% w/w) | 12 h | 0.068 g | 14.1% |
| FN 38 | R. toruloides | 202 mg | 3.0 g | 3.0 g | H$_2$SO$_4$ 0.5 ml (final = 15% w/w) | 12 h | 0.055 g | 12.1% |

Figure 15:
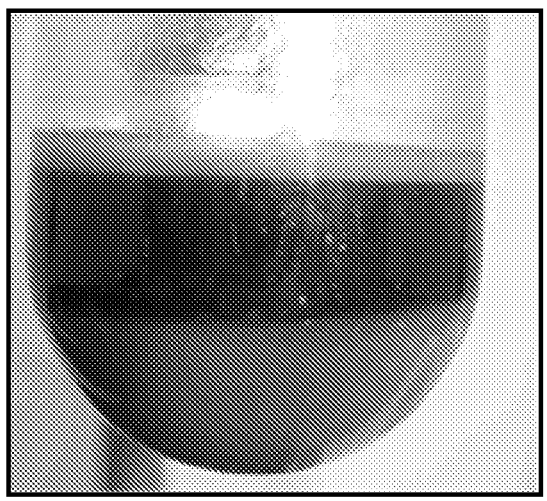
FIG. 15 is a photograph showing the phase separation that occurs after centrifugation of a direct transesterification reaction conducted on *R. toruloides* using a co-solvent composition containing an ionic liquid and methanol as the PCM co-extractant as described herein. A clear phase separation is visible between the lipids/fatty acid ester product phase (top), the ionic liquid phase/methanol phase (middle) and a biomass rich phase (bottom).

[1]Based on biomass (NMR)
[2]reported FAMEs concentration are lower than the actual values by a factor of 1.77, due to error in calculation To decrease the viscosity of the reaction mixture to allow effective mixing, ionic liquids that are chemically similar to EMIM-H$_2$SO$_4$ but less viscous, such as, for example, 1-ethyl-3-methyl-imidazolium methyl sulfate, can be used. In direct transesterification experiments on R. toruloides and C. prototheocoides biomass in 1-ethyl-3-methyl-imidazolium methyl sulfate, better mixing due to the lower viscosity of this ionic liquid was observed while producing similar yields of FAME products (data not shown). Application of a less viscous ionic liquid to improve mixing conditions can reduce the need for equimolar concentrations of a polar covalent molecule to carry out the reaction. A second parameter that can be adjusted to reduce the working viscosity of the reaction mixture is the working reaction temperature. It is also regularly observed that increasing the reaction temperature to 60° C. dramatically reduces the viscosity of the ionic liquids Depending upon the density of the biomass source after the lipids have been extracted, digested "bio-fines" can accumulate in both the lower co-solvent composition phase and the upper immiscible bio-oil or FAME product layer. Any common separation technique (e.g., retention of the biomass in filters or post extraction centrifugation or filtration) can be applied to separate such "bio-fines" accumulation from either phase. The degree to which "biofines" are an issue directly correlates to the biomass source and its structural composition. For example, FIG. 15 shows the separation of biomass for R. toruloides at high biomass concentration. A distinct three phase separation formed after centrifugation (4000 rpm) in which the reacted biomass was clearly suspended in the bottom phase, the co-solvent in the middle, and the FAME top layer. In this example the bio-fines are not a problem. In certain cases, such as with certain microalgae (such as Chlorella sp.), the resulting bio-fines can mix somewhat with the upper immiscible bio-oil layer can create a "mini" emulsion which can undergo further separation to remove the biofines.

Figure 16:
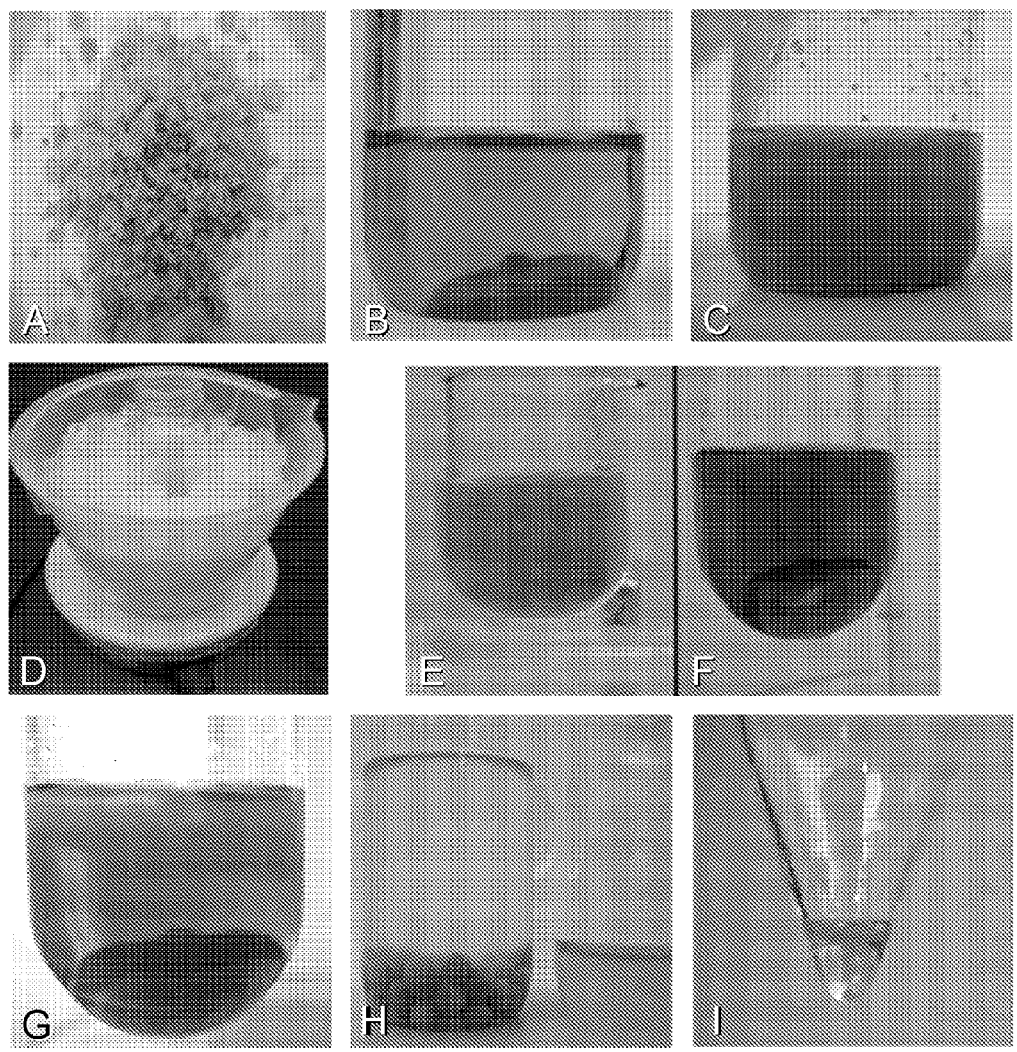
FIG. 16 is a set of photographs that illustrate an embodiment of the direct transesterification method conducted on microalgae biomass in the presence of the IL-PCM co-solvent composition described herein.
Figure 17:
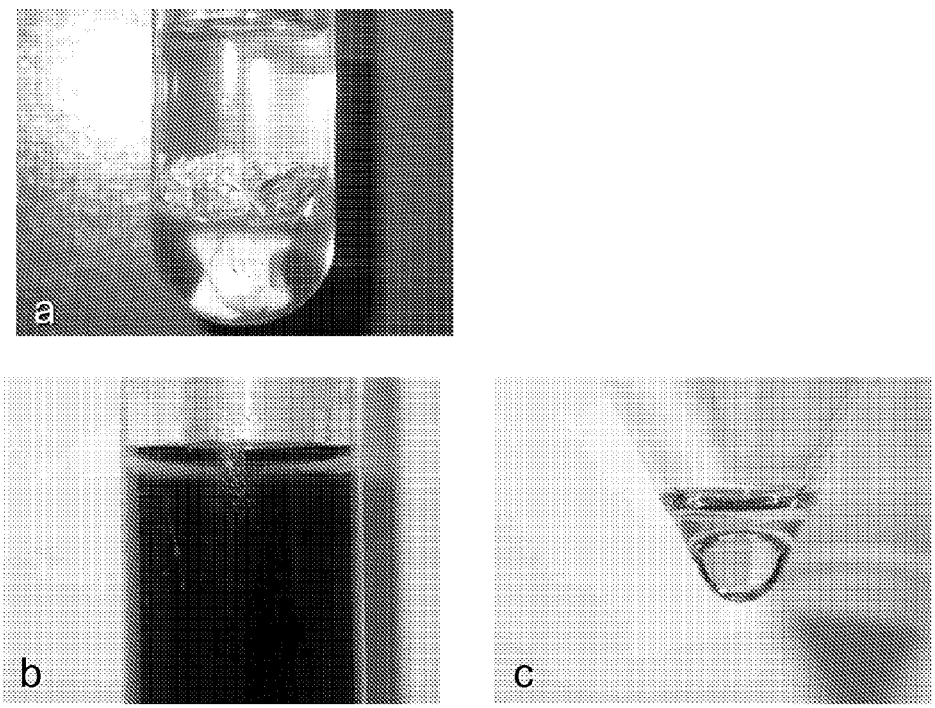
FIG. 17 is a set of photographs showing an embodiment of the direct transesterification method conducted on oil-seed biomass in the presence of the IL-PCM co-solvent composition described herein.

Direct transesterification reactions were also conducted with dried microalgae (*C. prototheocoides*) and with various oil-seeds in EMIN-$H_2SO_4$ (Table 10 and FIGS. 16 and 17, respectively). The yield of FAME product from canola oil seeds was 7.2% (w/w), while that from *C. prototheocoides* microalgae ranged from 12.6% to 22.6% (w/w), depending on the amount of acidic catalyst present in the reaction. Thus, the results of these experiments indicate the broad applicability of this process to a range of biomass source.

These experiments demonstrate that the direct transesterification of biomass in ionic liquids is an advantageous process for producing desired FAME products relative to alternative processes for production of biodiesel. Moreover, these results illustrate that direct transesterification reaction can be carried out in situ in a co-solvent composition comprising an IL and a suitable polar covalent molecule, resulting in a mixture with the desired separation characteristics for facilitating separation of the FAME product.

Example 9

Extraction of Bio-Oils from Biomass in Ionic Liquid Co-Solvents

Figure 18:
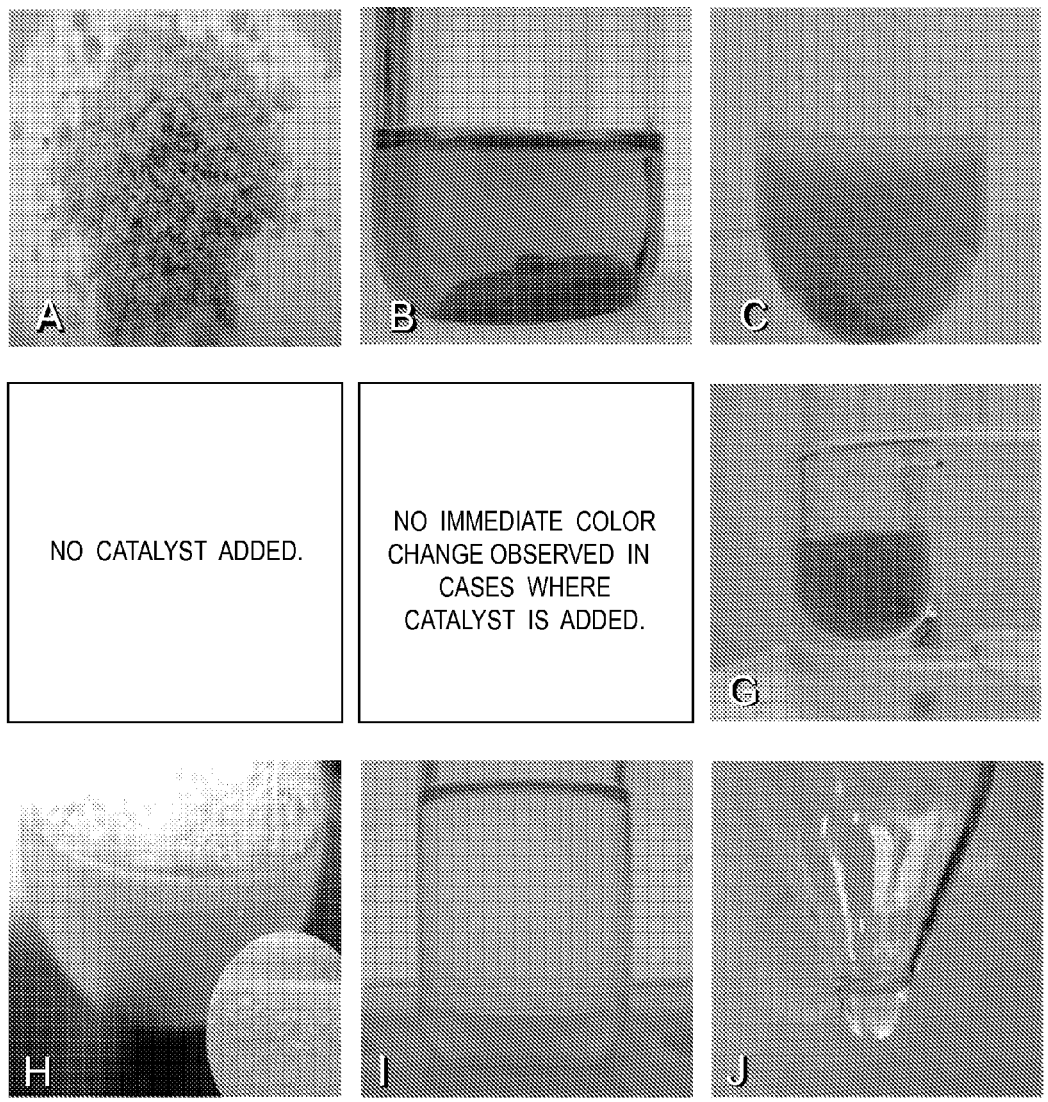
FIG. 18 is a set of photographs showing an embodiment of the extraction method conducted on microalgae biomass in the presence of the IL-PCM co-solvent composition described herein.
Figure 19:
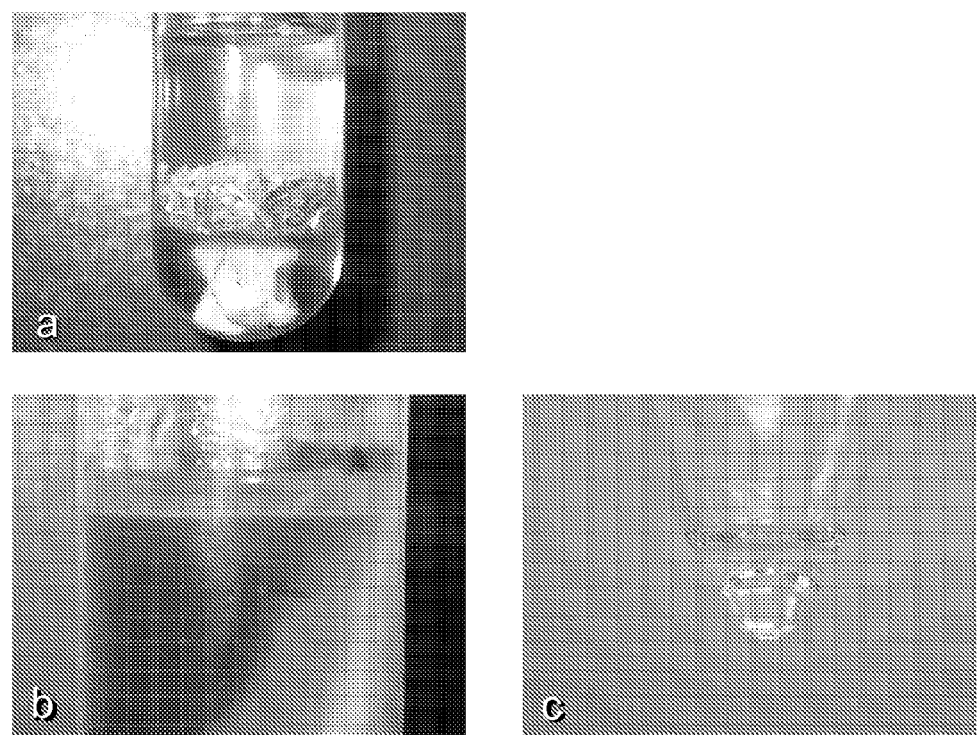
FIG. 19 is a set of photographs showing an embodiment of the extraction method conducted on oil-seed biomass in the presence of the IL-PCM co-solvent composition described herein.

In a series of extraction experiments, bio-oil was extracted from microalgae (FIG. 18), yeast, and oil-seeds (FIG. 19). FIG. 18 shows typical results for the extraction of bio-oils from *C. prototheocoides* microalgae in a co-solvent composition of EMIM-$H_2SO_4$ and methanol; no catalyst was added to the mixture. The reaction parameters are essentially identical to those presented in FIG. 16 except the no acid catalyst was added. Briefly, an amount of 3.0 g of ionic liquid EMIM-$H_2SO_4$ (1-Ethyl-3-methyl-imidazolium hydrogen sulfate) was mixed with 3.5 g of methanol. Dried, pulverized biomass was then added to the solution, and the mixture was stirred. The mixture was sealed and incubated at temperatures just below the boiling point of methanol for 5 hours. Upon completion of the reaction, the bio-oil separated from the hydrophilic ionic solvent in a top layer which was optionally collected by pipette extraction. The digested biomass was further separated from the reaction mixture by relatively low-speed centrifugation. In some cases, the mild centrifugation step improved the quality of the bio-oil layer formed by the direct transesterification reaction. NMR analysis of the extracted bio-oil showed a relatively pure extract devoid of fatty acid ester product (data not shown). FIG. 19 shows typical results for bio-oil extraction from oil-seeds using the same extraction protocol as for microalgae. NMR analysis of the extracted bio-oil also showed a relatively pure extract devoid of fatty acid ester product (data not shown).

These results indicate the applicability of the described method for the extraction of bio-oils without loss of bio-oil to fatty acid ester product as catalyzed through action of the ionic liquid anion acting as a Bronstead acid.

Example 10

Extraction of Bio-Oils from Biomass in Ionic Liquid Co-Solvents: Effect of Polar Covalent Molecule Co Extractant To characterize the effects of the polar covalent molecule on bio-oil extraction, additional extraction experiments were carried out on microalgae. Exemplary polar covalent molecules (PCMs) are listed in FIG. 20 in order of decreasing polarity.

Figure 21:
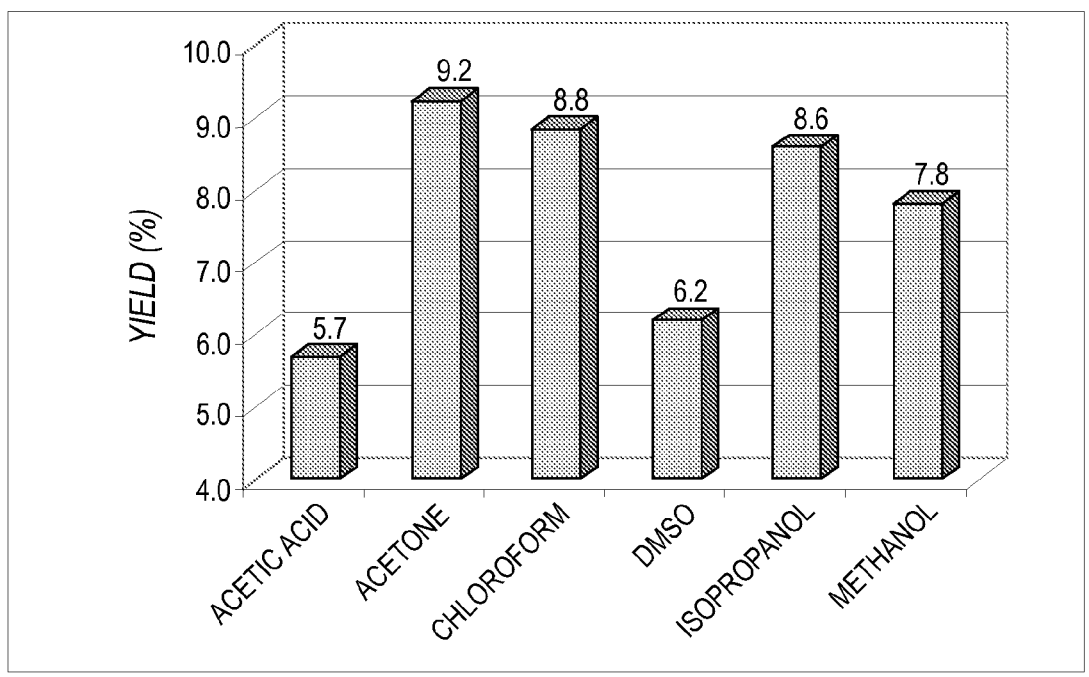
FIG. 21 is a bar graph showing the yield of the bio-oil as a for various PCMs as described herein.

Briefly, extraction experiments were set up involving 400 mg of microalgae, 3.0 g of ionic liquid and 3.5 g of the selected PCM being tested. The extraction was carried out for 18 hours under a sealed tube at 65° C. FIG. 21 shows the effect of candidate polar covalent molecules (PCMs) on the extraction of bio-oil from the microalgal strain *Dunaliella salina*. The gravimetric yield from extractions carried out using acetone, isopropanol (IPA) and chloroform are higher than that achieved with methanol. Use of IPA and chloroform produced similar yields, while acetone gave the highest gravimetrical yield of extracted bio-material. These results indicate that acetone, IPA and chloroform can be an effective for use in bio-oil extraction. Methanol is also useful, but slightly less effective.

Figure 22:
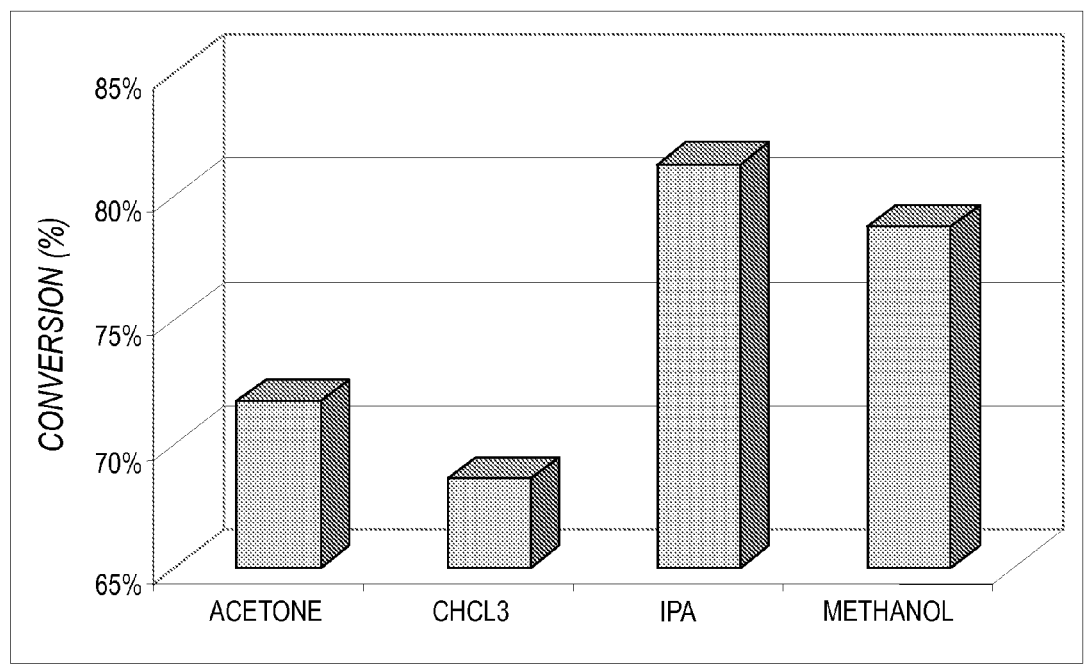
FIG. 22 is a bar graph showing the conversion of bio-oil to fatty acid ester product for various polar covalent molecules as described herein.

The extractable components of a biomass source are not necessarily representative of lipids that can be transesterified into fatty acid ester fuel (i.e. free fatty acids and triglycerides). To investigate the relative degree to which the PCM candidates can extract lipids that undergo transesterification to produce fatty acid ester products, direct transesterification reactions were carried out on the extracted bio-oils. Excess amounts of methanol (5 ml) and acetyl chloride (0.5 ml) were used for these reactions. The results, presented in FIG. 22, indicate that IPA is able to extract the highest content of transesterifiable lipids (as determined by NMR analysis) and appears to be the PCM with the highest extraction capacity of transesterifiable lipids. Methanol also appears to be a suitable candidate. While use of acetone and chloroform as PCMs resulted in a high yield of bio-oil, it was found that use of alcohols generally resulted in higher percentages of extracted bio-oils that could be converted to fatty acid ester products. Nevertheless, these results demonstrate the range of PCMs that can be considered as co-extractants with IL; the choice of PCM can be modified as appropriate for the respective biomass source and desired outcome.

Example 11

Direct Transesterification of Microalgal Biomass in Ionic Liquid Solvent Systems: Effect of Methanol to Triglyceride Molar Ratio For a given set of reaction conditions (e.g., temperature, reaction time, catalyst, IL/biomass ratio), there can be an optimal molar ratio of methanol to transesterifiable lipid above which no further increase in the mass yield of fatty acid ester product is achieved. Thus, the ratio of methanol to transesterifiable lipids (for example, free fatty acid and/or triglycerides) was studied as a parameter that affects reaction yields of fatty acid ester products.

Direct transertification reactions were carried out on *Dunaliella salina* microalgal biomass dissolved in the ionic liquid 1-ethyl-3-methylimmadizolium methyl sulfate (EMIM methyl sulfate) in sealed test tubes. In the reactions, methanol was used as both the co-extractant and the substrate. The same process conditions, including reaction temperature, choice of acid catalyst, catalyst concentration, and reaction time were used across the series of reactions as follows: (a) temperature=65° C., (b) catalyst=acetyl chloride, (c) catalyst concentration=5% v/v of methanol:catalyst, (d) reaction time=18 hours. Meanwhile, the molar ratio of methanol to triglyceride was varied across experiments and ranged from 3000:1 to 100:1. The variation of the molar ratio was achieved by changing the amount of methanol used in the transesterification reaction while holding the amount of biomass constant at 400 mg. It was assumed that the *Dunaliella salina* microalgal strain contained 7% (w/w) triglycerides (lipids) by weight percent.

Figure 23:
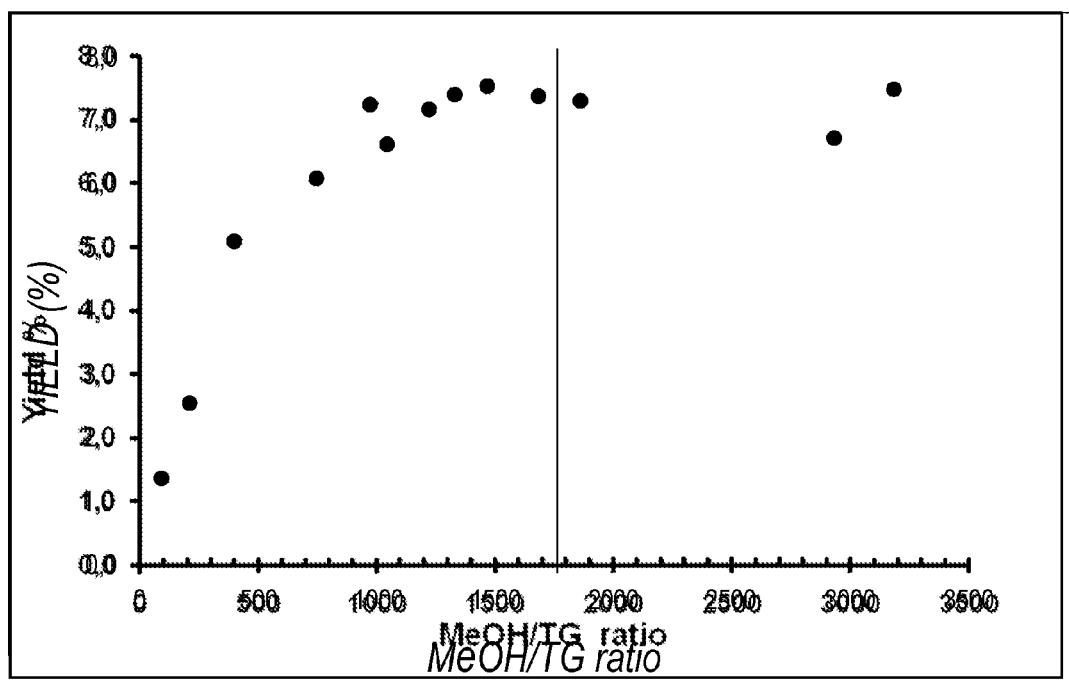
FIG. 23 is a graph illustrating the yield of fatty acid ester product as a function of the molar ratio of alcohol to triglyceride.

FIG. 23 shows the effect of the methanol-to-triglyceride molar ratio on the yield of fatty acid methyl ester (FAME) product recovered in the ionic liquid solution. The threshold ratio under the specified reaction conditions was found to range between 1000:1 and 1500:1. The results indicate that the relative ratio of co-extractant to ionic liquid, for a given mass of biomass, can be minimized to a certain level.

Example 12

Effect of Biomass Loading on Co-Solvent System Extraction

The weight ratio of biomass to co-solvent was varied as a parameter to determine the effect on the efficiency of extracting lipids from the biomass. For each experimental data point, an amount of 400 mg of dried *Chlorella* microalgae was contacted with varying amounts of co-solvent. The mass ratio of biomass to co-solvent ranged from 60 mg/g co-solvent to 250 mg biomass/g co-solvent. The co-solvent composition was kept constant and was based on the composition that was about 46% (w/w) EMIM $CH_3SO_4$ and about 54% (w/w) methanol. The extractions were carried out for 18 hours at 65° C. in sealed test tubes. It was determined that an optimal weight ratio of biomass to co-solvent was found in the range between 80 to 100 milligrams of biomass per gram of co-solvent). Weight ratios greater than 100 milligrams of biomass per gram of co-solvent resulted in a reduction in the maximum yield of bio-oil (38% w/w) obtained from these experiments. This result indicates that the weight ratio of biomass to co-solvent can be varied to obtain the maximum extraction yield of lipids from biomass.

Example 13

Extraction from Wet Biomass Using Co-Solvent System

Studies were conducted to test the use of the co-solvent system on the extraction of lipids from wet biomass. An amount of 80 mg of heterotrophically grown and freeze dried *Chlorella* microalgae was rehydrated with 341 mg of deionized water to form 421 mg of wet biomass having a water content of 80% (by weight). The wet *Chlorella* biomass was contacted with 6.5 grams of a co-solvent composition containing about 46% (w/w) EMIM $CH_3SO_4$ (3.0 g) and 54% (w/w) methanol (3.5 g) and incubated for 18 hours at 65° C. in a sealed test tube. A yield of 25% (w/w) extracted bio-oil was obtained from this experiment. For comparison, under identical extraction conditions, 400 mg of dried *Chlorella* was contacted with the co-solvent composition. The yield of extracted bio-oil obtained from the dried *Chlorella* experiment was 38% (w/w). This result indicates that the co-solvent composition can be used to extract bio-oil from a wet biomass source.

Example 14

Direct Transesterification of Biomass Using Co-Solvent System and a Base Catalyst Studies were conducted to test the effect of using a base catalyst in the direct transesterification methods to produce fatty acid ester product. An amount of 432 mg of dried *Chlorella* biomass was added to a 6.5 g of a co-solvent composition containing about 46% (w/w) EMIM $CH_3SO_4$ (3.0 g) and about 54% (w/w) methanol (3.5 g). This solution was incubated with mixing for 18 hours at 65° C. in a sealed test tube. After 18 hours, 35 mg of NaOH was added to the solution (350 µl from a 3 g NaOH in 30 mL MeOH solution), and the contents were again sealed and incubated for 90 minutes at 65° C. The yield of the fatty acid ester product recovered from the reaction mixture was 45% (w/w) of the original starting biomass weight, which is similar to the bio-oil extraction yield recovered from *Chlorella* biomass (Example 13). The results of this study indicate that the catalyst was effective for use in direct transesterification. In addition, the results indicate that co-solvent composition can be used in a direct transesterification reaction to produce fatty acid ester products from triglycerides using a base catalyst.

Example 15

Bio-Oil Extraction Using Ultrasonic Agitation

Studies were conducted to test the use of ultrasonic agitation in extraction of bio-oil from a biomass source using the co-solvent system disclosed herein. An amount of 610 mg of *Chlorella* microalgae was added to 6.482 g of a co-solvent composition containing about 46% (w/w) EMIM $CH_3SO_4$ (2.993 g) and about 54% (w/w) methanol (3.489 g). The mixture was placed in an ice bath and sonicated at 10 watts RMS for 45 minutes using a sonication tip. The bio-oil yield obtained from the mixture which underwent extraction with sonication was compared to that obtained from extraction of a 606 mg sample of *Chlorella* that underwent extraction without sonication ("thermal extraction"). The yield from obtained from the extraction with sonication was 15% (w/w) (or 91 mg), while the yield obtained from the thermal extraction was 12% (w/w) (or 73 mg). This result indicates that the use of sonication in the extraction of bio-oil using a co-solvent system can increase the bio-oil yield.

Example 16

Protein Extraction from Biomass Using Co-Solvent System

Experiments were conducted to study the extraction of protein from a biomass source using Jatropha oil seeds as an exemplary biomass source. An amount of 527 mg of dried Jatropha seeds were added to 6.5 g of a co-solvent composition containing about 46% (w/w) EMIM $CH_3SO_4$ (3.0 g) and about 54% (w/w) methanol (3.5 g). The extraction was carried out for 18 hours at 65° C. in a sealed test tube. The solution was subsequently washed with three 5 ml aliquots of hexane to remove the extracted lipids. An amount of 139 mg of lipids was recovered from the oil seeds. A Lowry assay was conducted on the remaining co-solvent solution; assay results indicated that proteins were present in the phase containing the co-solvent composition. A gravimetric mass balance of the oil seeds indicated that at least 10 mg of protein were extracted from the oil seeds This result indicates that the co-solvent composition can extract both lipids (partitioned into a separate phase) and protein (extracted into the phase containing the co-solvent composition). Using the Commassie Blue assay (with BSA as the protein of standard) the concentration of extracted protein in the co-solvent was found to be about 6-7% (w/w).

Example 17

Extraction of a Bio-Polymer from a Biomass Source

An amount of plant biomass containing a desired bio-polymer, such as, for example, a polyhydroxybutarate (PHB) polymer is contacted with a co-solvent composition containing 46% (w/w) EMIM $CH_3SO_4$ and about 54% (w/w). The extraction mixture containing the plant biomass and the co-solvent composition were then incubated for 18 hours at 65° C. in a sealed test tube. The solution was subsequently washed with three 5 ml aliquots of hexane to remove the extracted lipids. Using standard assay procedures, it is determined that the phase containing the co-solvent composition contains extracted bio-polymer.

Example 18

Process for Extraction of Bio-Oil and Protein

Figure 24:
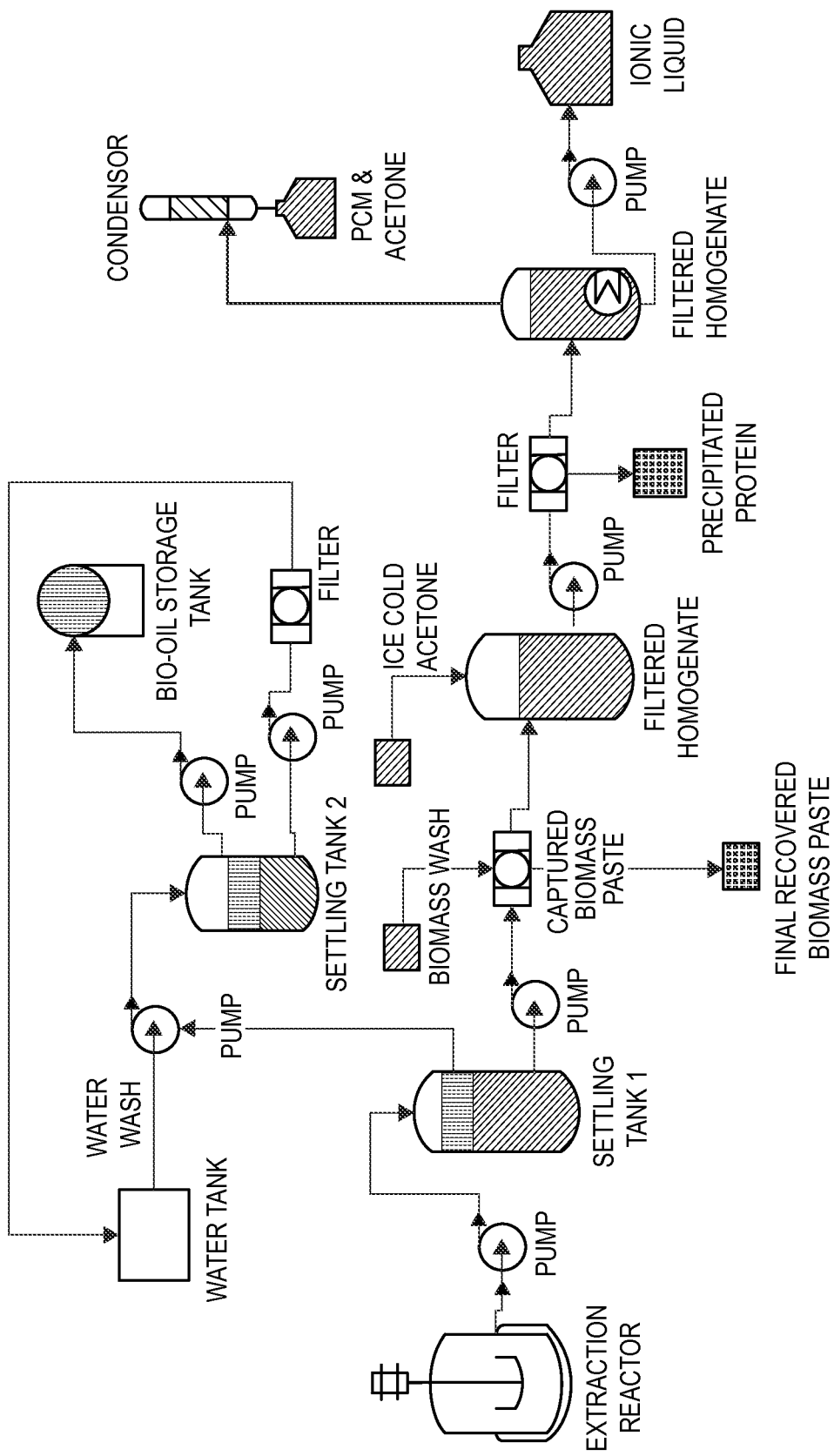
FIG. 24 is a flow diagram illustrating a process to extract bio-oil (or biopolymer, or fat soluble pigments) and protein from biomass using co-solvent compositions comprised of an ionic liquid and polar covalent molecule.

A process for the extraction of bio-oil and protein is provided as follows. Initially, the co-solvent composition is mixed with the biomass in the extraction reactor. The extraction reaction is then run at a temperature that is 90% of the PCM boiling point and under sealed conditions. The extraction reaction is mixed. Upon completion of the extraction reaction, the entire mixture is pumped to a settling tank wherein the bio-oil is partitioned to a top phase and the co-solvent composition, biomass and extracted protein remains in the lower phase. The bio-oil (top phase) is then pumped to a second settling tank where it is washed with water to remove any trace polar contaminating compounds. After washing, the bio-oil is allowed time to partition from the water to form the top phase while the water wash settles to the bottom phase. The bio-oil is then pumped to bio-oil storage tank while the water wash is pumped through a filter before being returned to its original tank. The co-solvent composition and biomass in the first settling tank is pumped through a filter where the biomass is collected as a biomass paste while the co-solvent composition and protein are passed through to a filtered homogenate settling tank. A biomass wash (such as, for example, a TRIS buffer and other reagents) is used to wash the biomass paste and collect any additional residual protein from the biomass paste. This biomass paste wash is then pumped to the homogenate settling tank. Ice cold acetone is added to the filtered homogenate to fully precipitate all the protein in the homogenate. The precipitated protein is collected and dried under vacuum. The co-solvent composition plus acetone then passes through the filter to a second filtered homogenate settling tank. Heat is applied to boil off the polar covalent molecule portion of the co-solvent composition and acetone which is then collected in a condenser. The remaining ionic liquid is then pumped to its own holding vessel. A diagram of the process is summarized in FIG. 24.

Example 19

Direct Transesterification of Biomass Using Ethanol as a Polar Covalent Molecule Direct transesterification is carried out in the ionic liquid EMIM-$H_2SO_4$ in the presence of an acidic catalyst (acetyl chloride) to convert yeast biomass lipids to fatty acid ester products. An amount of 3.0 g of ionic liquid EMIM-$H_2SO_4$ (1-Ethyl-3-methyl-imidazolium hydrogen sulfate, FIG. 13B) was mixed with 3.5 g of ethanol. Dried, pulverized yeast biomass is then added to the solution, and the mixture is stirred. Acid catalyst is added, optionally under ice-cold conditions. The reaction mixture is sealed and incubated at 65° C. for 5 hours. The reaction produces fatty acid ethyl ester product that separates from the hydrophilic ionic solvent in a top layer. The treated biomass is optionally further separated from the reaction mixture by relatively low-speed centrifugation or filtration, which improves the purity of the fatty acid ethyl ester phase formed by the direct transesterification reaction.

Example 20

Direct Transesterification of Biomass Using Butanol as a Polar Covalent Molecule Direct transesterification is carried out in the ionic liquid EMIM-$H_2SO_4$ in the presence of an acidic catalyst (acetyl chloride) to convert microalgae biomass lipids to fatty acid ester products. An amount of 3.0 g of ionic liquid EMIM-$H_2SO_4$ (1-Ethyl-3-methyl-imidazolium hydrogen sulfate, FIG. 13B) was mixed with 3.5 g of butanol. Dried, pulverized microalgae biomass is then added to the solution, and the mixture is stirred. Acid catalyst is added, optionally under ice-cold conditions. The reaction mixture is sealed and incubated at 65° C. for 5 hours. The reaction produces fatty acid butyl ester product that separates from the hydrophilic ionic solvent in a top layer. The treated biomass is optionally further separated from the reaction mixture by relatively low-speed centrifugation or filtration, which improves the purity of the fatty acid butyl ester phase formed by the direct transesterification reaction.

Example 21

Extraction of a Carbohydrate from a Biomass Source

An extraction is carried out from a biomass source to extract carbohydrates and/or sugars from the biomass source. An amount of 250 mg of dried pulverized yeast are added to 6.5 g of a co-solvent composition containing about 46% (w/w) EMIM $CH_3SO_4$ (3.0 g) and about 54% (w/w) methanol (3.5 g). The extraction was carried out for 18 hours at 65° C. in a sealed test tube. A top layer containing biomass components that are immiscible with the co-solvent composition is removed from the multiple-phase composition that forms. An assay is conducted on the remaining co-solvent solution; assay results indicate that carbohydrates and sugars are present in the phase containing the co-solvent composition.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the invention extends beyond the specifically disclosed embodiments to other alternative embodiments and/or uses and modifications and equivalents thereof.

Many variations and alternative elements of the invention have been disclosed. Still further variations and alternate elements will be apparent to one of skill in the art. Among these variations, without limitation, are the selection of biomass source, the selection of polar covalent molecule (PCM), the selection of ionic liquid, and the selection of catalyst (if used). Various embodiments of the invention can specifically include or exclude any of these variations or elements.

In some embodiments, the numbers expressing quantities of ingredients, properties such as molecular weight, reaction conditions, co-solvent composition, ionic liquids, polar covalent molecule, and so forth, used to describe and claim certain embodiments of the invention are to be understood as being modified in some instances by the term "about." Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar referents used in the context of describing a particular embodiment of the invention (especially in the context of certain of the following claims) may be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context the use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans may employ such variations as appropriate, and the invention may be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed may be within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method of extracting a biomass component from a biomass starting material, comprising:
    contacting the biomass starting material with a co-solvent composition, wherein the co-solvent composition comprises at least one ionic liquid and at least one polar covalent molecule (PCM); and
    mixing the co-solvent composition and the biomass starting material, wherein said contacting and mixing results in extraction of biomass components of the biomass starting material and separation into two or more phases of a multi-phase composition, wherein a first phase comprises a first extracted biomass component that is immiscible with the co-solvent composition and a second phase comprises co-solvent composition and second biomass component that is miscible with the co-solvent composition.

2. The method of claim 1, wherein the first extracted biomass component that is immiscible with the co-solvent composition is one selected from the group consisting of: a bio-oil, a bio-polymer, and a fat-soluble pigment.

3. The method of claim 1, wherein the at least one PCM is an alcohol and wherein the contacting further comprises the addition of a catalyst.

4. The method of claim 3, wherein the first extracted biomass component that is immiscible with the co-solvent composition comprises a fatty acid ester product.

5. The method of claim 1, wherein the contacting and mixing results in extraction of a second biomass component that is extracted into a second phase comprising the co-solvent composition.

6. The method of claim 2, wherein the first biomass component that is immiscible with the co-solvent composition is a bio-oil.

7. The method of claim 6, comprising removing the first phase comprising the bio-oil from the multiple-phase composition.

8. The method of claim 6, wherein the multiple phase composition comprises the first phase comprising the bio-oil, a second phase comprising the co-solvent composition, and a third phase comprising the extracted biomass.

9. The method of claim 8, further comprising facilitating separation of the multiple phase composition into the first phase comprising the bio-oil, the second phase comprising the co-solvent composition, and the third phase comprising the extracted biomass.

10. The method of claim 9, wherein the facilitating separation comprises centrifuging the multiple phase composition.

11. The method of claim 9, wherein the facilitating separation comprises passing the multiple phase composition through at least one filter.

12. The method of claim 1, further comprising separating the extracted protein from the co-solvent composition.

13. The method of claim 1, wherein the biomass starting material is at least one selected from the group of: a microalgae, a yeast, an oil seed and a plant matter.

14. The method of claim 1, wherein the at least one polar covalent molecule (PCM) is selected from the group consisting of: alcohols, ketones, organic acids, alkyl halides, sulfoxides, aldehydes, amides, and amines.

15. The method of claim 1, wherein the at least one ionic liquid is comprised of a cation and anion and that is a liquid salt at room temperature.

16. The method of claim 15, wherein the general structure of the cation is one selected from the group consisting of:

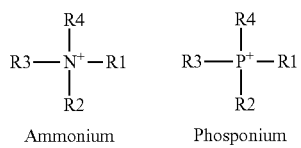
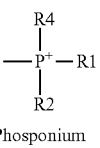
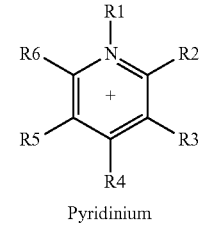

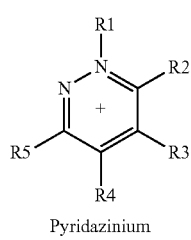
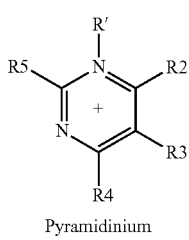

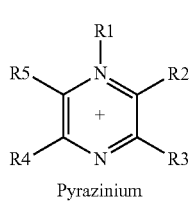
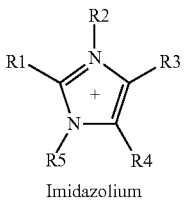

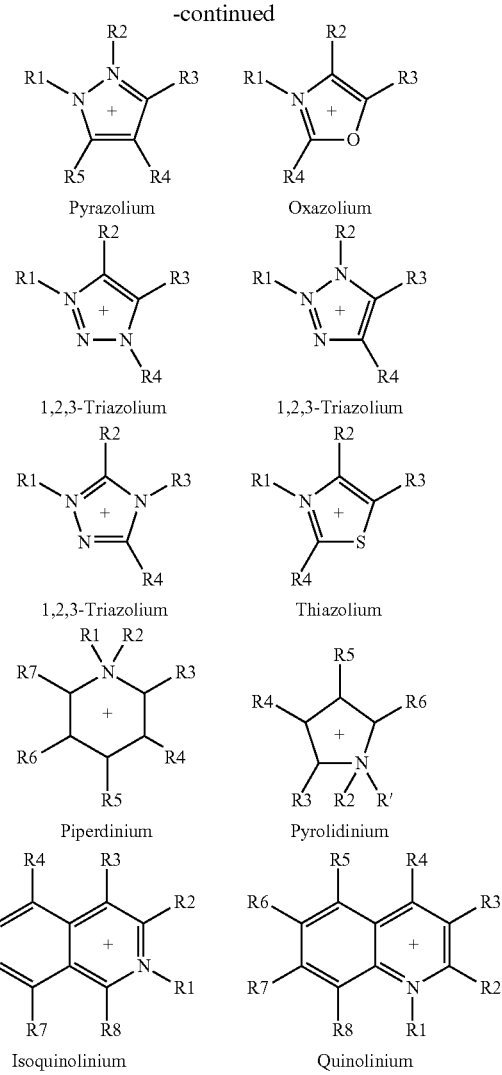

wherein R1 through R6 are independently selected from groups consisting of C0-C6 alkyl, alkenyl, hydroxyalkyl, haloalkyl, alkoxylalkyl, C6-C10 aryl or C8-C16 alkylearyl, or mixtures thereof, wherein C0 denotes hydrogen.

17. The method of claim 16, wherein the cation is an imidazolium cation.

18. The method of claim 15, wherein the anion is one selected from the group consisting of: a halide, a C1-C6 carboxylate, a mono- or di-C1-C10 alkyl sulfosuccinate, a mono- or di-C1-C10 ester sulfosuccinate, a nitrate, a sulfate, an alkylsulfates, a phosphate, an alkylphosphates, an acetate, a halogenoacetates, a tetrafluoroborate, a tetrachloroborate, a hexafluorophosphate, a trifluoro-tris-(pentafluoroethyl) phosphate, a hexafluoroantimonate, a fluorosulfonate, an alkylsulfonate, a perfluoroalkylsulfonate, a bis(perfluoroalkylsulfonyl)amide, a tris-trifluoromethylsulfonyl methylide with formula $C(CF_3SO_2)_3^-$, a bis-trifluoromethylsulfonyl methylide with formula $HC(CF_3SO_2)_3^-$), an arenesulfonate optionally substituted with halogens or halogenalkyl groups, a tetraphenylborate anion, a tetraphenylborate anion the aromatic rings of which are substituted, a tetra-(trifluoroacetoxy)-borate, a bis-(oxalato)-borate, a dicyanamide, a tricyanomethylide, a tetrachloroaluminate anion, and a chlorozincate anion, or mixtures thereof.

19. The method of claim 18, wherein the anion is a methyl sulfate anion.

20. The method of claim 15, wherein the at least one ionic liquid is selected from the group consisting of: 1-ethyl-3-methylimidazolium methyl sulfate, 1-methylimidazolium tetrafluoroborate, 1-alkyl-3-methylimidazolium hydrogensulfonates, 1-butylpyridinium chloride/aluminum chloride, 1-octyl-3-methylimidazolium tetrafluoroborate (OMIM/$BF_4$), [EMIM][$BF_4$], [BMIM][$BF_4$], [HMIM][$BF_4$], [BMIM][$HSO_4^-$], Cl[$BF_4$], a di-alkylimidaxolium salt, a quaternary ammonium salt, and mixtures thereof.

21. The method of claim 20, wherein the at least one ionic liquid is 1-ethyl-3-methyl imidazolium methyl sulfate.

22. A method of direct transesterification of a biomass starting material, comprising:
   contacting the biomass starting material with a co-solvent composition and a catalyst, wherein the co-solvent composition comprises at least one ionic liquid and at least one polar covalent molecule (PCM); and
   mixing the co-solvent composition, catalyst and the biomass starting material, wherein said contacting and mixing results in formation of a fatty acid ester product and a multiple-phase composition, wherein a first phase comprises the fatty acid ester product.

* * * * *

UNITED STATES PATENT AND TRADEMARK OFFICE
CERTIFICATE OF CORRECTION

PATENT NO. : 8,598,378 B2 Page 1 of 1
APPLICATION NO. : 12/404176
DATED : December 3, 2013
INVENTOR(S) : Michael J. Cooney et al.

It is certified that error appears in the above-identified patent and that said Letters Patent is hereby corrected as shown below:

In the Claims:

Column 58, line 23, Claim 16, delete "1,2,3-Triazolium" and insert --1,2,4-Triazolium--.

Column 59, line 10, Claim 20, delete "Cl[BF$_4$]" and insert --[BP]Cl[BF$_4$]--.

Signed and Sealed this
Seventh Day of October, 2014

Michelle K. Lee
*Deputy Director of the United States Patent and Trademark Office*